(12) United States Patent
Raux et al.

(10) Patent No.: US 11,964,154 B1
(45) Date of Patent: Apr. 23, 2024

(54) SIGNAL DELIVERY DEVICES TO TREAT SLEEP APNEA, AND ASSOCIATED METHODS AND SYSTEMS

(71) Applicant: Invicta Medical, Inc., Santa Clara, CA (US)

(72) Inventors: Guillaume Raux, El Paso, TX (US); David Herron, Los Angeles, CA (US); Richard W. O'Connor, Atherton, CA (US); Richard Hamilton Lewis, Perth (AU); Timothy A. Fayram, Gilroy, CA (US)

(73) Assignee: Invicta Medical, Inc., Santa Clara, CA (US)

( * ) Notice: Subject to any disclaimer, the term of this patent is extended or adjusted under 35 U.S.C. 154(b) by 0 days.

(21) Appl. No.: 18/331,109

(22) Filed: Jun. 7, 2023

Related U.S. Application Data

(60) Provisional application No. 63/456,752, filed on Apr. 3, 2023, provisional application No. 63/434,803, filed on Dec. 22, 2022.

(51) Int. Cl.
*A61N 1/36* (2006.01)
*A61N 1/05* (2006.01)
*A61N 1/372* (2006.01)

(52) U.S. Cl.
CPC .......... *A61N 1/3611* (2013.01); *A61N 1/0548* (2013.01); *A61N 1/3601* (2013.01); *A61N 1/36185* (2013.01); *A61N 1/37223* (2013.01)

(58) Field of Classification Search
CPC .. A61N 1/3611; A61N 1/0548; A61N 1/3601; A61N 1/36185; A61N 1/37223
See application file for complete search history.

(56) References Cited

U.S. PATENT DOCUMENTS

| 4,830,008 A | 5/1989 | Meer |
| 5,146,918 A | 9/1992 | Kallok et al. |

(Continued)

FOREIGN PATENT DOCUMENTS

| CN | 201361029 | 12/2009 |
| KR | 10-2019-0049502 | 5/2019 |

(Continued)

OTHER PUBLICATIONS

Atkinson, Martin, "Anatomy for Dental Students," OUP Oxford Fourth Edition, Mar. 14, 2013, p. 298.

(Continued)

*Primary Examiner* — Eric D. Bertram
(74) *Attorney, Agent, or Firm* — Perkins Coie LLP

(57) ABSTRACT

The present technology is generally directed to systems and methods for addressing a patient's sleep apnea. At least some embodiments include an electrode array and a controller. The electrode array can include one or more electrodes and can be configured to be implanted at least proximate to a target tissue of the patient in an orientation, with at least a vector component of the orientation aligned along an inferior-superior axis of the patient. The controller can be communicatively coupled to the electrode array and include one or more non-transitory, computer-readable media having instructions that, when executed by one or more processors of the controller, cause the controller to direct an electrical signal to be delivered by the electrode array to the target tissue.

15 Claims, 26 Drawing Sheets

(56) References Cited

U.S. PATENT DOCUMENTS

| | | |
|---|---|---|
| 5,193,539 A | 3/1993 | Schulman |
| 5,193,540 A | 3/1993 | Schulman |
| 5,265,624 A | 11/1993 | Bowman |
| 5,540,732 A | 7/1996 | Testerman |
| 5,546,952 A | 8/1996 | Erickson |
| 6,132,384 A | 10/2000 | Christopherson et al. |
| 6,240,316 B1 | 5/2001 | Richmond et al. |
| 6,251,126 B1 | 6/2001 | Ottenhoff et al. |
| 6,269,269 B1 | 7/2001 | Ottenhoff et al. |
| 6,345,202 B2 | 2/2002 | Richmond et al. |
| 6,582,441 B1 | 6/2003 | He et al. |
| 6,587,725 B1 | 7/2003 | Durand et al. |
| 6,636,767 B1 | 10/2003 | Knudson |
| 7,189,204 B2 | 3/2007 | Ni et al. |
| 7,252,640 B2 | 8/2007 | Ni et al. |
| 7,367,935 B2 | 5/2008 | Mechlenburg et al. |
| 7,371,220 B1 | 5/2008 | Koh et al. |
| 7,620,451 B2 | 11/2009 | Demarais et al. |
| 7,634,315 B2 | 12/2009 | Mashiach et al. |
| 7,660,632 B2 | 2/2010 | Kirby et al. |
| 7,672,728 B2 | 3/2010 | Libbus et al. |
| 7,680,538 B2 | 3/2010 | Durand et al. |
| 7,684,858 B2 | 3/2010 | He et al. |
| 7,761,167 B2 | 7/2010 | Bennett et al. |
| 7,822,480 B2 | 10/2010 | Park et al. |
| 7,882,842 B2 | 2/2011 | Bhat et al. |
| 7,920,915 B2 | 4/2011 | Mann |
| 8,024,044 B2 | 9/2011 | Kirby et al. |
| 8,249,723 B2 | 8/2012 | McCreery |
| 8,340,785 B2 | 12/2012 | Bonde et al. |
| 8,359,108 B2 | 1/2013 | McCreery |
| 8,498,712 B2 | 7/2013 | Bolea |
| 8,574,164 B2 | 11/2013 | Mashiach |
| 8,577,464 B2 | 11/2013 | Mashiach |
| 8,577,465 B2 | 11/2013 | Mashiach |
| 8,577,478 B2 | 11/2013 | Mashiach et al. |
| 8,585,617 B2 | 11/2013 | Mashiach et al. |
| 8,588,941 B2 | 11/2013 | Mashiach |
| 8,644,957 B2 | 2/2014 | Mashiach |
| 8,655,451 B2 | 2/2014 | Klosterman |
| 8,684,925 B2 | 4/2014 | Manicka et al. |
| 8,688,219 B2 | 4/2014 | Ransom |
| 8,774,943 B2 | 7/2014 | McCreery et al. |
| 8,812,130 B2 | 8/2014 | Stahmann et al. |
| 8,909,351 B2 | 12/2014 | Dinsmoor et al. |
| 8,938,299 B2 | 1/2015 | Christopherson et al. |
| 8,983,572 B2 | 3/2015 | Ni |
| 8,983,611 B2 | 3/2015 | Mokelke et al. |
| 9,031,653 B2 | 5/2015 | Mashiach |
| 9,042,995 B2 | 5/2015 | Dinsmoor |
| 9,061,162 B2 | 6/2015 | Mashiach et al. |
| 9,136,728 B2 | 9/2015 | Dinsmoor |
| 9,155,899 B2 | 10/2015 | Mashiach et al. |
| 9,186,511 B2 | 11/2015 | Bolea |
| 9,205,255 B2 | 12/2015 | Strother |
| 9,227,053 B2 | 1/2016 | Bonde et al. |
| 9,248,302 B2 | 2/2016 | Mashiach et al. |
| 9,308,381 B2 | 4/2016 | Mashiach et al. |
| 9,402,563 B2 | 8/2016 | Thakur et al. |
| 9,409,013 B2 | 8/2016 | Mashiach |
| 9,415,215 B2 | 8/2016 | Mashiach |
| 9,415,223 B2 | 8/2016 | Carbunaru et al. |
| 9,463,318 B2 | 10/2016 | Mashiach et al. |
| 9,486,628 B2 | 11/2016 | Christopherson et al. |
| 9,504,828 B2 | 11/2016 | Mashiach et al. |
| 9,586,048 B2 | 3/2017 | Ternes et al. |
| 9,808,620 B2 | 4/2017 | Kent |
| 9,643,022 B2 | 5/2017 | Mashiach et al. |
| 9,687,664 B2 | 6/2017 | Poon et al. |
| 9,839,786 B2 | 12/2017 | Rondoni et al. |
| 9,849,289 B2 | 12/2017 | Mashiach et al. |
| 9,855,431 B2 | 1/2018 | Ternes |
| 9,888,864 B2 | 2/2018 | Rondoni et al. |
| 9,889,299 B2 | 2/2018 | Ni et al. |
| 9,895,541 B2 | 2/2018 | Meadows et al. |
| 9,907,967 B2 | 3/2018 | Mashiach et al. |
| 9,943,391 B2 | 4/2018 | Chu |
| 9,950,166 B2 | 4/2018 | Mashiach et al. |
| 10,004,913 B2 | 6/2018 | Poon et al. |
| 10,052,097 B2 | 8/2018 | Mashiach et al. |
| 10,195,426 B2 | 2/2019 | Kent |
| 10,195,427 B2 | 2/2019 | Kent |
| 10,195,428 B2 | 2/2019 | Scheiner |
| 10,238,872 B2 | 3/2019 | Pivonka et al. |
| 10,314,501 B2 | 6/2019 | Zitnik et al. |
| 10,335,596 B2 | 7/2019 | Yakovlev et al. |
| 10,512,782 B2 | 12/2019 | Mashiach et al. |
| 10,583,297 B2 | 3/2020 | Ni |
| 10,594,166 B2 | 3/2020 | Ho et al. |
| 10,716,940 B2 | 7/2020 | Mashiach et al. |
| 10,744,339 B2 | 8/2020 | Makansi |
| 10,751,537 B2 | 8/2020 | Mashiach et al. |
| 10,806,926 B2 | 10/2020 | Christopherson et al. |
| 10,828,502 B2 | 11/2020 | Poon et al. |
| 10,898,709 B2 | 1/2021 | Wagner et al. |
| 10,932,682 B2 | 3/2021 | Christopherson et al. |
| 10,967,183 B2 | 4/2021 | Yakovlev et al. |
| 10,994,139 B2 | 5/2021 | Fayram et al. |
| 11,090,491 B2 | 8/2021 | Mashiach et al. |
| 11,160,980 B2 | 11/2021 | Mashiach et al. |
| 11,253,712 B2 | 2/2022 | Mashiach |
| 11,266,837 B2 | 3/2022 | Scheiner et al. |
| 11,273,305 B2 | 3/2022 | Scheiner et al. |
| 11,291,842 B2 | 4/2022 | Caparso et al. |
| 11,298,549 B2 | 4/2022 | Mashiach et al. |
| 11,324,950 B2 | 5/2022 | Dieken et al. |
| 2001/0023362 A1 | 9/2001 | Kobayashi |
| 2003/0195571 A1 | 10/2003 | Burnes et al. |
| 2004/0073272 A1 | 4/2004 | Knudson |
| 2005/0043644 A1 | 2/2005 | Stahmann et al. |
| 2005/0137646 A1 | 6/2005 | Wallace |
| 2005/0261600 A1 | 11/2005 | Aylsworth |
| 2006/0155206 A1 | 7/2006 | Lynn |
| 2007/0173893 A1* | 7/2007 | Pitts .................. A61N 1/3601 607/42 |
| 2009/0118610 A1 | 5/2009 | Karmarkar et al. |
| 2010/0094398 A1 | 4/2010 | Malewicz |
| 2010/0152546 A1 | 6/2010 | Behan et al. |
| 2011/0093032 A1 | 4/2011 | Boggs, II |
| 2011/0093036 A1 | 4/2011 | Mashiach |
| 2011/0112601 A1 | 5/2011 | Meadows et al. |
| 2011/0152965 A1 | 6/2011 | Mashiach |
| 2011/0172733 A1 | 7/2011 | Lima et al. |
| 2011/0172743 A1 | 7/2011 | Davis et al. |
| 2011/0213438 A1 | 9/2011 | Lima et al. |
| 2011/0230702 A1 | 9/2011 | Honour |
| 2011/0264164 A1 | 10/2011 | Christopherson |
| 2012/0029362 A1 | 2/2012 | Patangay et al. |
| 2012/0089153 A1 | 4/2012 | Christopherson |
| 2012/0192874 A1 | 8/2012 | Bolea |
| 2012/0197340 A1 | 8/2012 | Tesfayesus |
| 2013/0072999 A1 | 3/2013 | Mashiach |
| 2013/0085537 A1 | 4/2013 | Mashiach |
| 2013/0085544 A1 | 4/2013 | Mashiach |
| 2013/0085560 A1 | 4/2013 | Mashiach |
| 2014/0046221 A1 | 2/2014 | Mashiach |
| 2014/0228905 A1 | 8/2014 | Bolea |
| 2015/0029030 A1 | 1/2015 | Aoyama |
| 2015/0038865 A1 | 2/2015 | Shigeto |
| 2015/0039046 A1 | 2/2015 | Gross |
| 2015/0073232 A1 | 3/2015 | Ahmed |
| 2015/0142120 A1 | 5/2015 | Papay |
| 2015/0182753 A1 | 7/2015 | Harris |
| 2015/0224307 A1 | 8/2015 | Cyberonics |
| 2015/0273177 A1 | 10/2015 | Lizuka |
| 2015/0374991 A1 | 12/2015 | Morris et al. |
| 2016/0089540 A1 | 3/2016 | Bolea |
| 2017/0014068 A1 | 1/2017 | Gotoh et al. |
| 2017/0095667 A1 | 4/2017 | Yakovlev et al. |
| 2017/0135604 A1 | 5/2017 | Kent |
| 2017/0135629 A1 | 5/2017 | Kent |
| 2017/0143257 A1 | 5/2017 | Kent |
| 2017/0143259 A1 | 5/2017 | Kent |
| 2017/0143280 A1 | 5/2017 | Kent |

(56) References Cited

U.S. PATENT DOCUMENTS

| | | |
|---|---|---|
| 2017/0143960 A1 | 5/2017 | Kent |
| 2017/0151432 A1 | 6/2017 | Christopherson |
| 2017/0224987 A1 | 8/2017 | Kent |
| 2018/0220921 A1 | 8/2018 | Rondoni et al. |
| 2018/0221660 A1 | 8/2018 | Suri et al. |
| 2019/0001139 A1 | 1/2019 | Mishra et al. |
| 2019/0022383 A1 | 1/2019 | Hadlock |
| 2019/0057700 A1 | 2/2019 | Kent |
| 2019/0060642 A1 | 2/2019 | Boggs et al. |
| 2019/0099285 A1 | 4/2019 | Bachelder |
| 2019/0117967 A1 | 4/2019 | Scheiner |
| 2019/0374776 A1 | 12/2019 | Mishra et al. |
| 2020/0001077 A1 | 1/2020 | Kent |
| 2020/0016401 A1 | 1/2020 | Papay et al. |
| 2020/0038033 A1 | 2/2020 | Clark et al. |
| 2020/0054867 A1 | 2/2020 | Schwartz et al. |
| 2020/0054889 A1 | 2/2020 | Makansi |
| 2020/0069947 A1 | 3/2020 | Kent |
| 2020/0139138 A1 | 5/2020 | Sit |
| 2020/0316373 A1 | 10/2020 | Bolea |
| 2020/0338358 A1 | 10/2020 | Makansi |
| 2020/0346010 A1 | 11/2020 | Papay et al. |
| 2020/0346016 A1 | 11/2020 | Caparso et al. |
| 2020/0346024 A1* | 11/2020 | Caparso ............ A61N 1/36139 |
| 2020/0376261 A1 | 12/2020 | Stevens et al. |
| 2021/0106824 A1* | 4/2021 | Caparso ............. A61N 1/3611 |
| 2021/0052888 A1 | 12/2021 | Kent |
| 2022/0032052 A1 | 2/2022 | Kent et al. |
| 2022/0126103 A1 | 4/2022 | Pivonka et al. |
| 2022/0134102 A1 | 5/2022 | Kent |
| 2022/0161031 A1 | 5/2022 | O'Connor et al. |
| 2022/0218988 A1* | 7/2022 | Caparso ............ A61N 1/36135 |
| 2022/0339441 A1 | 10/2022 | Elliott |
| 2023/0321440 A1 | 10/2022 | O'Connor |
| 2022/0346666 A1 | 11/2022 | Elliott |
| 2022/0370797 A1 | 11/2022 | O'Connor |
| 2022/0409897 A1 | 12/2022 | O'Connor |
| 2023/0026728 A1 | 1/2023 | Elliott |
| 2023/0172479 A1* | 6/2023 | Verzal ............... A61N 1/36078 607/42 |
| 2023/0240715 A1 | 8/2023 | Paspa et al. |
| 2023/0302280 A1 | 9/2023 | O'Connor |
| 2023/0414945 A1* | 12/2023 | Ward ................ A61N 1/36139 |

FOREIGN PATENT DOCUMENTS

| | | |
|---|---|---|
| WO | WO-2010006218 | 1/2010 |
| WO | WO-2012027648 | 3/2012 |
| WO | WO-2013172935 | 11/2013 |
| WO | WO-2017070372 | 4/2017 |
| WO | WO-2019140404 | 7/2019 |
| WO | WO-2020181120 | 9/2020 |
| WO | WO-2021050829 | 3/2021 |
| WO | WO-2021163228 | 8/2021 |
| WO | WO-2021242633 | 12/2021 |
| WO | WO-2022058024 | 3/2022 |
| WO | WO-2022129234 | 6/2022 |
| WO | WO-2022129236 | 6/2022 |
| WO | WO-2022129247 | 6/2022 |

OTHER PUBLICATIONS

Kent et al., "Ultrasound Localization and Percutaneous Electrical Stimulation of the Hypoglossal Nerve and Ansa Cervivalis," Otolaryngology Head and Neck Surgery, 2020, 7 pages.

Weaker, Frank, "Structures of the Head and Neck," F.A. Davis, Sep. 24, 2013, p. 77.

Website: CawBing: Snore Stopper Adjustable Snore Reduction Straps Anti Apnea Snore Support Belt Jaw Sleep Band Snoring Chin Strap, https://www.walmart.com/ip/Snore-Stopper-Adjustable-Snore-Reduction-Straps-Anti-Apnea-Snore-Support-Belt-Jaw-and-Snoring-Chin-Strap/788742945, accessed Jun. 2022, 5 pages.

Website: Halo Chinstrap by Breathwear Inc., https://www.cpap.com/productpage/breathewear-halo-chinstrap, accessed Jun. 2022, 3 pages.

Benbassat et al., "The specific branches leading to the genioglossus muscle: three dimensional localisation using skin reference points," Surgical and Radiologic Anatomy, 2019, 9 pages.

Delaey et al., "Specific branches of hypoglossal nerve to genioglossus muscle as a potential target of selective neurostimulation in obstructive sleep apnea: anatomical and morphometric study," Surg Radiol Anata, 2017, 9 pages.

Gharb et al., "Microsurgical Anatomy of the Terminal Hypoglossal Nerve Relevant for Neurostimulation in Obstructive Sleep Apnea," Neuromodulation: Technology at the Neural Interface, 2015, 8 pages.

Heiser et al., "Surgical anatomy of the hypoglossal nerve: A new classification system for selective upper airway stimulation," Wiley Periodicals, Inc., wileyonlinelibrary.com/journal/hed, 2017, 10 pages.

Li et al., "Dynamic Drug-Induced Sleep Computed Tomography in Adults with Obstructive Sleep Apnea," Scientific Reports—www.nature.com/scientificreports, Oct. 2016, 8 pages.

Mu et al., "Human Tongue Neuroanatomy: Nerve Supply and Motor Endplates," National Institute of Health, 2012, 27 pages.

Pearse et al., "Review: Sleep-Disordered Breathing in Heart Failure," Imperial College London and Royal Brompton Hospital, London, United Kingdom, https://onlinelibrary.wiley.com/doi/full/10.1002/ejhf.492, published Feb. 11, 2016, 26 pages.

Vroegop et al., "Sleep endoscopy with simulation bite for prediction of oral appliance treatment outcome," Obstructive Sleep Apnea, European Sleep Research Society, 2012, 8 pages.

Wirth et al., "Hypogloassal nerve stimulation therapy does not alter tongue protrusion strength and fatigability in obstructive sleep apnea," Journal of Clinical Sleep Medicine, vol. 16, No. 2., Feb. 2020, 8 pages.

* cited by examiner

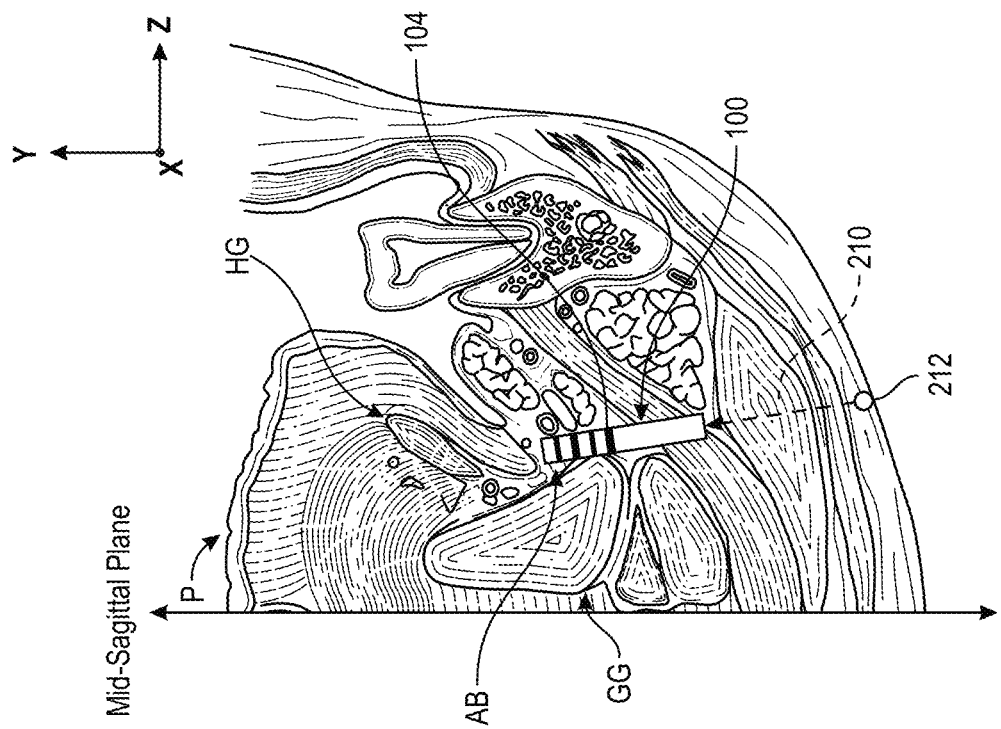
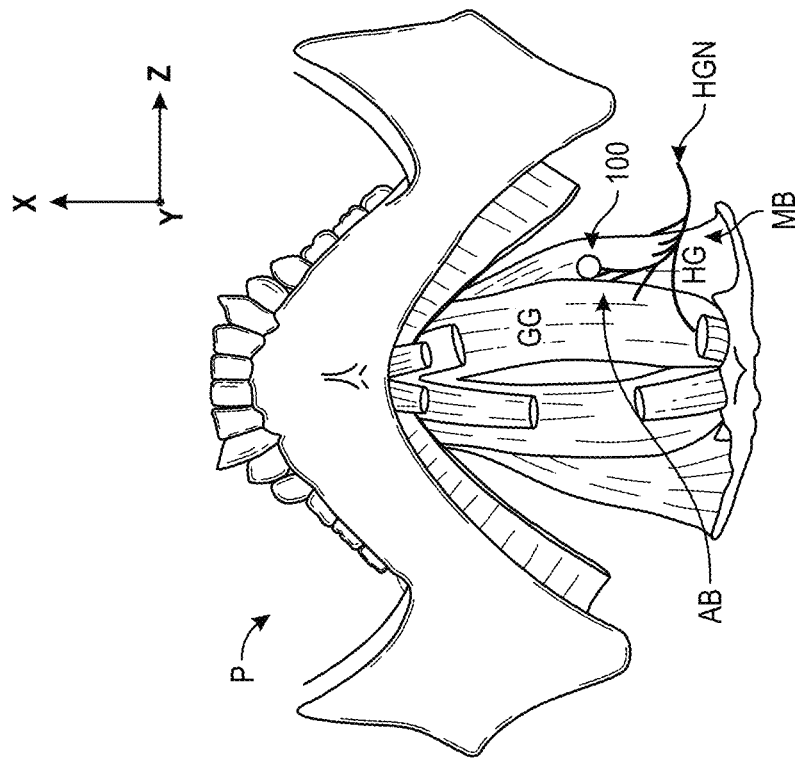
FIG. 2D
FIG. 2C

| Subject | Location Date | Approach | Observed Tongue Protrusion with Stim Met Primary Endpoint? | Electrode Array Capture & Stability During Procedure | Airway Flow Measurements Available? | Airway Flow Increase Observed during stim? | Peak Flow Amplitude Increase Stim/No Stim |
|---|---|---|---|---|---|---|---|
| 1 | Site 1 | Posterior | Yes | 1 min | No | N/A | N/A |
| 2 | Site 1 | Posterior | Yes | 1 min | No | N/A | N/A |
| 3 | Site 1 | Posterior | Yes | 1 min | Yes | Yes | >100% |
| 4 | Site 1 | Posterior | Yes | 1 min | No | N/A | N/A |
| 5 | Site 1 | Posterior | Yes | 1 min | No | N/A | N/A |
| 6 | Site 2 | Posterior | Yes | 1 min | Yes | Yes | >75% |
| 7 | Site 1 | Posterior & Intraoral | Yes | 1 min | Yes | Yes | >15% |
| 8 | Site 1 | Posterior & Intraoral | Yes | 1 min | Yes | Yes | >100% |
| 9 | Site 1 | Posterior & Intraoral | Yes | 1 min | Yes | Yes | >100% |
| 10 | Site 2 | Anterior | Yes | >5 min | Yes | Yes | >100% |
| 11 | Site 2 | Anterior | Yes | >30 min | Yes | Yes | >>100% |
| 12 | Site 1 | Anterior | Yes | >5 min | Yes | Yes | >>100% |
| 13 | Site 1 | Anterior | Yes | >5 min | Yes | Yes | >>100% |

*FIG. 13*

SIGNAL DELIVERY DEVICES TO TREAT SLEEP APNEA, AND ASSOCIATED METHODS AND SYSTEMS

CROSS-REFERENCE TO RELATED APPLICATIONS

The present application claims priority to U.S. Provisional No. 63/434,803, filed Dec. 22, 2022, and U.S. Provisional No. 63/456,752, filed Apr. 3, 2023, the entireties of which are hereby incorporated by reference herein.

TECHNICAL FIELD

The present technology is directed to signal delivery devices to treat sleep apnea, and associated methods and systems.

BACKGROUND

Obstructive sleep apnea (OSA) is a medical condition in which a patient's upper airway is occluded (partially or fully) during sleep, causing sleep arousal. Repeated occlusions of the upper airway may cause sleep fragmentation, which in turn may result in sleep deprivation, daytime tiredness, and/or malaise. More serious instances of OSA may increase the patient's risk for stroke, cardiac arrhythmias, high blood pressure, and/or other disorders.

OSA may be characterized by the tendency for soft tissues of the upper airway to collapse during sleep, thereby occluding the upper airway. OSA is typically caused by the collapse of the patient's soft palate, oropharynx, tongue, epiglottis, or combination thereof, into the upper airway, which in turn may obstruct normal breathing and/or cause arousal from sleep.

Some treatments have been available for OSA including, for example, surgery, continuous positive airway pressure (CPAP) machines, and electrical stimulation of muscles or related nerves associated with the upper airway to move the tongue (or other upper airway tissue). Surgical techniques have included procedures to remove portions of a patient's tongue and/or soft palate, and other procedures that seek to prevent the tongue from collapsing into the back of the pharynx. These surgical techniques are very invasive. CPAP machines seek to maintain upper airway patency by applying positive air pressure at the patient's nose and mouth. However, these machines are uncomfortable, cumbersome, and may have low compliance rates.

Some electrical stimulation techniques seek to prevent the tongue from collapsing into the back of the pharynx by causing the tongue to protrude forward (e.g., in an anterior direction) and/or flatten during sleep. However, existing techniques for electrically stimulating the nerves of the patient's oral cavity suffer from being too invasive and/or not sufficiently efficacious. Thus, there is a need for an improved minimally invasive treatment for OSA and other sleep disorders.

BRIEF DESCRIPTION OF THE DRAWINGS

FIGS. 2C and 2D are submental and coronal sectional views, respectively, of a portion of a patient's upper airway depicting the signal delivery device insertion path of FIG. 2A, in accordance with embodiments of the present technology.

FIG. 13 is a table including patient data obtained in response to delivering an electrical signal to target tissue, in accordance with embodiments of the present technology.

DETAILED DESCRIPTION

Figure 1A:
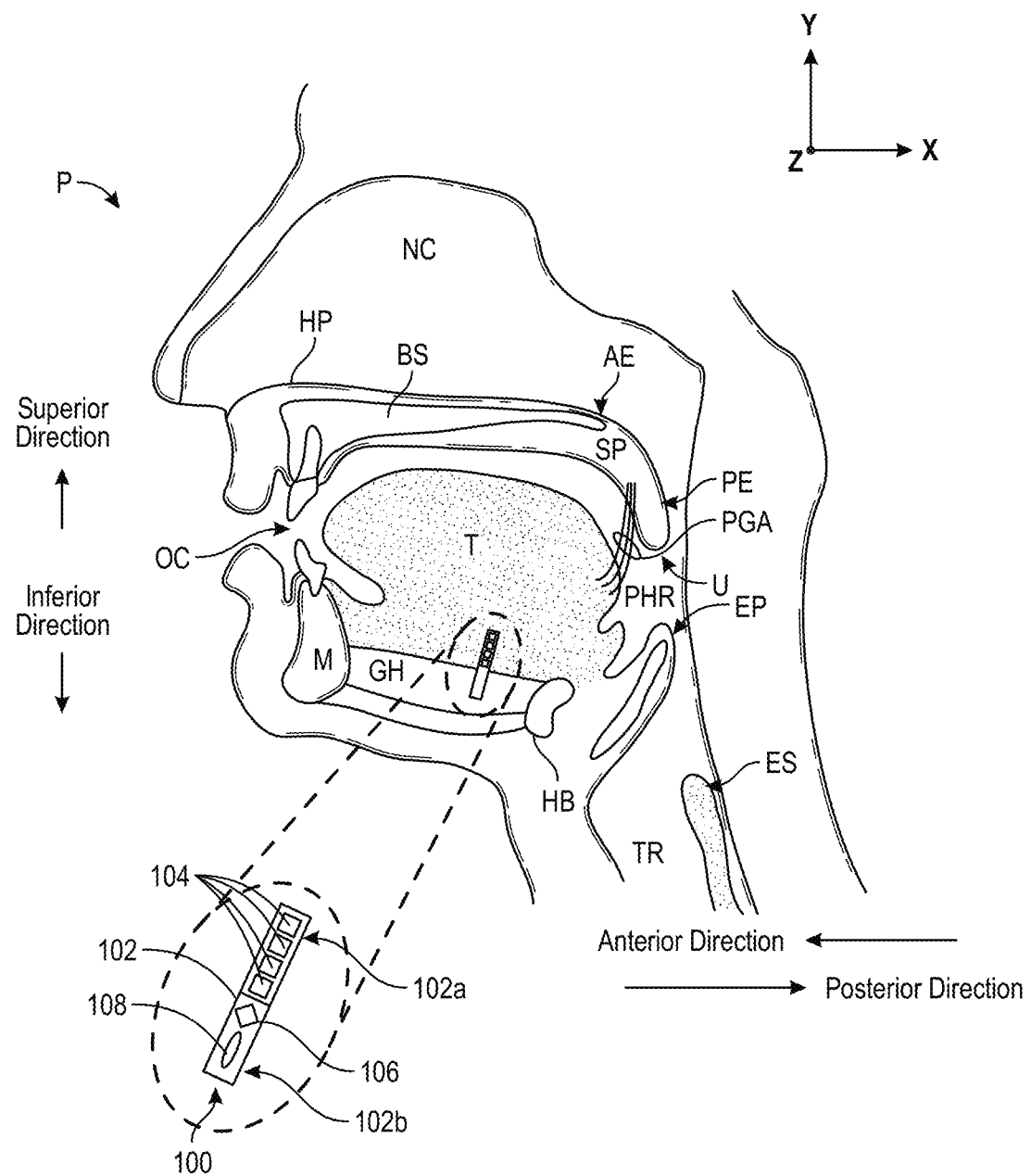
FIG. 1A is a side sectional view depicting a patient's upper airway.

The present technology is discussed under the following headings for ease of readability:
Heading 1: "Introduction"
Heading 2: "Overall Patient Physiology" (with a focus on FIGS. 1A-1D)
Heading 3: "Representative Insertion Paths and Signal Delivery Device Positions" (with a focus on FIGS. 2A-11)
Heading 4: "Representative Experimental Data" (with a focus on FIGS. 12 and 13)
Heading 5: "Additional Devices, Systems, and Methods" (with a focus on FIGS. 14-17)
Heading 6: "Examples"

While embodiments of the present technology are described under the selected headings indicated above, other embodiments of the technology can include elements discussed under multiple headings. Accordingly, the fact that an embodiment may be discussed under a particular heading does not necessarily limit that embodiment to only the elements discussed under that heading.

1. Introduction

Electrical stimulation for obstructive sleep apnea (OSA) typically includes delivering an electrical current that modulates nerves and/or muscles, e.g., to cause the tongue and/or other soft tissue to move. The electrical stimulation can accordingly remove an obstruction of the upper airway and/or prevent the tongue or other soft tissue from collapsing or obstructing the airway. As used herein, the terms "modulate" and "stimulate" are used interchangeably to mean having an effect on, e.g., an effect on a nerve and/or a muscle that in turn has an effect on one or more motor functions, e.g., a breathing-related motor function.

Representative methods and apparatuses for reducing the occurrence and/or severity of breathing disorders, such as OSA, OSA with complete concentric collapse (CCC), central sleep apnea, and/or the like, are disclosed herein. In accordance with representative embodiments, a minimally invasive signal delivery device is implanted proximate to or adjacent to one or more tissues of the patient's upper airway, such as one or more nerves that innervate the patient's oral cavity, soft palate, oropharynx, and/or epiglottis. Representative nerves include the hypoglossal nerve, branches of the ansa cervicalis, and/or the vagal nerves, which are located adjacent to and/or around the oral cavity or in the neck. The signal delivery device can be implanted in the patient via a percutaneous injection, intravenously (via, e.g., the lingual artery, the lingual vein, or other suitable vasculature), invasively (via, e.g., one or more incisions formed intraorally, sublingually, submandibularly, or by drilling an access hole, e.g., through the patient's mandible), via combinations thereof, and/or using other suitable implantation techniques. In a preferred embodiment, the signal delivery device is implanted percutaneously and/or non-invasively, e.g., without drilling access holes and/or forming incisions in the patient. A non-implanted power source, e.g., including one or more mouthpiece portions, collar portions, chinstrap portions, pillow portions, mattress overlay portions, other suitable "wearables," and/or one or more adhesive, skin-mounted devices, can wirelessly provide electrical power to the implanted signal delivery device. The signal delivery device emits accurately targeted electrical signals (e.g., pulses) that improve the patient's upper airway patency and/or improve the tone of the tissue of the intraoral cavity to treat sleep apnea. The electrical current delivered by the signal delivery device can stimulate at least a portion of a patient's hypoglossal nerve and/or other nerves associated with the upper airway. By moving the tongue forward and/or by preventing the tongue and/or soft tissue from collapsing onto the back of the patient's pharynx and/or into the upper airway, the devices and associated methods disclosed herein can in turn improve the patient's sleep, e.g., by moving the potentially obstructing tissue in the upper airway/pharynx. More specifically, applying the electrical signal to one or more portions of the hypoglossal nerve anterior from the medial branch of the hypoglossal nerve and/or directly to one or both of the patient's genioglossus muscles can cause the tongue to move forward/anteriorly (e.g., a net positive protrusive response), downwardly/inferiorly/caudally, and/or can otherwise at least partially or fully prevent the tongue from collapsing onto the back of the patient's pharynx and/or into the upper airway.

Many embodiments of the technology described below may take the form of computer-, machine-, or controller-executable instructions, including routines executed by a programmable computer or controller. Those skilled in the relevant art will appreciate that the technology can be practiced on computer/controller systems other than those shown and described below. The technology can be embodied in a special-purpose computer, controller, or data processor that is specifically programmed, configured, or constructed to perform one or more of the computer-executable instructions described below. Accordingly, the terms "computer" and "controller" as generally used herein refer to any suitable data processor and can include Internet appliances and hand-held devices (including palm-top computers, wearable computers, tablets, cellular or mobile phones, multi-processor systems, processor-based or programmable consumer electronics, network computers, minicomputers, and the like). Information handled by these computers can be presented at any suitable display medium, including a liquid crystal display (LCD). Manufacturers can also program devices of the disclosed systems to carry out at least some of these methods.

The present technology can also be practiced in distributed environments, where tasks or modules are performed by remote processing devices that are linked through a communications network. In a distributed computing environment, program modules or subroutines may be located in local and remote memory storage devices. Aspects of the technology described below may be stored or distributed on any suitable computer-readable media, including one or more application-specific integrated circuits (ASICs) (e.g., with addressable memory), as well as distributed electronically over networks. Data structures and transmissions of data particular to aspects of the technology are also encompassed within the scope of the embodiments of the technology.

2. Overall Patient Physiology

Representative embodiments described herein include signal delivery devices having electrodes that can be positioned to deliver one or more electrical currents to one or more specific target locations, e.g., specific nerves and/or specific positions along a nerve. FIG. 1A illustrates the general anatomy of the patient's oral cavity. Such locations include locations along the patient's hypoglossal nerve, branches of the ansa cervicalis, and/or vagal nerves, as well as those nerves that innervate muscles of the airway (e.g., palatal, oropharyngeal, laryngeal, omohyoid, sternohyoid, and/or sternothyroid muscles) besides the tongue. The target location can be identified with respect to any of, or any combination of, intrinsic or extrinsic muscles, associated nerve branches and/or portions thereof, and/or other physiological features. Such a target location and/or position can also be distal from the salivary glands (e.g., medial to the sublingual salivary gland) and/or other structures to reduce or prevent patient discomfort and/or other undesired effects.

FIG. 1A illustrates a patient P relative to a coordinate system in which the x-axis denotes the anterior-posterior directions, the y-axis denotes the superior-inferior and/or cranial-caudal directions, and the z-axis denotes the medial-lateral directions. The patient P has a hard palate HP which overlies the tongue T and forms the roof of the oral cavity OC (e.g., the mouth). The hard palate HP includes bone support BS, and thus does not typically deform during breathing. The soft palate SP, which is made of soft tissue such as membranes, fibrous material, fatty tissue, and muscle tissue, extends rearward (e.g., in a posterior direction) from the hard palate HP toward the back of the pharynx PHR. More specifically, an anterior end AE of the soft palate SP is anchored to a posterior end of the hard palate HP, and a posterior end PE of the soft palate SP is unattached. Because the soft palate SP does not contain bone or hard cartilage, the soft palate SP is flexible and may collapse onto the back of the pharynx PHR and/or flap back and forth (e.g., especially during sleep). The collapse of these and/or other tissues of the patient P (e.g., the tongue T) can cause a corresponding collapse of the patient's airway which, in turn, can cause obstructive sleep apnea and/or other breathing disorders.

The pharynx PHR, which passes air from the oral cavity OC and the nasal cavity NC into the trachea TR, is the part of the throat situated inferior to (below) the nasal cavity NC, posterior to (behind) the oral cavity OC, and superior to (above) the esophagus ES. The pharynx PHR is separated from the oral cavity OC by the palatoglossal arch PGA, which runs downward on either side to the base of the tongue T. Although not shown for simplicity, the pharynx PHR includes the nasopharynx, the oropharynx, and the laryngopharynx. The nasopharynx lies between an upper surface of the soft palate SP and the wall of the throat (i.e., superior to the oral cavity OC). The oropharynx lies behind the oral cavity OC and extends from the uvula U to the level of the hyoid bone HB. The oropharynx opens anteriorly into the oral cavity OC. The lateral wall of the oropharynx includes the palatine tonsil and lies between the palatoglossal arch PGA and the palatopharyngeal arch. The anterior wall of the oropharynx includes the base of the tongue T and the epiglottic vallecula. The superior wall of the oropharynx includes the inferior surface of the soft palate SP and the uvula U. Because both food and air pass through the pharynx PHR, a flap of connective tissue called the epiglottis EP closes over the glottis (not shown for simplicity) when food is swallowed, to prevent aspiration. The laryngopharynx is the part of the throat that connects to the esophagus ES, and lies inferior to the epiglottis EP. Below the tongue T is the lower jaw or mandible M, and the geniohyoid muscle GH, which is one of the muscles that controls the movement of the tongue T. The genioglossus muscle, which also controls tongue movement, and is a particular target of the presently disclosed therapy, is discussed later with reference to FIG. 1B.

A signal delivery device 100 (shown schematically) can be positioned at least proximate to or within one or more target neural and/or muscle structures, and includes a housing 102, one or more electrodes 104, a signal generator 106, and an antenna and/or coil 108. The housing 102 can include a first end portion 102a and a second end portion 102b opposite the first end portion 102a. In some embodiments, the housing 102 has a length of at least 0.5 cm, 1 cm, 1.5 cm, or 2 cm, such as a length of 1.6 cm. In some embodiments, the housing 102 has a width/diameter of at least 1 mm, 2 mm, 3 mm, 4 mm, 5 mm, or 6 mm. The housing 102 can be configured to hermetically contain one or more circuit components of the signal delivery device 100, including the signal generator 106 and/or the antenna 108. All or a portion of the housing 102 can be formed from platinum (Pt), platinum and iridium (PtIr), Ti6AL4V, epoxy, a thermoplastic elastomer (TPE), one or more ceramics, and/or one or more other suitable materials. For example, a portion of the housing 102 surrounding the antenna 108 can be formed from epoxy, ceramic, and/or TPE, e.g., to prevent, or at least partially prevent, interference with power transmission to the antenna 108. Optionally, at least a portion of the housing 102 can be electrically activatable and configured to serve as an electrode. As described in further detail below, signal delivery devices having the foregoing characteristics can be minimally invasive, while also providing targeted stimulation to a variety of candidate stimulation sites.

The signal delivery device 100 can be leadless with individual ones of the electrodes 104 positioned on and/or at least partially around the housing 102, e.g., the first end portion 102a of the housing 102. In some embodiments, individual ones of the electrodes 104 can be carried by a lead or flexible component coupled to the housing 102. In these and/or other embodiments, individual ones of the electrodes 104 can be masked (e.g., circumferentially masked), segmented (e.g., circumferentially segmented, individually addressable), directional, at least partially covered, and/or otherwise configured to direct the electrical field in a specific direction or directions. The electrodes 104 can be formed from Pt and/or Jr, such as Pt90/Ir10, and/or one or more other suitable materials. Individual ones of the electrodes 104 can have a length (e.g., as measured parallel to a longitudinal axis of the housing 102) of up to 0.1 mm, 0.2 mm, 0.25 mm, 0.5 mm, 0.75 mm, 1 mm, or 2 mm, such as a length of 1.5 mm or another suitable length. Additionally, or alternatively, individual ones of the electrodes 104 can be spaced apart from one another (e.g., as measured center-to-center or end-to-end) by a distance of up to 1 mm, 2 mm, 3 mm, 4 mm, 5 mm, 10 mm, 15 mm, or 20 mm, such as a distance of 3.5 mm, 12 mm, or another suitable distance. In the illustrated embodiment, the signal generator 106 and the antenna 108 are positioned at least partially or fully within the housing 102, e.g., the second end portion 102b of the housing 102. In other embodiments, the signal generator 106, the antenna 108, and/or other components of the signal delivery device 100 can be contained within a separate housing positioned elsewhere, e.g., subcutaneously within the patient P. The signal delivery device 100 can be secured in position at least proximate to or within the one or more target neural and/or muscle structures using one or more anchors, suture threads, and/or other suitable devices. For example, the signal delivery device can be deployed internally within the patient or at least partially external to the patient via, e.g., a patch, pad, or other wearable.

In the illustrated embodiment, the signal delivery device 100 includes four electrodes 104 arranged in a 1×4 array. In other embodiments, the signal delivery device 100 can include more or fewer electrodes 104 and/or electrodes arranged in other suitable patterns. For example, the signal delivery device 100 can include at least 2, 3, 6, 8, 10, or more electrodes, individual ones of which can be arranged within one or more rows and/or one or more columns. Accordingly, in at least some embodiments, the signal delivery device 100 includes electrodes 104 arranged in a 2×4 array, a 3×3 array, a 4×4 array, a 2×6 array, etc. An increased number of electrodes can improve the degree to which energy can be targeted toward individual locations/tissues within the patient. In some embodiments, the electrodes 104 can include one or more paddle electrodes, flexible (e.g., foil) electrodes, planar microelectrodes, monopole electrodes, an Injectrode®, and/or other suitable electrodes.

In operation, the antenna and/or coil 108 can be configured to wirelessly receive power (e.g., radiofrequency (RF) power, inductive power, etc.) from one or more devices external to the patient P, such as one or more wearable devices. In some embodiments, the wireless power signal (e.g., an RF power signal), or at least a portion of the wireless power signal, can have a frequency in a range of from about 300 MHz to about 6 GHz, e.g., from about 400 MHz to about 2.5 GHz, from about 600 MHz to about 2.45 GHz, from about 900 MHz to about 1.2 GHz, or any other intermediate frequency or frequency range. In some embodiments, the wireless power signal (e.g., an inductive power signal), or at least a portion of the wireless power signal, can have a frequency in a range of from about 100 kHz to about 14 MHz, including, e.g., about 135.7 kHz, about 6.5 MHz, about 13.5 MHz, and/or another suitable frequency and/or range of frequencies. In these and/or other embodiments, the wireless power signal, or at least a portion of the wireless power signal, can have a frequency or frequency range in the industrial, scientific, and medical band ("ISM band") of frequencies.

The power received at the antenna 108 can be transmitted to the signal generator 106, which can use the power to generate one or more electrical pulses or signals. In at least some embodiments, the power (e.g., AC power) received at the antenna 108 is rectified to DC (via, e.g., an AC-DC converter), then transmitted to a DC-DC converter, charge pump, and/or transformer, and converted to pulses having a frequency in a range from about 10 Hz to about 500 Hz, such as from about 30 Hz to about 300 Hz, or a frequency in a lower range, for example, between about 1 Hz and about 10 Hz. In other embodiments, the pulses can be delivered at a higher frequency (e.g., 10 kHz or more) and/or in the form of bursts. The amplitude of the signal can be from about 1 mV to about 5 V (and in particular embodiments, 1 V to 2 V) in a voltage-controlled system, or from about 0.5 mA to about 12 mA in a current-controlled system, or from about 1.5 mA to about 3.5 mA. In the illustrated embodiment, all the signal generation functions are performed by the signal generator 106, and in other embodiments, some or all signal generation functions may be performed by external elements. In at least some embodiments, for example, the signal delivery device 100 is passive (e.g., does not include the signal generator 106), and is configured to receive one or more signals via the antenna 108 so as to apply the one or more signals to the patient via the electrodes 104. In such embodiments, the antenna 108 can be configured to receive the signals via inductive power transfer and/or via another suitable power transmission technique. The signal generation functions and signal delivery functions may be performed by a single implantable device, or by multiple devices.

The signals generated by the signal generator 106 can be transmitted to one or more of the electrodes 104, which can in turn deliver the signals to the target neural and/or muscle structures. The electrical field(s) resulting from the currents transmitted by the electrodes 104 produces the desired effect (e.g., excitation and/or inhibition) at the target nerve. In at least some embodiments, the signal delivery device 100 need not include any onboard power storage elements (e.g., power capacitors and/or batteries), or any power storage elements having a storage capacity greater than 0.5 seconds, so as to reduce system volume. In other embodiments, the signal delivery device 100 can include one or more small charge storage devices (e.g., low voltage, high capacitance capacitors, solid state batteries, and/or the like) that are compatible with the overall compact shape of the signal delivery device 100 and have a total charge storage capacity of no more than 1 second, 5 seconds, 10 seconds, 15 seconds, 20 seconds, 25 seconds, 30 seconds, 1 minute, 2 minutes, 5 minutes, any time period therebetween, or another suitable time period, depending on the embodiment. In at least some embodiments, the electrical signal delivered to the patient can be delivered via a bipole formed by two of the electrodes 104. In other embodiments, the signal can be a monopolar signal, with at least a portion of the housing 102 (e.g., the first end portion 102a of the housing 102) forming a ground or return electrode. In these and other embodiments, the waveform includes a biphasic, charge balanced waveform.

In some embodiments, the antenna 108 (or another communication component of the signal delivery device 100) can be configured to wirelessly receive instructions and direct the instructions to the signal generator 106 for generating the electrical signals, e.g., in addition to wirelessly receiving power. The instructions can include one or more signal delivery parameters of the electrical signal, such as a frequency, amplitude, pulse width, duty cycle, duration, etc.; a stimulation energy of the electrical signal; commands to deliver the electrical signal via individual ones of the electrodes 104; an ON time during which the signal generator is active; an OFF time during which the signal generator is inactive; and/or other suitable instructions. The instructions can be provided by the same device that wirelessly provides power to the signal delivery device 100, or by another device, e.g., another external device, such as an external controller. Depending on the embodiment, instructions can be carried by one or more computer- or machine-readable media housed in an implantable element, an external (e.g., wearable) element or other controller, or any suitable combination of the foregoing devices. Additional details regarding devices for providing power and/or instructions to implanted signal delivery devices can be found in U.S. Pat. Publication No. 2022/0161031, filed Feb. 7, 2022, and titled "IMPLANTABLE ELECTRODES WITH REMOTE POWER DELIVERY FOR TREATING SLEEP APNEA, AND ASSOCIATED SYSTEMS AND METHODS" and U.S. application Ser. No. 17/851,718, filed Jun. 28, 2022, and titled "WEARABLE DEVICES FOR TREATING SLEEP APNEA, AND ASSOCIATED SYSTEMS AND METHODS," the entireties of which are hereby incorporated by reference.

Figure 1B:
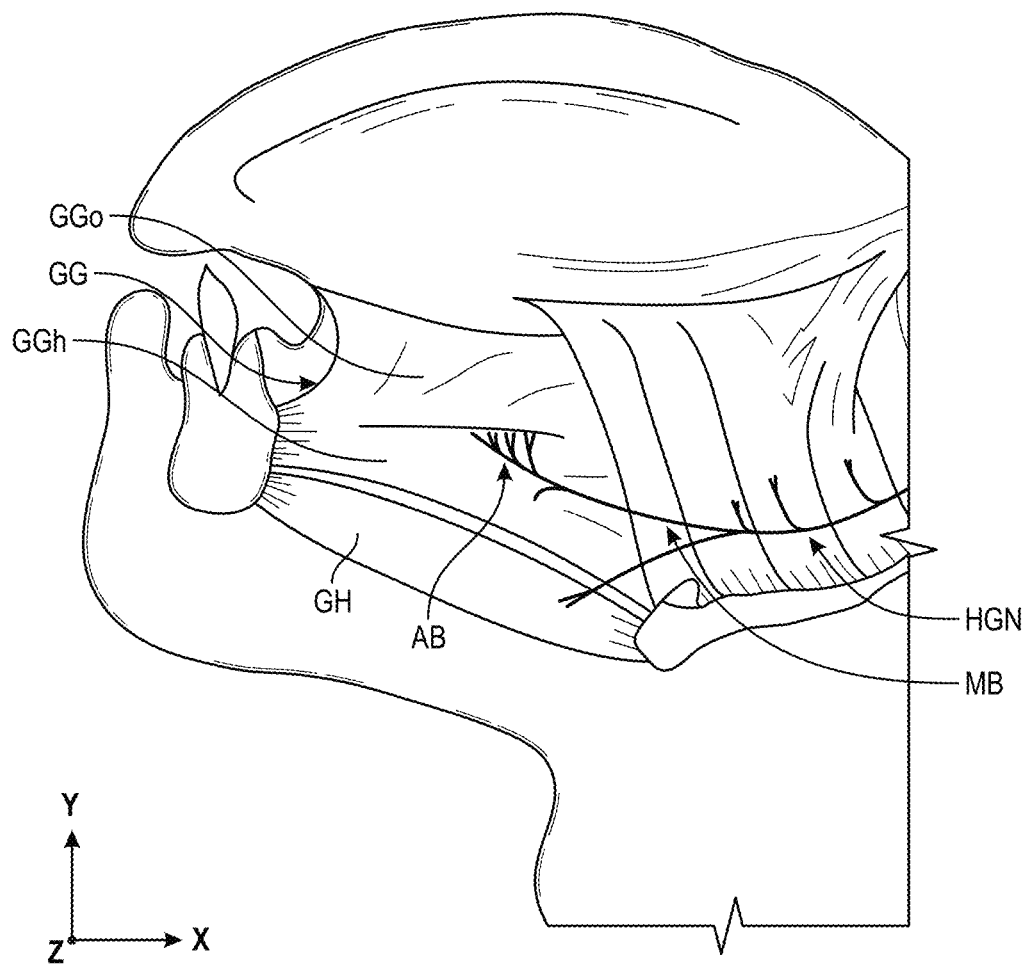
FIG. 1B is a side sectional view depicting a portion of a patient's genioglossus muscle and hypoglossal nerve.
Figure 1C:
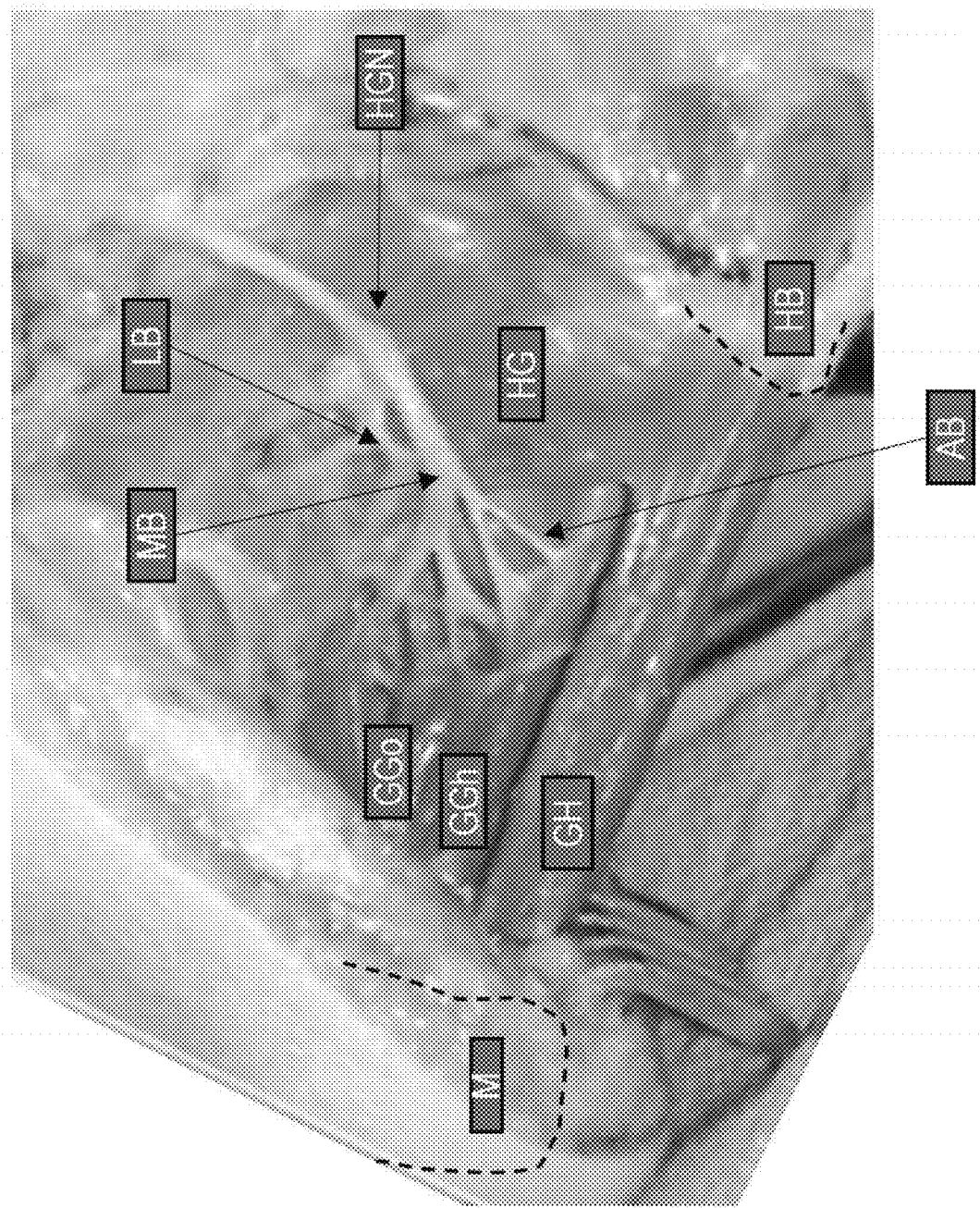
FIG. 1C is a side dissection view depicting a portion of a patient's genioglossus muscle and hypoglossal nerve.

FIG. 1B is a partially schematic illustration of representative neural structures and musculature of the patient's upper airway. FIG. 1C is a side dissection view of neural structures and musculature of the patient's upper airway. Referring to FIGS. 1B and 1C together, representative musculature includes the geniohyoid muscle GH, which extends between the patient's mandible M and the hyoid bone HB, and the genioglossus muscle GG, which includes an oblique fiber portion GGo and a horizontal fiber portion GGh. The associated neural structures include at least a portion of one or both of the patient's hypoglossal nerves HGN that innervate the tongue, including the medial branch MB of the hypoglossal nerve HGN and/or one or more anterior portions or branches of the hypoglossal nerve HGN ("anterior branches AB"). The anterior branches AB may include the distal arborizing portions of the hypoglossal nerve HGN, such as the motor points, motor end plates, and/or neuromuscular junctions of the hypoglossal nerve HGN as it inserts into the genioglossus muscle GG. In some patients, one or more of the anterior branches AB may include a plurality of distal brachiated portions DB (more clearly visible in FIG. 1D) that innervate the genioglossus muscle GG. The lateral branch LB of the hypoglossal nerve HGN and the hyoglossus muscle HG are shown for context. By positioning and activating minimally invasive electrodes positioned proximate to the foregoing neural structures and/or associated musculature, embodiments of the present technology can control, reduce, and/or eliminate the effects of OSA.

Figure 1D:
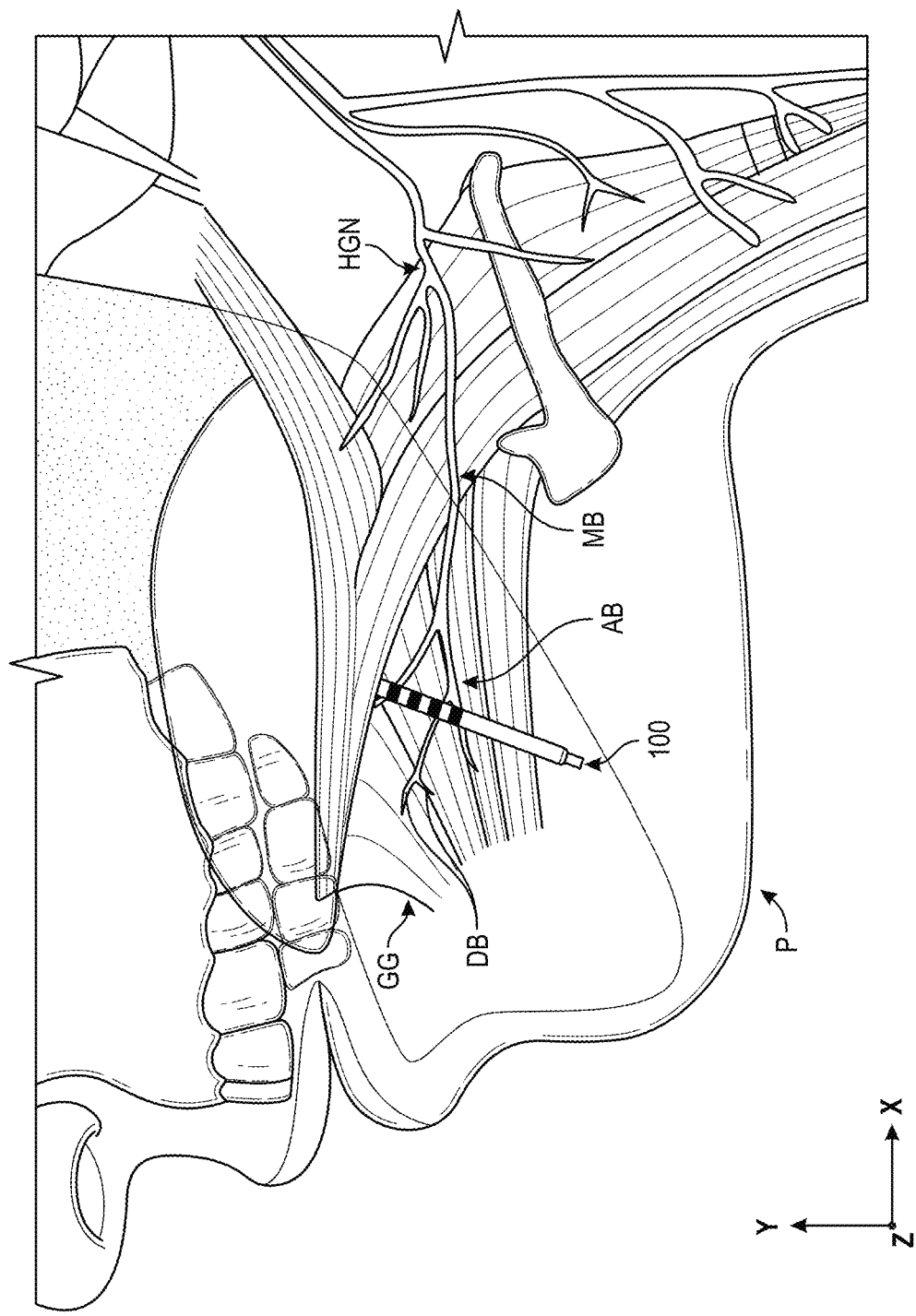
FIG. 1D is a side view depicting a portion of a patient's upper airway and a signal delivery device positioned in accordance with embodiments of the present technology.

FIG. 1D is a side view depicting a portion of a patient's upper airway and the signal delivery device 100 positioned in accordance with embodiments of the present technology. In FIG. 1D, the signal delivery device 100 is positioned to deliver an electrical signal to one or more of the anterior branches AB of the hypoglossal nerve HGN and/or one or more of the distal brachiated portions DB of the anterior branches AB. Although the hypoglossal nerve HGN of the patient P illustrated in FIG. 1D includes three anterior branches AB total and one anterior branch AB with two distal brachiated portions DB, a person of ordinary skill in the art will appreciate that the hypoglossal nerves HGN of other patients can have more or fewer anterior branches AB, more or fewer anterior branches AB with distal brachiated portions DB, and/or more or fewer distal brachiated portions DB per individual anterior branch AB. Additionally, or alternatively, one or more other signal delivery devices can be positioned to deliver an electrical signal to another portion of the hypoglossal nerve, such as the medial branch MB, another nerve, such as the C1 nerve, and/or positioned to deliver an electrical signal directly to the genioglossus muscle GG. Additional details regarding signal delivery device positioning are described below with reference to FIGS. 2A-10.

3. Representative Insertion Paths and Signal Delivery Device Positions

Several stimulation targets and implantation techniques are described and/or illustrated with reference to FIGS. 2A-11. For the purpose of illustrative clarity, these stimulation targets and implantation techniques are shown with reference to a left or right side of the patient P's anatomy, for example, a first portion of a left hypoglossal nerve of the patient P. It will be appreciated, however, that at least some or all of the stimulation targets and/or implantation techniques described and/or illustrated with reference to FIGS. 2A-11 are equally suitable for application to another side of the patient's anatomy, for example, a second portion of a right hypoglossal nerve of the patient P. Additionally, at least some of the stimulation targets and/or implantation techniques can be used for bilateral signal delivery, for example, to apply a first electrical signal to a first stimulation target on a first side of the patient P at a first time, and to apply a second electrical signal to a second stimulation target on a second side of the patient P opposite the first side at the same or a different time. In some embodiments, the first and second stimulation targets can be corresponding left and right portions of the patient's anatomy, such as the first and second portions of the left and right hypoglossal nerves. In other embodiments, the first and second stimulation targets can be different, such as a first portion of the left hypoglossal nerve and a second portion of a genioglossus muscle of the patient.

Figure 2A:
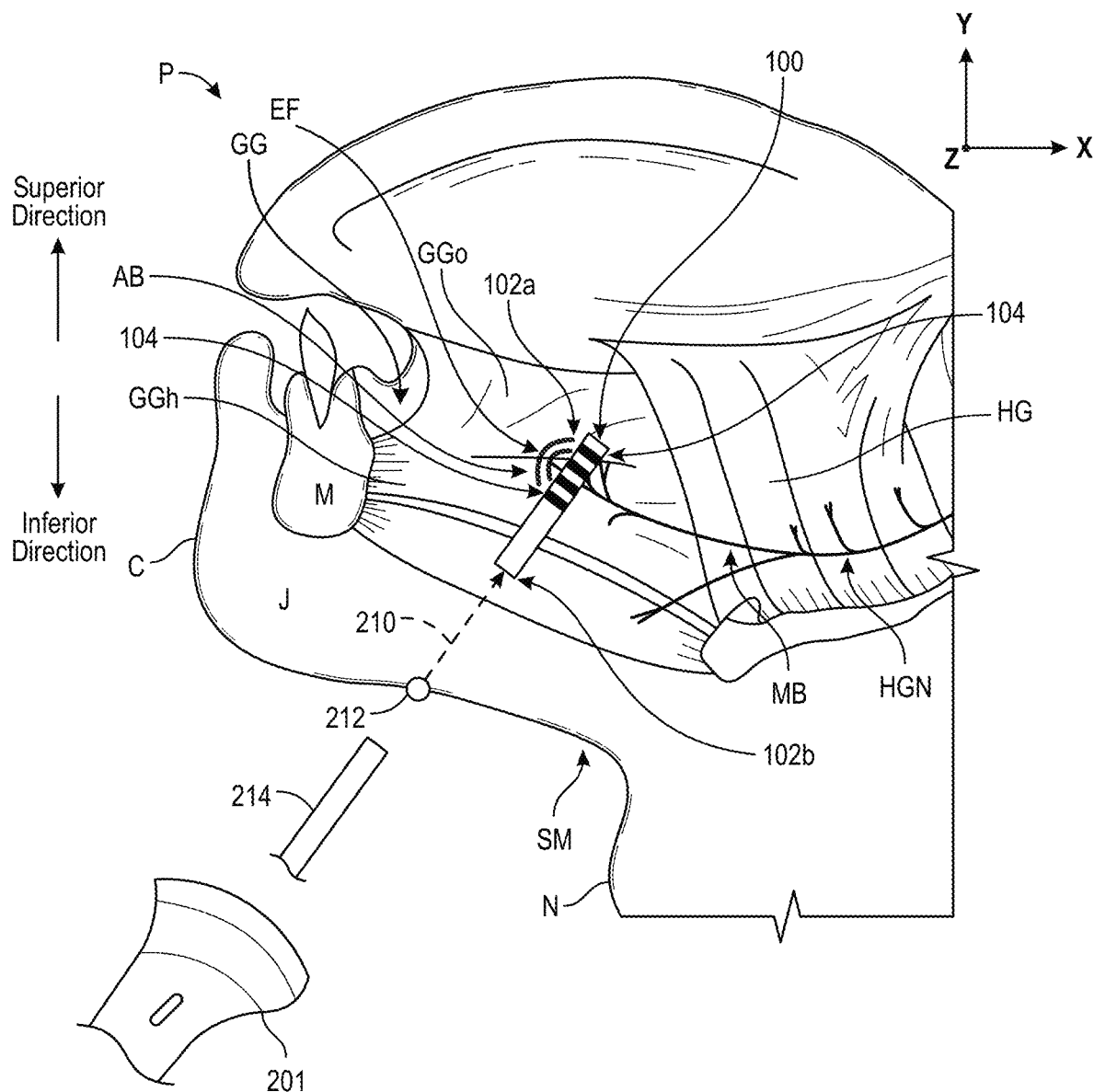
FIG. 2A is a side view of a portion of a patient's upper airway depicting a signal delivery device insertion path, in accordance with embodiments of the present technology.

FIG. 2A is a side sectional view of a portion of a patient's upper airway depicting the signal delivery device 100 in a position at least proximate to a target location, in accordance with embodiments of the present technology. In the illustrated embodiment, the target location includes one or more of the anterior branches AB of the hypoglossal nerve HGN. For example, the target location can be between about 10 mm and about 0.01 mm from one or more of the anterior branches AB, such as within up to 9 mm, 8 mm, 7 mm, 6 mm, 5 mm, 4 mm, 3 mm, 2 mm, 1 mm, or 0.1 mm from one or more of the anterior branches AB, within any distance therebetween, or within another suitable distance from one or more of the anterior branches AB.

Some sleep apnea treatments include stimulating the medial branch MB of the hypoglossal nerve HGN to cause a protrusive response in the patient's tongue T. However, the medial branch MB may also innervate retrusive muscle fibers or "retrusers" (e.g., the styloglossus and the hyoglossus muscles) that, when activated, can cause a retrusive response that may equal or exceed the protrusive response. The retrusive response can reduce or prevent effective sleep apnea treatment. In contrast to methods targeting the medial branch MB of the hypoglossal nerve HGN, methods of the present technology can target one or more of the anterior branches AB of the hypoglossal nerve HGN. This approach is expected to reduce or prevent retruser stimulation, produce a net positive protrusive response (e.g., a protrusive response greater than the retrusive response), and/or improve (e.g., increase) airflow through the patient's upper airway and/or oral cavity. In at least some embodiments, the patient's airflow can be improved without or generally without producing a protrusive response of the patient's tongue and/or genioglossus muscles GG.

Without being bound by theory, delivering the electrical signal to one or more of the anterior branches AB is expected to cause little to no stimulation of some or all retrusive branches of the hypoglossal nerve HGN at least because the anterior branches AB of the hypoglossal nerve HGN are anterior/downstream from the retrusive branches. When the signal delivery device 100 is positioned to deliver the electrical signal to one or more of the anterior branches AB, there can be a significant gap (e.g., about 1 cm or more) between the electrodes 104 and the retrusive muscles and/or the retrusive branches of the hypoglossal nerve HGN. In these and other embodiments, the target location can include one or more other portions of the hypoglossal nerve HGN (e.g., the medial branch MB), the genioglossus muscle GG (e.g., the horizontal fiber portion GGh and/or the oblique fiber portion GGo), and/or another suitable tissue within the patient's oral cavity. As described in greater detail below, applying the electrical signal to the anterior branches AB is expected to allow independent and/or selective control over which of the anterior branches AB receive the electrical signal in order to, e.g., (i) increase or maximize airflow through the patient's upper airway, (ii) reduce or minimize power consumption, (iii) cause a select subset of genioglossus muscle GG fibers to contract, and/or (iv) improve patient comfort.

The signal delivery device 100 can be positioned at least proximate to the target location via an insertion path 210 extending from the submental region SM of the patient P, such as from an underside of the patient's jaw J and/or between the patient's chin C and neck N, in an at least partially upward or superior direction toward the target location. The insertion path 210 can be used to position the signal delivery device 100 in an orientation such that at least a component (e.g., a vector component) of the orientation is aligned along an inferior-superior/cranial-caudal axis. In other words, the signal delivery device 100 is not aligned solely along the x-axis. Instead, a vector component of the orientation (e.g., a significant vector component) is aligned along the y-axis. For example, as illustrated in FIG. 2A, the first end portion 102a of the signal delivery device 100 is positioned superior to the second end portion 102b of the signal delivery device 100. When the signal delivery device 100 is in this orientation, one or more of the electrodes 104 can be positioned to deliver the signal to target tissue at or at least proximate to one or more of the anterior branches AB, which can cause a protrusive movement of the patient's tongue T.

Figure 2B:
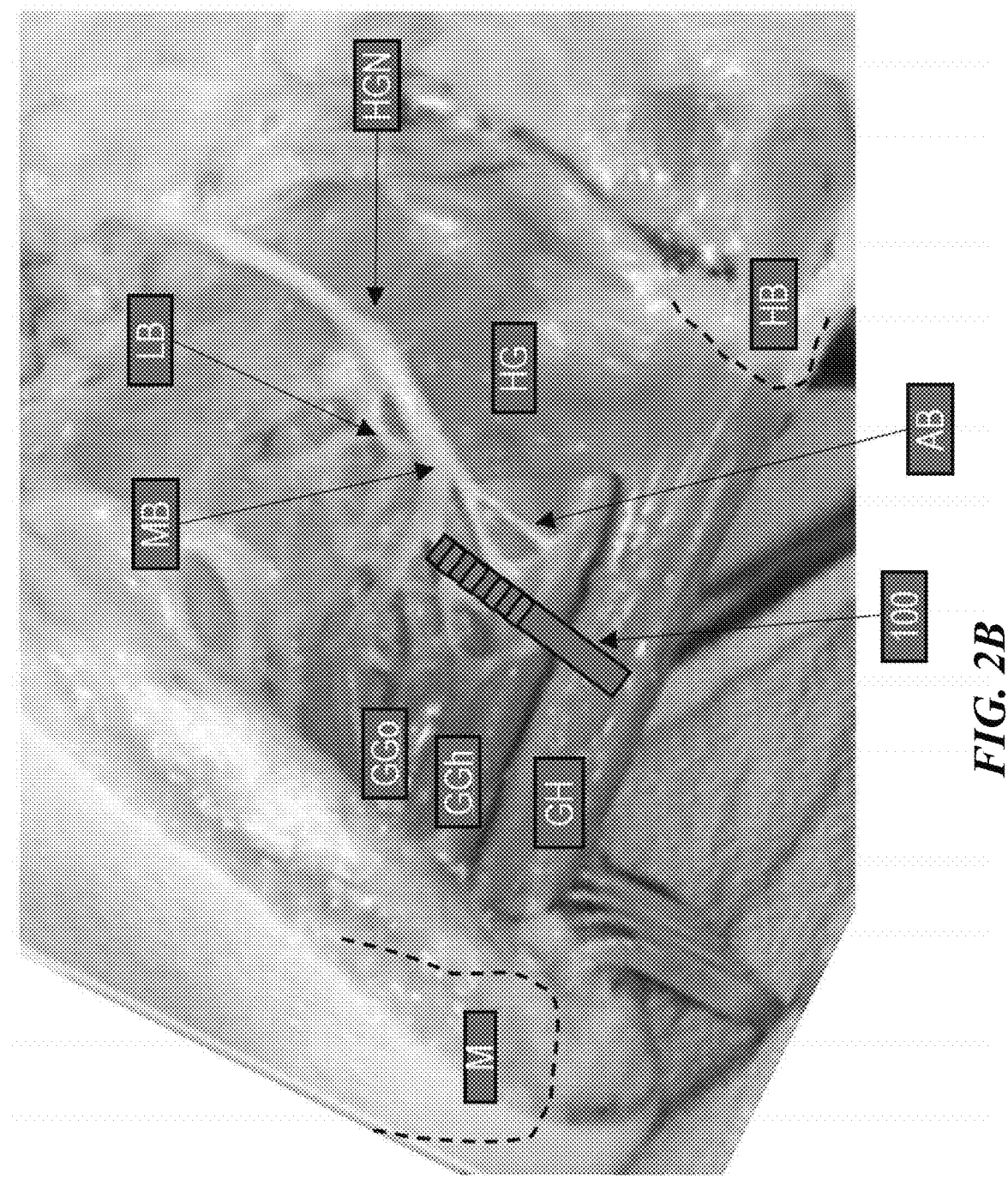
FIG. 2B is a side dissection view depicting an implanted orientation of a signal delivery device after insertion along the signal delivery device insertion path of FIG. 2A, in accordance with embodiments of the present technology.

FIG. 2B is a side dissection view depicting an implanted orientation of a signal delivery device after insertion along the signal delivery device insertion path of FIG. 2A between the patient's mandible M and hyoid bone HB, in accordance with embodiments of the present technology. Referring to FIGS. 2A and 2B together, when viewed in a direction perpendicular to a mid-sagittal or median plane of the patient P, the signal delivery device 100 can be positioned such that at least a portion of the signal delivery device 100 (e.g., the first end portion 102a and/or one or more of the electrodes 104, identified in FIG. 2A) bisects and/or is positioned between a first point or end at which individual ones of the anterior branches AB innervate the genioglossus muscle GG (e.g., the oblique fiber portion GGo and/or the horizontal fiber portion GGh), and a second point or end at which individual ones of the anterior branches AB divide from the medial branch MB. The lateral branch LB of the hypoglossal nerve HGN is shown for context. This position/orientation of the signal delivery device 100 is expected to produce increased control over the patient's response to the electrical signal. For example, as shown in FIG. 2A, one or more of the electrodes 104 of the signal delivery device 100 can be aligned transverse to a plurality of the anterior branches AB. As such, the electrodes 104 can be positioned to deliver the electrical signal to at least two, three, four, or more of the anterior branches AB. Accordingly, an electrical field EF generated between individual ones of the electrodes 104 can include field lines that extend transverse, or at least generally transverse, to one or more of the anterior branches AB.

In at least some embodiments, the signal delivery device 100 can be configured to selectively direct the electrical signal toward one or more of the anterior branches, e.g., to control which of the anterior branches AB (e.g., all or a subset) receive the electrical signal and/or which brachiated portions of individual anterior branches AB receive the electrical signal. This spatial control of the electrical signal is expected to allow the delivered signal to cause individual muscular compartments of the oblique fiber portion GGo and/or the horizontal fiber portion GGh of the genioglossus muscle GG to contract independently and/or selectively. This is described in greater detail below with reference to FIGS. 5A-5E. Additionally, or alternatively, spatial control over delivery of the electrical signal is expected to allow a strength of the genioglossus muscle GG contraction to be adjustable based, at least in part, on the number and/or location of the anterior branches AB and/or distal brachiated portions DB thereof that receive the electrical signal. More specifically, when the oblique fiber portion GGo of the genioglossus muscle GG contracts, this contraction pulls the top/back of the tongue T near the palate inwardly toward the chin C. In addition, the horizontal fiber portion GGh of the genioglossus muscle GG pulls the base of the tongue (e.g., near the hyoid bone HB) toward the chin C.

Embodiments of the present technology can independently and/or selectively deliver electrical signals to individual ones of the muscular compartments in one (e.g., only one) or both of the oblique fiber portion GGo and/or the horizontal fiber portion GGh to cause the genioglossus muscle GG to contract. However, because the medial branch MB innervates all of the anterior branches AB, delivering electrical signals to the medial branch MB leads to stimulation of all the anterior branches AB (e.g., including any/all of the distal brachiated portions DB thereof) and any/all of the muscles innervated thereby, including both the oblique fiber portion GGo and the horizontal fiber portion GGh of the genioglossus muscle GG. As a result, it is difficult, if not impossible, to selectively activate individual anterior branches AB, their distal brachiated portions DB, and/or the muscles innervated thereby when delivering electrical signals to the medial branch MB. Additionally, or alternatively, positioning the signal delivery device 100 in an inferior-superior orientation is expected to allow the signal delivery device 100 to move at a rate and/or in a direction that is at least generally similar or identical to the rate and/or the direction the surrounding tissue moves. This can reduce, minimize, and/or prevent the signal delivery device 100 from moving relative to the target tissue, and can thereby improve the consistency of the patient's response to the electrical signal.

Referring again to FIG. 2A, the insertion path 210 can be linear or at least generally linear, as shown in FIG. 2A. An at least generally linear insertion path 210 is expected to increase the speed and/or precision with which the signal delivery device 100 can be positioned (e.g., by a practitioner) at least proximate to the target location, e.g., by minimizing or eliminating the need to reorient the signal delivery device 100 during insertion. In other embodiments, the insertion path 210 can include a plurality of insertion path segments or portions that are angled relative to one another. Each of the insertion path portions can be associated with a change to an orientation of the signal delivery device 100 (e.g., by a practitioner during insertion). In at least some embodiments, each of the insertion path portions has a vector component that is aligned along the inferior-superior axis, which is expected to reduce or minimize changes to the orientation of the signal delivery device 100 during insertion and increase the speed and/or precision with which the signal delivery device 100 can be positioned at least proximate to the target location. In other embodiments, one or more of the insertion path portions can have another suitable alignment. During insertion, the patient P can be at least partially sedated, unconscious, awake under local anesthesia, etc.

In at least some embodiments, an insertion point or opening 212 can be formed in the submental region SM and the signal delivery device 100 can be moved through the opening 212 and along the insertion path 210. In the illustrated embodiment, the opening 212 is a percutaneous opening formed using a percutaneous or other minimally invasive insertion tool 214, such as a needle (e.g., a percutaneous injection needle), stylet, and/or trocar, without performing a dissection of the submental region SM. In some embodiments, all or a portion of the insertion tool 214 can be straight, curved at an angle, e.g., of between about 60 degrees and about 75 degrees, helical, or can have another suitable shape or configuration. Additionally, or alternatively, the percutaneous insertion tool 214 can be used to position the signal delivery device 100 within the patient, for example, by projecting the signal delivery device 100 outwardly from within the percutaneous insertion tool 214 or otherwise releasing the signal delivery device 100 from the percutaneous insertion tool 214 when the signal delivery device 100 is positioned at least proximate to the target location. In other embodiments, the opening 212 can be formed through the patient's chin C, jaw J, and/or mandible M, e.g., using a drill or another suitable tool. In further embodiments, the opening 212 can be formed in a side of the patient's oral cavity, e.g., through the patient's cheek, and then the insertion tool 214 can pass through the tongue T and/or another opening formed sublingually in the patient's mouth. In some embodiments, forming the opening 212 through bone, such as in the jaw J and/or the mandible M, is expected to increase the stability of the signal delivery device 100, e.g., after implantation, and/or can allow for a longer (e.g., leaded) signal delivery device to be used.

FIG. 2A also schematically illustrates a portion of a representative ultrasound probe 201, which can be used to aid in the process of identifying where to form the opening 212, identifying the target location, moving the signal delivery device 100 along the insertion path 210, and/or otherwise positioning the signal delivery device 100 at least proximate to the target location. In at least some embodiments, the ultrasound probe 201 has an orientation that is at least generally similar or identical to the orientation of the signal delivery device 100 (e.g., at least a component of the ultrasound probe's orientation is aligned along the inferior-superior axis). Accordingly, the ultrasound probe 201 can be used to visualize the target location, the signal delivery device 100, and/or the percutaneous insertion tool 214 before, during, and/or after the procedure to position the signal delivery device 100 at least proximate to the target location. In such embodiments, aligning the orientations of the signal delivery device 100 and the ultrasound probe 201 is expected to increase the speed and/or accuracy with which the signal delivery device 100 is positioned. In some embodiments, the orientation of the ultrasound probe 201 can be used to visualize/identify the hyoglossus muscle HG (a retrusive muscle) and, accordingly, the user can avoid positioning the signal delivery device 100 near the hyoglossus muscle HG, e.g., to further reduce or prevent retrusive movement of the patient's tongue. In these and other embodiments, the ultrasound probe 201 can be used to position the signal delivery device 100 at or near the target location, and the signal delivery device 100 can deliver an electrical signal during all or a portion of the implantation process so that a practitioner can observe the patient's response to the electrical signal, e.g., to confirm that the signal delivery device 100 is at or near the target location and/or to inform further adjustments to the positioning of the signal delivery device 100. This is described in greater detail in U.S. Pat. Publication No. 2022/0161031, previously incorporated by reference herein, and U.S. application Ser. No. 18/104,739, the entirety of which is hereby incorporated by reference herein.

FIGS. 2C and 2D are submental and coronal sectional views, respectively, depicting the signal delivery device 100 at least proximate to the target location of FIG. 2A. As best shown in FIGS. 2C and 2D, at least a portion of the signal delivery device 100 (e.g., one or more of the electrodes 104; not visible in FIG. 2C) can be positioned laterally from genioglossus muscle GG (e.g., the patient's left genioglossus muscle) and/or inferior to/below the hyoglossus muscle HG (e.g., the patient's left hyoglossus muscle). As discussed above, this process can be carried out without penetrating into the genioglossus muscle GG and/or the hyoglossus muscle HG. In other embodiments, all or a portion of the signal delivery device 100 can be positioned within the genioglossus muscle GG, such as medially from one or more of the lateral branches AB, as described below with reference to FIGS. 5A-7B.

Referring to FIG. 2D, in the illustrated embodiment, the insertion point 212 is spaced apart and/or positioned laterally from a mid-sagittal plane of the patient P. In other embodiments, the insertion point 212 can be coplanar with the sagittal plane.

Figure 3C:
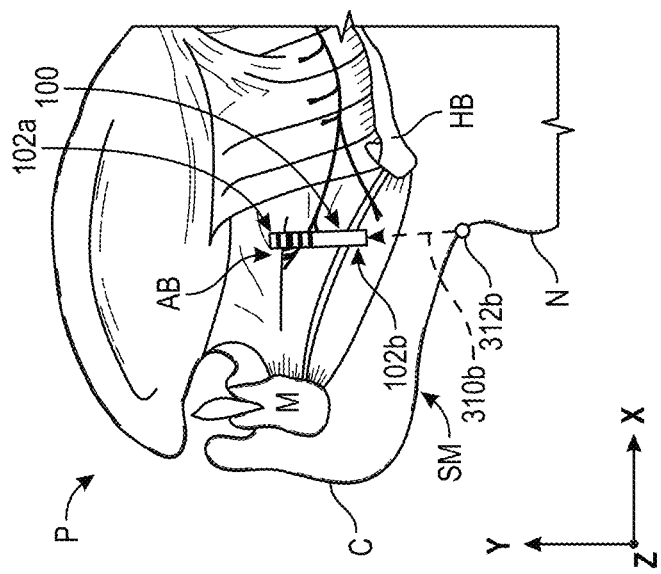
FIGS. 3A-3C are side sectional views of a portion of a patient's upper airway depicting respective signal delivery device insertion paths, each in accordance with embodiments of the present technology.
Figure 3B:
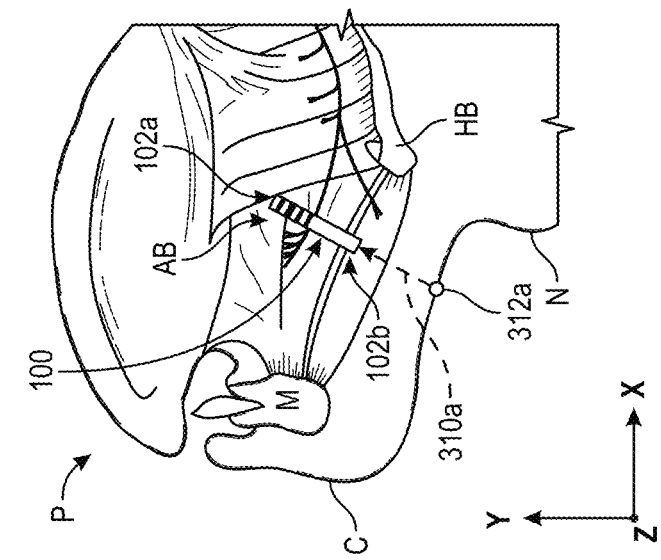
Figure 3A:
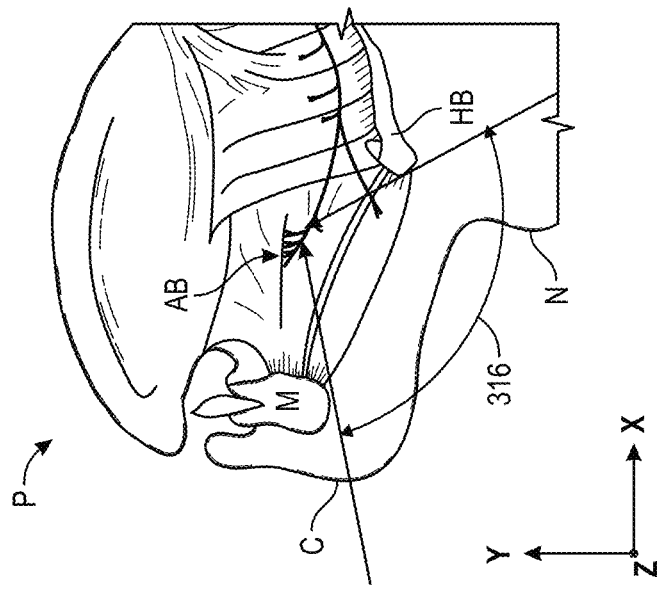

FIGS. 3A-3C are side sectional views of a portion of a patient's upper airway depicting corresponding signal delivery device insertion paths, each in accordance with embodiments of the present technology. FIG. 3A illustrates an angular range 316 of approaches for inserting a signal delivery device at one or more points along the anterior-posterior axis (x-axis). For a given target location, the mandible M and/or chin C can at least partially define an anterior-most limit to the range of insertion paths 316 and the hyoid bone HB and/or neck N can at least partially define a posterior-most limit to the range of insertion paths 316. In some embodiments, a preferred insertion path bisects the range of insertion paths 316 or is within plus or minus 20 degrees, 15 degrees, 10 degrees, 5 degrees, 1 degree, any angle therebetween, or another suitable angle of the bisecting insertion path.

The insertion opening associated with individual ones of the range of insertion paths 316 may influence the relative orientation of the signal delivery device 100. For example, referring to FIG. 3B, a first insertion path 310a can be used to position the signal delivery device 100 at least proximate to one or more of the anterior branches AB, and can include a first opening 312a formed proximate/posterior to the mandible M and/or the chin C and distal/anterior from the hyoid bone HB and/or the neck N. Because of the relatively anterior position of the first opening 312a, the first end portion 102a of the signal delivery device 100 can be superior and posterior relative to the second end portion 102b. Accordingly, the signal delivery device 100 can be advanced along the first insertion path 310a in an at least partially anterior-to-posterior direction, e.g., along a path having a vector component aligned with the anterior-to-posterior direction.

As another example, referring to FIG. 3C, a second insertion path 310b can be used to position the signal delivery device 100 at least proximate to one or more of the anterior branches AB, and can include a second opening 312b that is more posteriorly positioned than the first opening 312a of FIG. 3B, such that the first end portion 102a of the signal delivery device 100 is superior and anterior relative to the second end portion 102b. In at least some embodiments, the patient's head can be rotated posteriorly before and/or during formation of the second opening 312b to at least partially or fully prevent the neck N from obstructing access to the submental region SM. Accordingly, the signal delivery device 100 can be advanced along the second insertion path 310b in an at least partially posterior-to-anterior direction, e.g., along a path having a vector component aligned with the posterior-to-anterior direction (e.g., the x-axis, as shown in FIG. 3C).

Figure 4A:
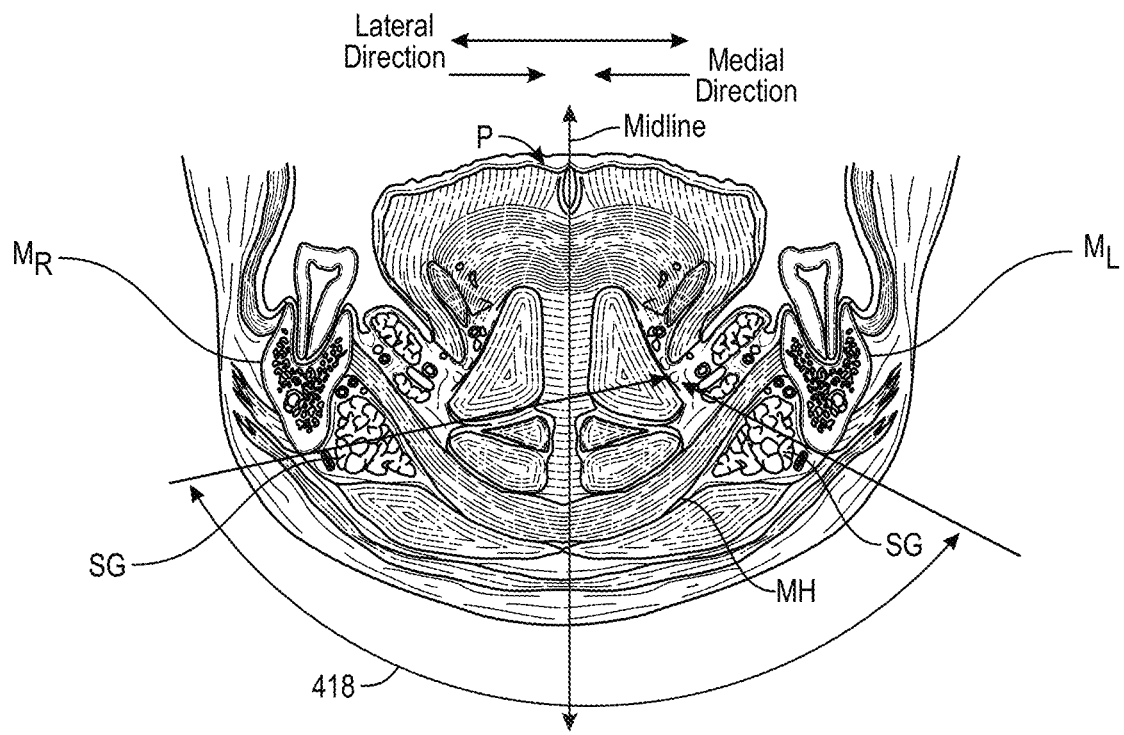
FIGS. 4A-4C are coronal sectional views of a portion of a patient's upper airway depicting respective signal delivery device insertion paths, each in accordance with embodiments of the present technology.
Figure 4B:
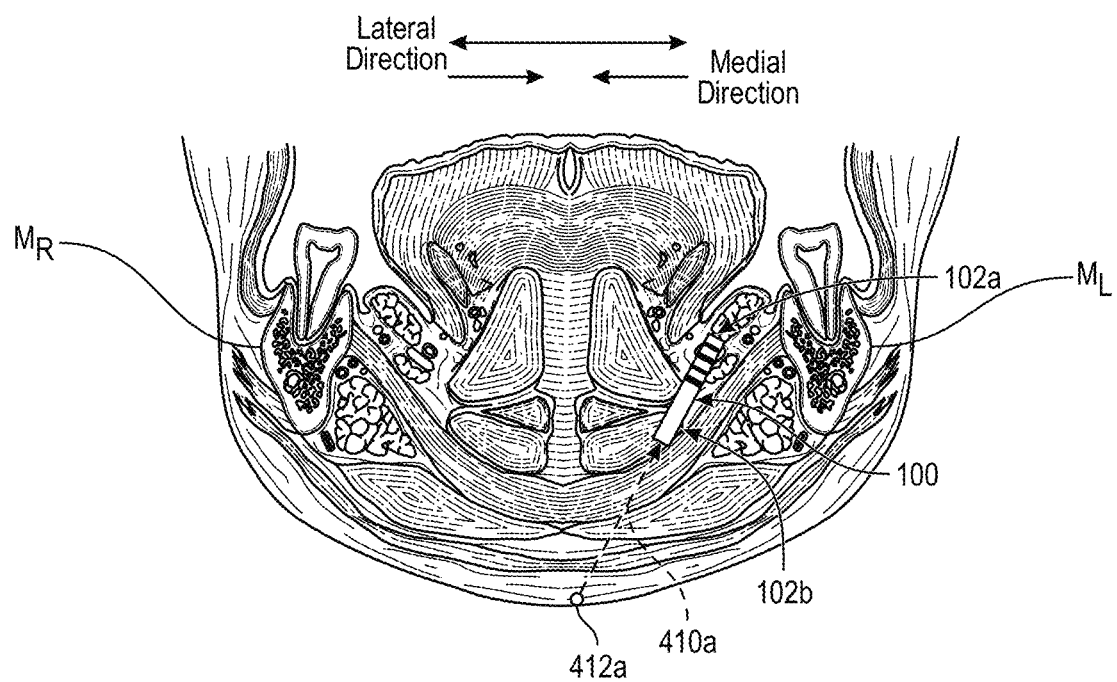
Figure 4C:
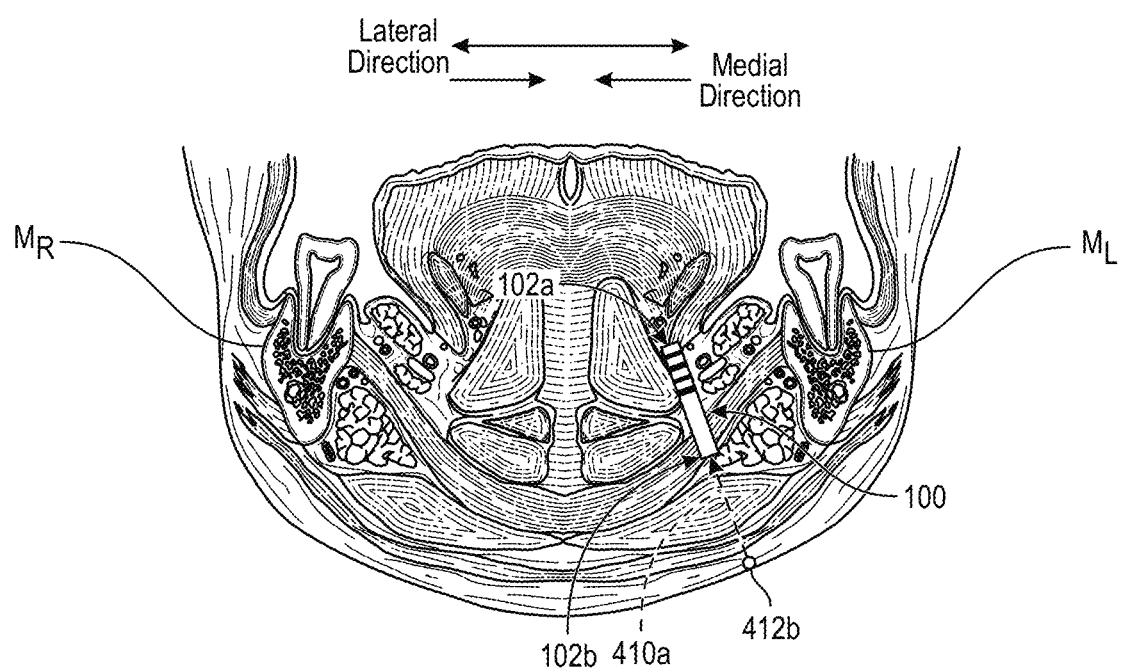

FIGS. 4A-4C are coronal sectional views of a portion of a patient's upper airway depicting respective signal delivery device insertion paths, each in accordance with embodiments of the present technology. FIG. 4A illustrates a range of insertion paths 418 that vary in the medial-lateral direction. For a given target location and/or tissue, a left mandible portion $M_L$ and a right mandible portion $M_R$ can at least partially define lateral bounds to the range of insertion paths 418. In some embodiments, a preferred insertion path bisects the range of insertion paths 418 between the patient's midline and the mandible portion $M_L$, $M_R$ most proximate to the target anatomical location, or is within plus or minus 20 degrees, 15 degrees, 10 degrees, 5 degrees, 1 degree, any angle therebetween, or another suitable angle of the bisecting insertion path. The insertion path can be angled in the anterior-posterior direction (e.g., into and out of the image in FIG. 4A) to avoid piercing through sensitive areas, such as the patient's salivary glands SG. In these and/or other embodiments, the insertion path can be angled to pierce through the patient's mylohyoid muscle MH while avoiding, or at least generally avoiding, piercing/penetrating through one or more other muscles in the patient's neck and/or lower jaw. While the insertion path may pass through the mylohyoid muscle MH, the signal delivery device and/or one or more of the electrodes thereof can be free of (e.g., not chronically embedded within) the mylohyoid muscle MH after implantation.

The opening associated with individual ones within the range of insertion paths 418 may influence the relative orientation of the signal delivery device 100. For example, referring to FIG. 4B, a first insertion path 410a can be used to position the signal delivery device 100 at least proximate to one or more of the anterior branches AB, and can include a first opening 412a formed generally centrally between the left and right mandible portions $M_L$, $M_R$. Because of the central position of the first opening 412a, the first end portion 102a of the signal delivery device 100 is superior and lateral relative to the second end portion 102b. Accordingly, the signal delivery device 100 can be advanced along the first insertion path 410a in an at least partially medial-to-lateral direction, e.g., along a path having a vector component aligned with the medial-to-lateral direction.

As another example, referring to FIG. 4C, a second insertion path 410b can be used to position the signal delivery device 100 at least proximate to one or more of the anterior branches AB, and can include a second opening 412b formed proximate to the left mandible portion $M_L$. Because of the relatively lateral position of the second opening 412b, the first end portion 102a of the signal delivery device 100 is superior and medial relative to the second end portion 102b. Accordingly, the signal delivery device 100 can be advanced along the second insertion path 410b in an at least partially lateral-to-medial direction, e.g., along a path having a vector component aligned with the lateral-to-medial direction.

The insertion paths of FIGS. 2A-4C are generally described with reference to positioning the signal delivery device 100 at least proximate to the anterior branches AB of the hypoglossal nerve HGN. In other embodiments, any of the insertion paths described herein (or at least one or more portions thereof) can be used to position the signal delivery device 100 at least proximate to one or more other target locations, such as at least proximate to the medial branch MB of the hypoglossal nerve HGN and/or the patient's genioglossus muscle GG. Moreover, additional embodiments associated with the genioglossus muscle GG are described below with reference to FIGS. 7A-9B.

Generally, electrical signals applied to a nerve, including the hypoglossal nerve HGN, have a characteristic neuromuscular activation threshold (e.g., a minimum amplitude) associated with causing an evoked patient motor response in tissue innervated by the nerve. Often, little to no motor response is evoked before the neuromuscular activation threshold is met. After meeting or exceeding the neuromuscular activation threshold, further changes (e.g., further increases to the delivered energy) to the electrical signals often produce little to no additional motor response, making it difficult to induce the motor response gradually over time. One approach to address this problem is to deliver the electrical signal to one or more of the anterior branches AB of the hypoglossal nerve HGN, as described previously with reference to FIGS. 2A-4C. Each of the distal brachiated portions DB innervates one or more specific muscle fibers of the genioglossus muscle GG. For example, FIG. 5A, which is a side view illustrating a patient's tongue and upper airway, illustrates each of the distal brachiated portions DB of the hypoglossal nerve HGN innervating specific portions or muscular compartments GGo1-GGo4, GGh1, GGh2 of the patient's genioglossus muscle GG. In the illustrated embodiment, the portions include four oblique fiber compartments GGo1-GGo4 and two horizontal fiber compartments GGh1, GGh2 of the genioglossus muscle GG. In other embodiments and/or for other patients, the genioglossus muscle GG can include more or fewer muscular compartments, and/or individual compartments can have a greater or lesser size. Individual ones of the compartments GGo1-GGo4, GGh1, GGh2 can include a corresponding surface portion T1-T6 of the patient's tongue T. Prior to delivering the electrical signal, the tongue T has a first or unstimulated geometry or contour 530. When each of the genioglossus compartments GGo1-GGo4, GGh1, GGh2 contracts (e.g., in response to an electrical signal from a signal delivery device), the contraction can cause a corresponding surface portion T1-T6 of the patient's tongue T to displace inwardly toward the mandible M. This, in turn, can increase airflow through the patient's oral cavity OC, e.g., by decreasing or even preventing obstruction in a retropalatal portion RP and/or a retrolingual portion RL of the patient's oral cavity OC, and/or decreasing or even preventing pressure from the tongue T against the patient's soft palate. The patient's mandible M, hyoid bone HB, and geniohyoid muscle GH are shown for context.

Figure 5A:
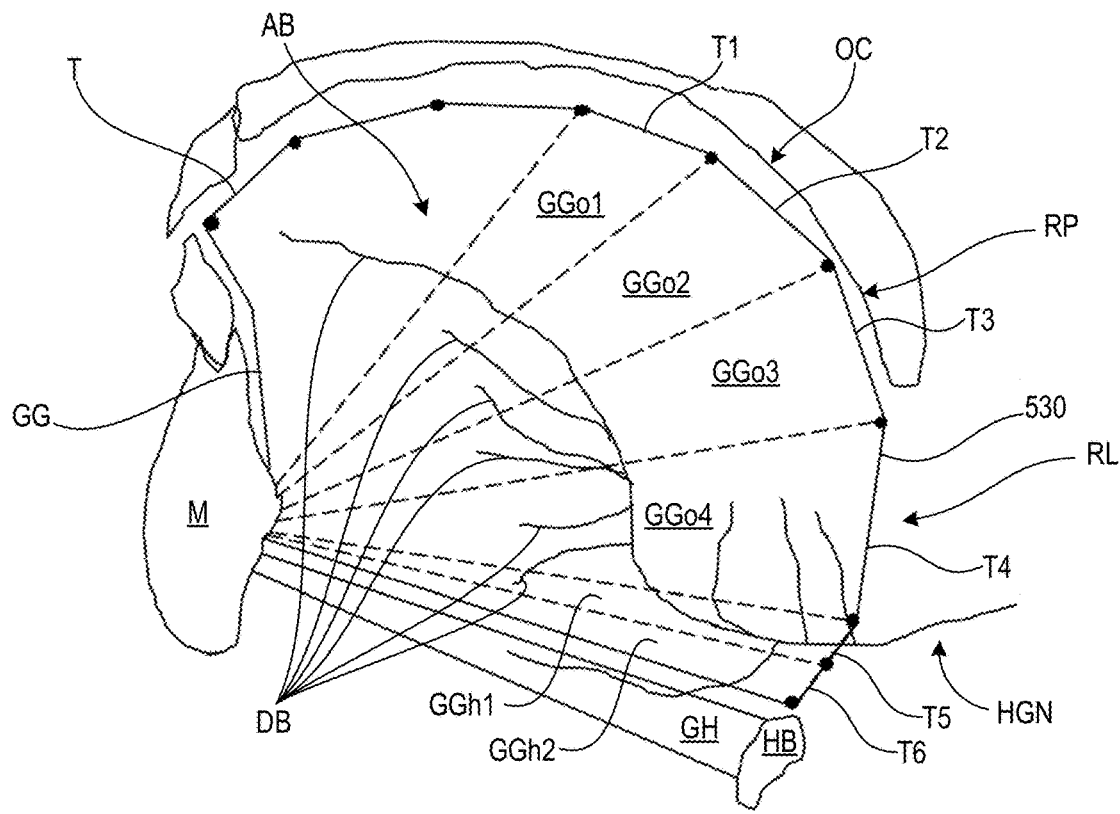
FIGS. 5A-5E are side views of a patient's tongue and upper airway depicting respective signal delivery device stimulation patterns, in accordance with embodiments of the present technology.
Figure 5B:
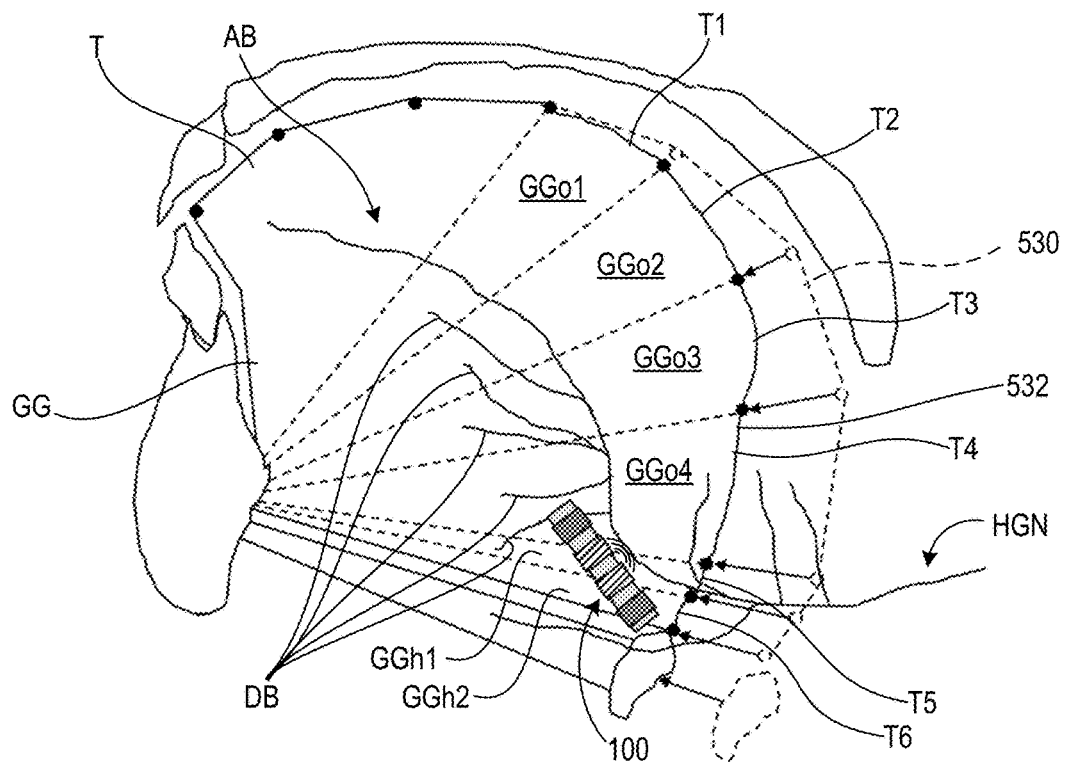

Delivering an electrical signal to the hypoglossal nerve HGN at a location posterior to the anterior branches AB, such as shown in FIG. 5B, is expected to produce a motor response throughout the patient's tongue T, e.g., in each (e.g., all) of the compartments GGo1-GGo4, GGh1, GGh2 of the genioglossus muscle GG, and cause a corresponding movement of each of the surface portions T1-T6 of the patient's tongue T from the first geometry 530 to a second or contracted geometry or contour 532. However, the brachiated nature of the anterior branches AB and the distal brachiated portions DB allows for geographic segregation of current density to selectively target some subset of the distal brachiated portions DB and, by extension, a corresponding subset of the genioglossus muscle GG compartments. The response from the targeted anterior branch AB fibers is expected to be binary (e.g., the signal delivered to the individual anterior branch AB will either produce a motor response or not produce a motor response), but the signal can be delivered such that a subset of the anterior branches AB can receive the electrical signal and cause a corresponding subset of genioglossus muscle GG compartments to contract and, by extension, cause a portion of the patient's tongue to move. This is described in greater detail below with reference to FIGS. 5C-6C.

Figure 5C:
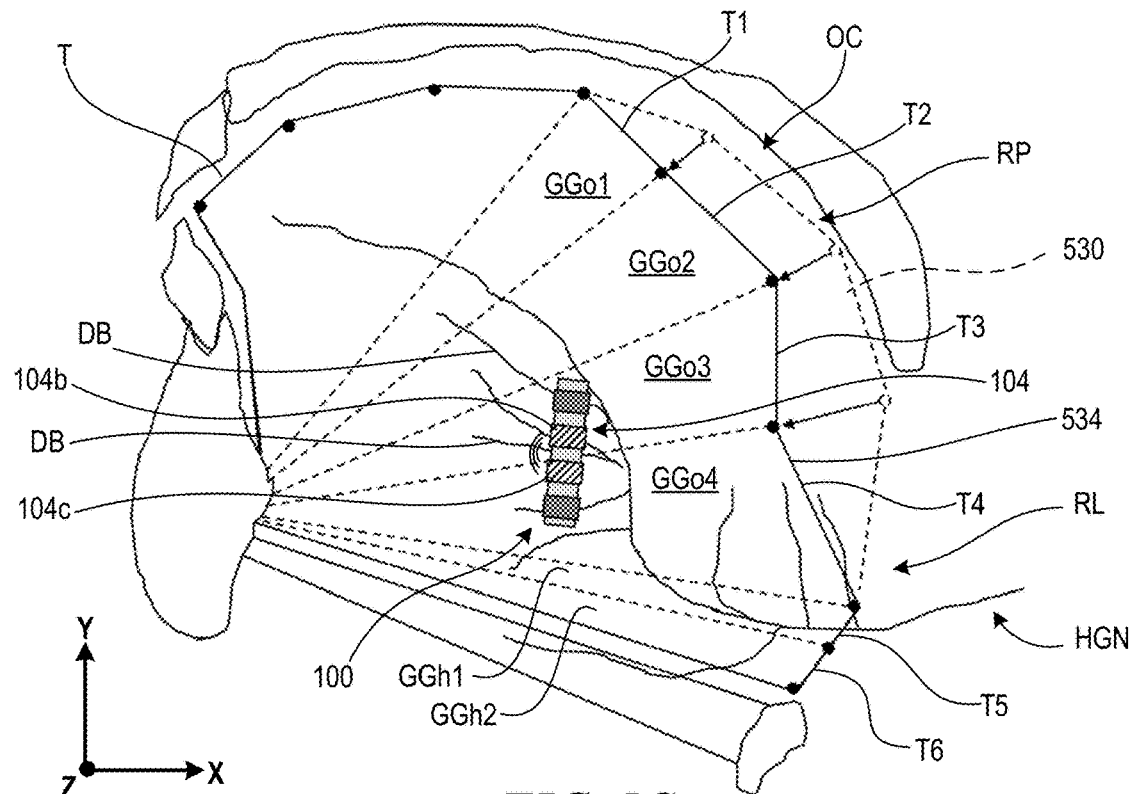

FIG. 5C illustrates the signal delivery device 100 in a position and/or orientation that is at least generally similar to the position and/or orientation described previously with reference to FIG. 3C. In other embodiments, the signal delivery device 100 can be positioned and/or oriented as shown and/or described with reference to one or more of FIGS. 2A-2D, 3A, 3B, and/or 4A-4C. The spacing between individual ones of the electrodes 104 can be at least generally similar to or the same as the spacing between the anterior branches AB and/or the distal brachiated portions DB thereof, so that individual ones of the electrodes 104 can be positioned at least proximate to (and/or otherwise positioned to deliver an electrical signal to) individual ones of the distal brachiated portions DB. In the illustrated embodiment, for example, second and third electrodes 104b, 104c of the signal delivery device 100 are positioned to deliver the electrical signal to the distal brachiated portions DB innervating second and third compartments GGo2, GGo3 of the genioglossus muscle GG and produce a motor response in these portions. Accordingly, activating the second and third electrodes 104b, 104c can create an electrical field that delivers an electrical signal to the distal brachiated portions DB innervating the second and third compartments GGo2, GGo3 of the genioglossus muscle GG and produce a motor response in these portions. This, in turn, can cause a corresponding movement of second and third surface portions T2, T3 of the patient's tongue T, e.g., from the first geometry 530 to a third or contracted geometry or contour 534 (different from, e.g., the second geometry 532 in FIG. 5B). This tongue movement can increase airflow through the retropalatal portion RP of the patient's oral cavity OC, e.g., by reducing or preventing tongue pressure on the patient's soft palate, without, or generally without, changing a geometry of the retrolingual portion RL of the patient's oral cavity OC. In some instances, the motor response of the second and third compartments GGo2, GGo3 and/or the second and third surface portions T2, T3 may cause other and/or unstimulated portions of the genioglossus muscle GG to move. For example, the first compartment GGo1, fourth compartment GGo4, and/or corresponding surface portions of the patient's tongue (e.g., first surface portion T1, fourth surface portion T4) can move in response to the movement of the second and third compartments GGo2, GGo3 and/or the second and third surface portions T2, T3, as shown in FIG. 5C. The response of these other and/or unstimulated portions is expected to be of lesser magnitude than the response of the portions of the genioglossus muscle GG that receive the electrical signal due, wholly or in part, to the neighboring and/or adjacent positions of the other unstimulated portions and the target portions.

In the embodiment illustrated in FIG. 5C, the signal delivery device 100 is positioned to deliver the electrical signal to the left hypoglossal nerve HGN. Accordingly, it is expected that all or at least part of a left side of the patient's tongue T will move as shown in FIG. 5C, without or at least generally without moving a right side of the patient's tongue T. The movement of the left side of the patient's tongue T is expected to be sufficient to reduce or even prevent obstruction of the patient's airway. In some embodiments, signal delivery devices can be positioned bilaterally (e.g., to stimulate distal branches of the patient's left and right hypoglossal nerves) so that both the left and right sides of the patient's tongue T move as shown in FIG. 5C.

Although FIG. 5C illustrates movement of a portion of the patient's tongue T in a sagittal (e.g., x-y) plane, those skilled in the art will appreciate that the tongue T can move in other directions. For example, because the tongue T is a muscular hydrostat and maintains a constant (or at least generally constant) volume during movement, the contraction of the tongue illustrated in FIG. 5C is expected to cause a corresponding expansion (e.g., lateral expansion) of the tongue T in a direction at least generally parallel to the z-axis.

Figure 5D:
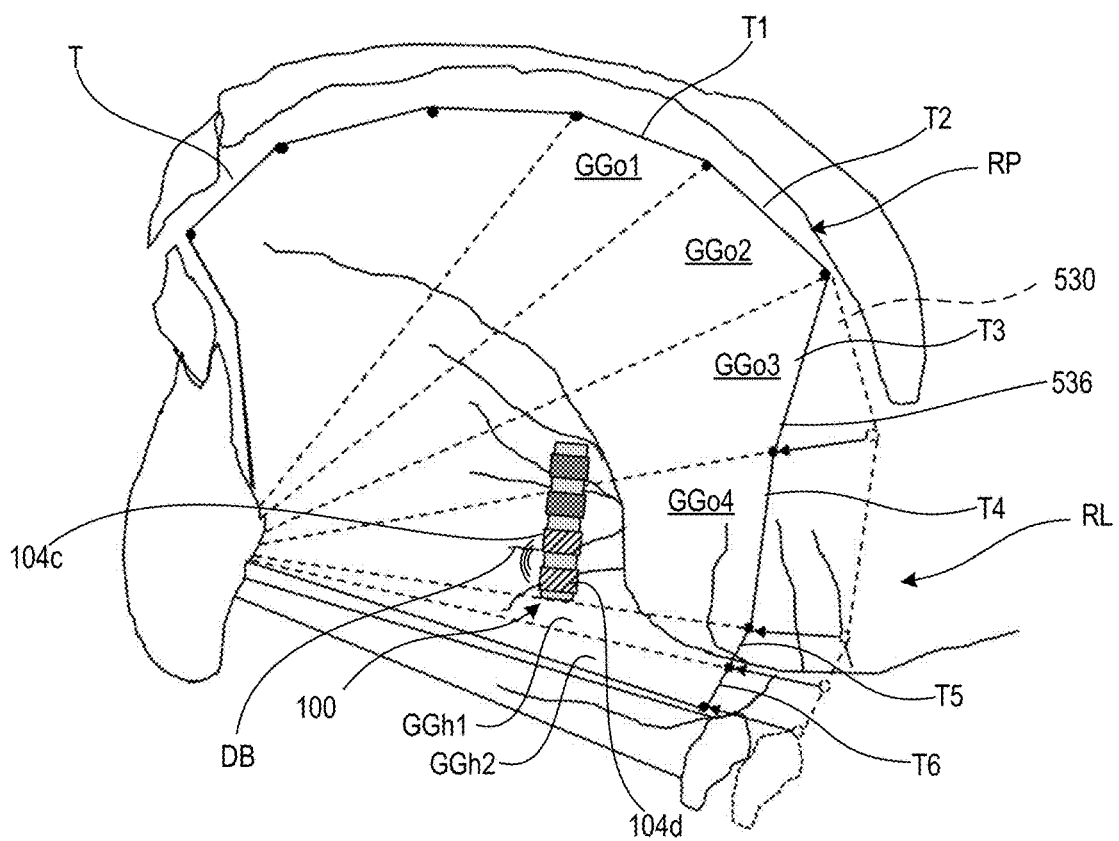

FIG. 5D illustrates the signal delivery device 100 in the same position and/or orientation shown in FIG. 5C, but with a different combination of active electrodes. More specifically, in FIG. 5D, third and fourth electrodes 104c, 104d of the signal delivery device 100 are activated to deliver the electrical signal to the distal brachiated portions DB innervating a fourth compartment GGo4 of the genioglossus muscle GG and the horizontal fiber compartments GGh1, GGh2. This, in turn, can cause fourth, fifth, and sixth surface portions T4, T5, T6 of the patient's tongue T to contract from the first geometry 530 to a fourth contracted or contoured geometry 536 (different from, e.g., the second geometry 532 in FIG. 5B and/or the third geometry 534 in FIG. 5C) and thereby increase airflow through a retrolingual portion RL of the patient's oral cavity OC, without, or generally without, changing a geometry of the retropalatal portion RP of the patient's oral cavity OC.

Figure 5E:
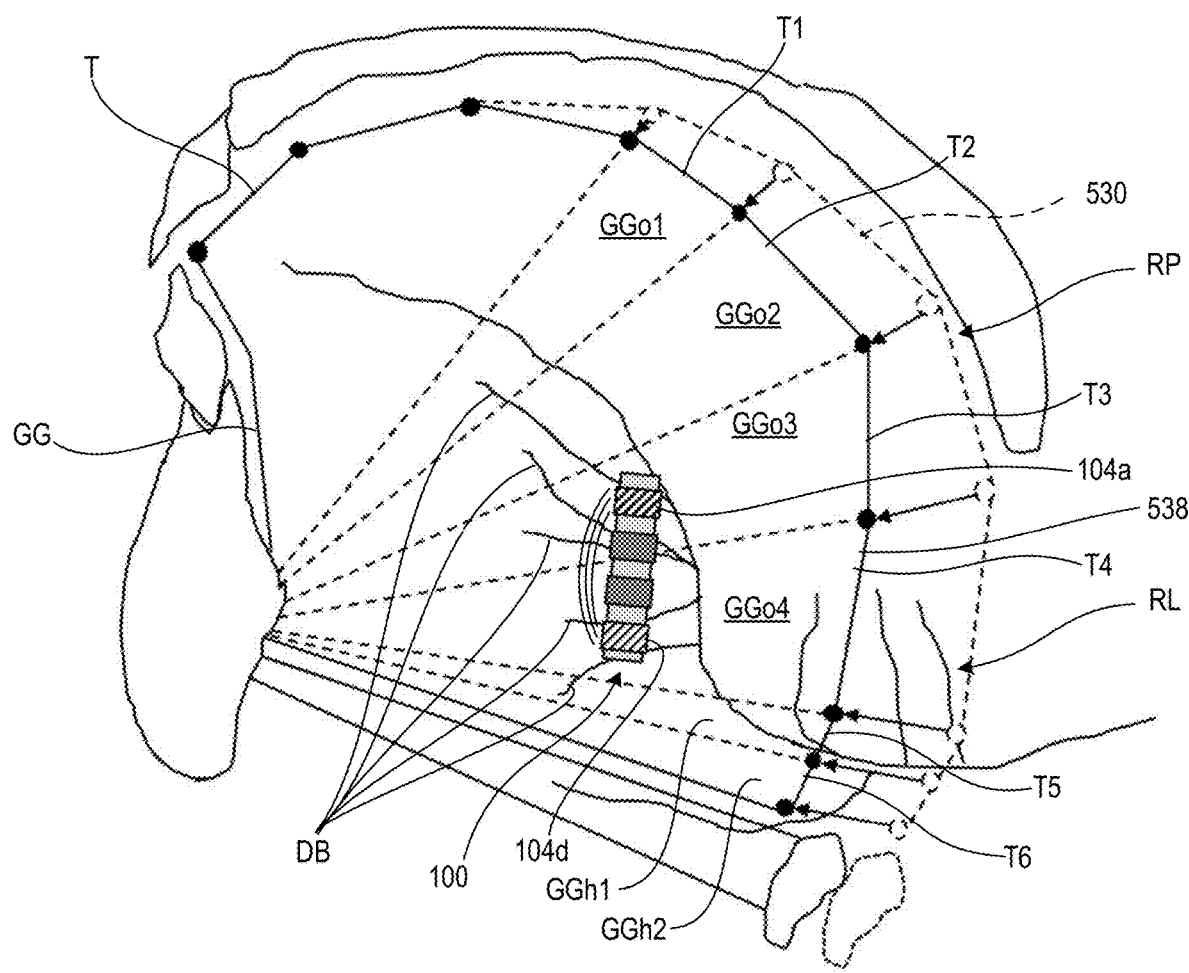

FIG. 5E illustrates the signal delivery device 100 in the same position and/or orientation shown in FIG. 5C, but with a different combination of active electrodes. More specifically, in FIG. 5E, the first and fourth electrodes 104a, 104d of the signal delivery device 100 are active to deliver the electrical signal to the distal brachiated portions DB innervating each of the compartments GGo1-GGo4, GGh1, GGh2 of the genioglossus muscle GG. This is turn causes the tongue to contract from the first geometry 530 to a fifth geometry or contour 538 at least generally similar to or the same as the second geometry 532 (FIG. 5B). In other embodiments, additional (or all) electrodes of the signal delivery device 100 can be activated to move the tongue T to the second geometry 532. Thus, from the position shown in FIG. 5E, the signal delivery device 100 can produce the same, or an at least generally similar, motor response as the embodiment in FIG. 5B in which the signal delivery device 100 was positioned to stimulate a posterior portion of the hypoglossal nerve HGN. Additionally, from the position shown in FIG. 5E, the signal delivery device 100 can produce a different or lesser motor response by selectively activating different combinations of electrodes, as described previously with reference to FIGS. 5C and 5D. Accordingly, the delivery approaches of the present technology, and/or the positions and/or orientations of the signal delivery devices described herein, can provide an array of graduated patient responses by selectively increasing or decreasing the number of anterior branches AB that receive the electrical signal. In at least some embodiments, for example, individual ones of the distal brachiated portions DB can be stimulated sequentially to, e.g., build up a full patient response (e.g., protrusive response, airflow improvement, etc.) over time in a way that is not possible, or very difficult, to achieve by activating more posterior portions of the hypoglossal nerve (e.g., the medial branch MB).

In some embodiments, the patient's airway and/or tissue collapse pattern (e.g., anteroposterior, latero-lateral, circular/circumferential, etc.) can be identified, and individual ones of the distal brachiated portions DB can be stimulated to change a geometry of the corresponding portion of the patient's tongue T, e.g., to reduce or prevent the tissue collapse at that and/or other portions of the patient's tongue T and/or to change a geometry of other portions of the patient's airway (e.g., to prevent the patient's tongue from pressing on the soft palate, reduce the pressure with which the patient's tongue presses against the soft palate, move the patient's epiglottis anteriorly, etc.). This, in turn, can allow only the portion of the patient's tongue and/or other tissue(s)

causing the obstructive event to move, without or at least generally without moving other tissues/tissue portions.

Figure 6A:
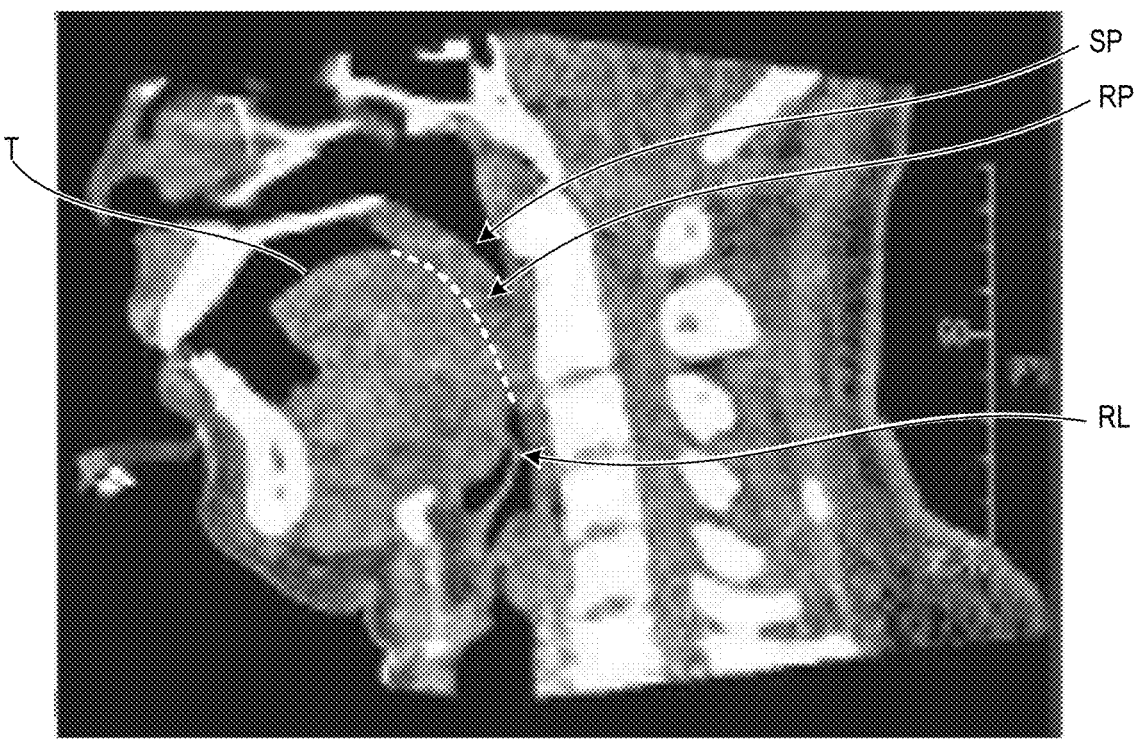
FIGS. 6A-6C are side sectional views of a patient's oral cavity and upper airway depicting representative tongue collapse patterns that can be addressed via techniques in accordance with embodiments of the present technology.
Figure 6B:
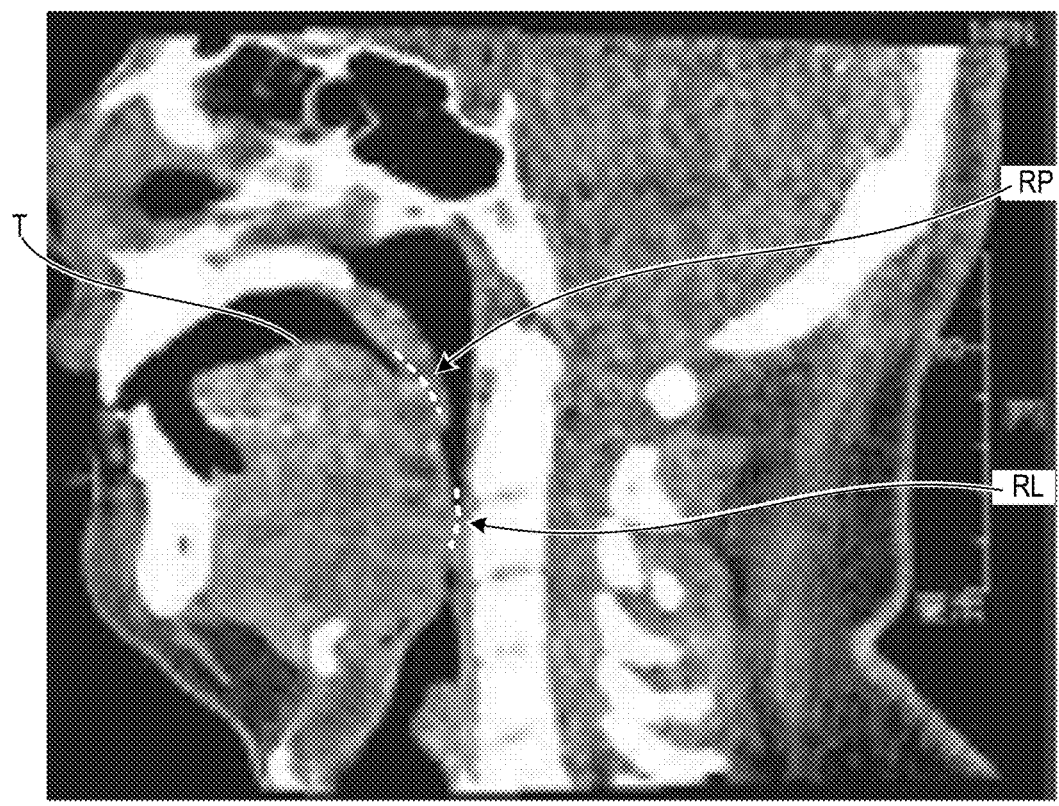
Figure 6C:
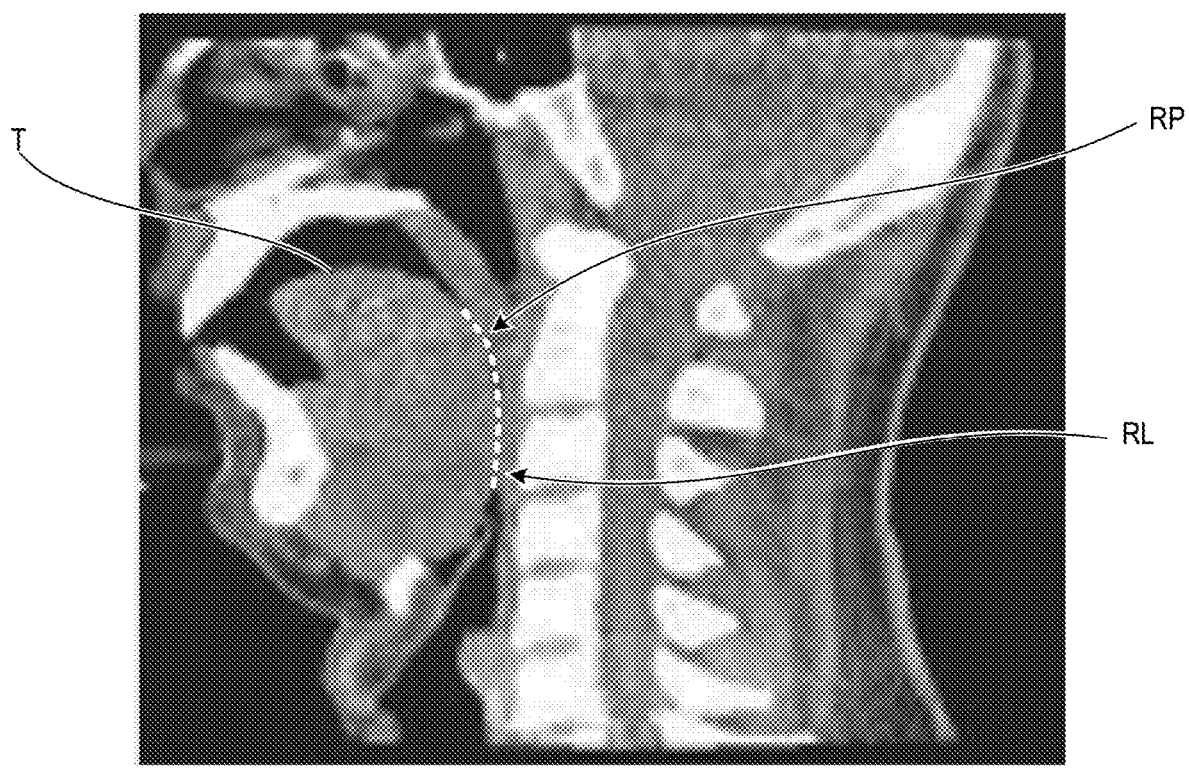

FIGS. 6A-6C are side sectional views of a patient's oral cavity and upper airway and depict representative tongue collapse patterns that can be addressed via techniques in accordance with embodiments of the present technology. More specifically, FIG. 6A illustrates upper tongue collapse in the retropalatal portion RP of the patient's airway, with the tongue T pressing against the patient's soft palate (e.g., shown using dashed line). To address the upper tongue collapse, an electrical signal can be applied to one or more muscular compartments of the genioglossus muscle at least generally similarly or identically to as described previously with reference to FIG. 5C, e.g., to reduce or prevent the tongue T from pressing against the soft palate SP and/or otherwise increase airflow through the retropalatal portion RP of the patient's airway.

FIG. 6B illustrates lower tongue collapse in a retrolingual portion RL of the patient's airway. To address the lower tongue collapse, an electrical signal can be applied to one or more muscular compartments of the genioglossus muscle at least generally similarly or identically to as described previously with reference to FIG. 5D, e.g., to increase airflow through the retrolingual portion RL of the patient's airway.

FIG. 6C illustrates combined (e.g., full) tongue collapse in both the retropalatal portion RP and the retrolingual portion RL of the patient's airway. To address the lower tongue collapse, an electrical signal can be applied to one or more muscular compartments of the genioglossus muscle at least generally similarly or identically to as described previously with reference to FIG. 5E, e.g., to increase airflow through the retropalatal portion RP and the retrolingual portion RL of the patient's airway.

Referring to FIGS. 5C-6C together, selectively delivering the electrical signal to individual ones of the distal brachiated portions DB of the anterior branches AB is expected to improve patient comfort and/or patient compliance with therapy, e.g., by reducing the amount and/or energy of stimulation delivered and/or minimizing the tongue movement induced to address the patient's sleep apnea. This can, for example, reduce or prevent tongue abrasion associated with movement of the tongue that drives an anterior portion of the patient's tongue against the patient's teeth (e.g., protrusion of the tongue anteriorly and/or out from the patient's mouth) and/or otherwise reduces patient arousal during therapy (e.g., by reducing or preventing unpleasant and/or uncomfortable sensations, such as cramping, buzzing, and/or tongue spasms, associated with electrical signals that cause the entire tongue T to contract/protrude). Additionally, or alternatively, reducing the stimulation energy delivered can reduce power consumption by the signal delivery device and/or improve the battery life of the signal delivery device and/or an external power source.

Another approach is to apply the electrical signal directly to the muscle(s) associated with the motor response of interest. For example, applying electrical signals directly to one or both of the patient's genioglossus muscles GG will activate the same muscles as when the electrical signals are applied to one or more of the anterior branches AB of the hypoglossal nerve HGN, but additionally allows for a more gradual dose-response activation by recruiting terminal nerve/muscle fibers, e.g., compared to activating the nerves/nerve branches innervating the genioglossus muscle GG. For example, applying a first electrical signal having one or more first signal delivery parameters (e.g., amplitude, frequency, pulse width, etc.) to the genioglossus muscle(s) GG at a first time can cause a first motor response, and applying a second electrical signal having one or more second signal delivery parameters different from the one or more first signal delivery parameters to the genioglossus muscle(s) GG at a second time can cause a second motor response having a different (e.g., greater or lesser) degree, range, and/or amount of motion than the first motor response. In some embodiments, the first signal delivery parameters can include a first amplitude, and the second signal delivery parameters can include a second amplitude greater than the first amplitude such that delivery of the second electrical signal is expected to produce a greater motor response than delivery of the first electrical signal. Thus, applying the electrical signals directly to the genioglossus muscle(s) GG is expected to provide an improved ability to modulate the tongue motor response by increasing control over the evoked patient motor response and/or rate of genioglossus muscle GG contraction.

The foregoing increased control over the evoked patient motor response can improve the ability to reduce and/or prevent airway obstructions and/or improve patient comfort and/or therapy compliance. Additionally, or alternatively, applying the electrical signals directly to the genioglossus muscle(s) GG is expected to reduce or prevent activation of the retrusers at least because the genioglossus muscles GG are "downstream" from the anterior branches AB and thus positioned at least the same distance and/or further anteriorly from the retrusive branches of the hypoglossal nerve HGN than the anterior branches AB. This, in turn, is expected to reduce or prevent the electrical signals from being delivered to the retrusive branches and/or retrusive muscle fibers (e.g., the styloglossus and/or the hyoglossus muscles). Additionally, or alternatively, delivering the electrical signal to the genioglossus muscle GG causes the tongue T to protrude, which is expected to reduce or prevent retrusive motion of the tongue and/or produce a net positive protrusive response. In these and other embodiments, implanting the signal delivery device 100 to deliver the electrical signal to the genioglossus muscles GG is expected to increase the speed and/or precision with which the signal delivery device 100 can be positioned (e.g., by a practitioner) at least proximate to the target location, e.g., by minimizing or eliminating the need to reorient the signal delivery device 100 during insertion as described previously with reference to FIGS. 2A-2C. Additionally, because the genioglossus muscle GG is larger than the nerves innervating it, the genioglossus muscle GG is expected to be easier to identify (e.g., using the ultrasound probe 201 of FIG. 2A). Without being bound by theory, it is believed that the response of the genioglossus muscle GG to directly delivered electrical signals is less sensitive or insensitive to the position of the signal delivery device within the genioglossus muscle GG. Accordingly, the genioglossus muscle GG can define a larger area (e.g., compared to a nerve) within which the signal delivery device 100 can be positioned, which is expected to reduce the time associated with identifying and/or implanting the signal delivery device 100.

Figure 7A:
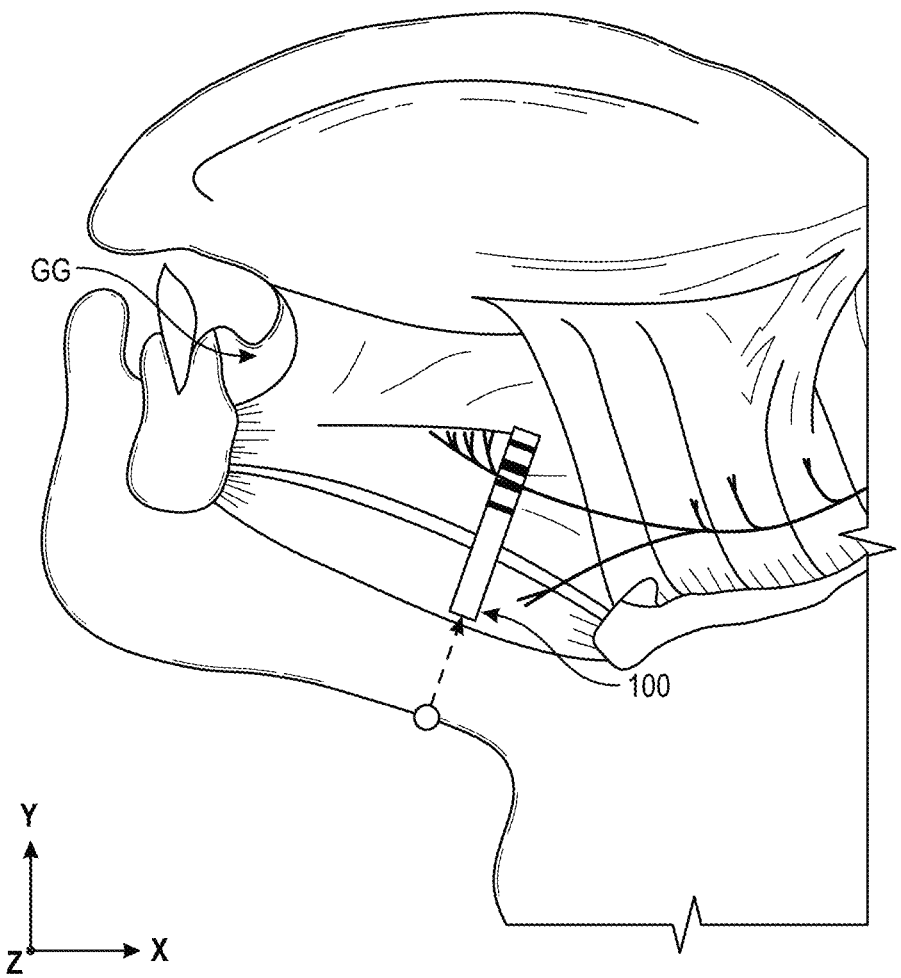
FIGS. 7A and 7B are side and submental sectional views, respectively, depicting a signal delivery device insertion path, in accordance with embodiments of the present technology.
Figure 7B:
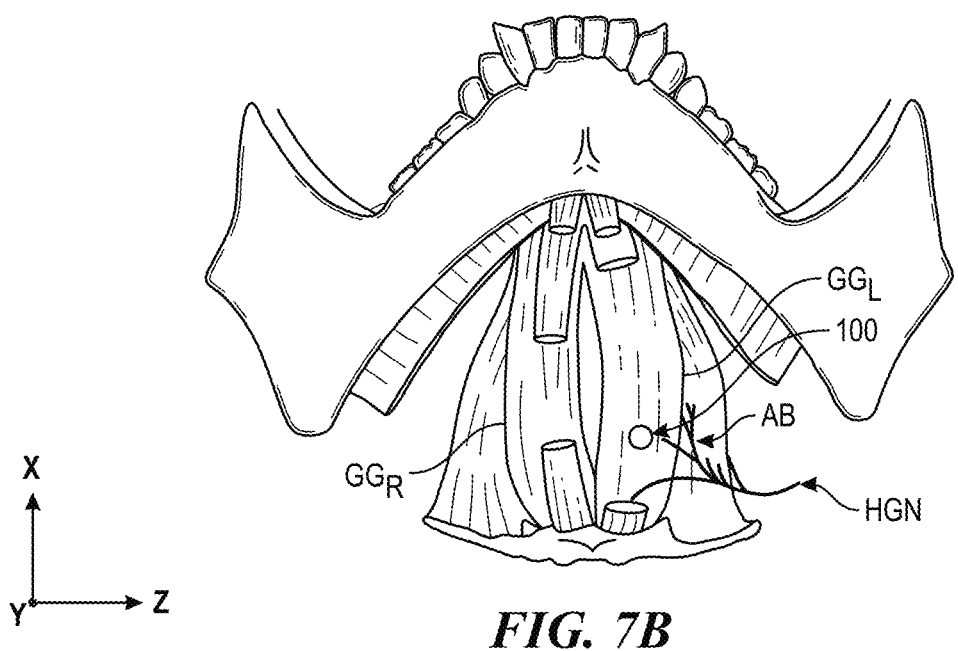

FIGS. 7A and 7B are side and submental sectional views, respectively, depicting a signal delivery device insertion path, configured in accordance with embodiments of the present technology. Referring to FIG. 7A, the signal delivery device 100 can have an anterior-posterior position, at least generally similar or identical to the anterior-posterior position of the signal delivery device 100 described previously with reference to FIG. 2A. Referring to FIG. 7B, all or a portion of the signal delivery device 100 can be positioned within one of the genioglossus muscles GG (e.g., a left genioglossus muscle $GG_L$ or a right genioglossus muscle $GG_R$) of the patient P. In the illustrated embodiment, the signal delivery device 100 is positioned within the patient's left genioglossus muscle $GG_L$. In these and other embodiments, both the left and right genioglossus muscles $GG_L$, $GG_R$ can have one or more of the signal delivery devices 100 positioned therein. In further embodiments, the signal delivery device 100 can be positioned laterally from the patient's right genioglossus muscle $GG_R$ or the left genioglossus muscle $GG_L$, and/or a first signal delivery device can be positioned laterally from the right genioglossus muscle $GG_R$ and a second signal delivery device can be positioned laterally from the left genioglossus muscle $GG_L$.

Figure 8A:
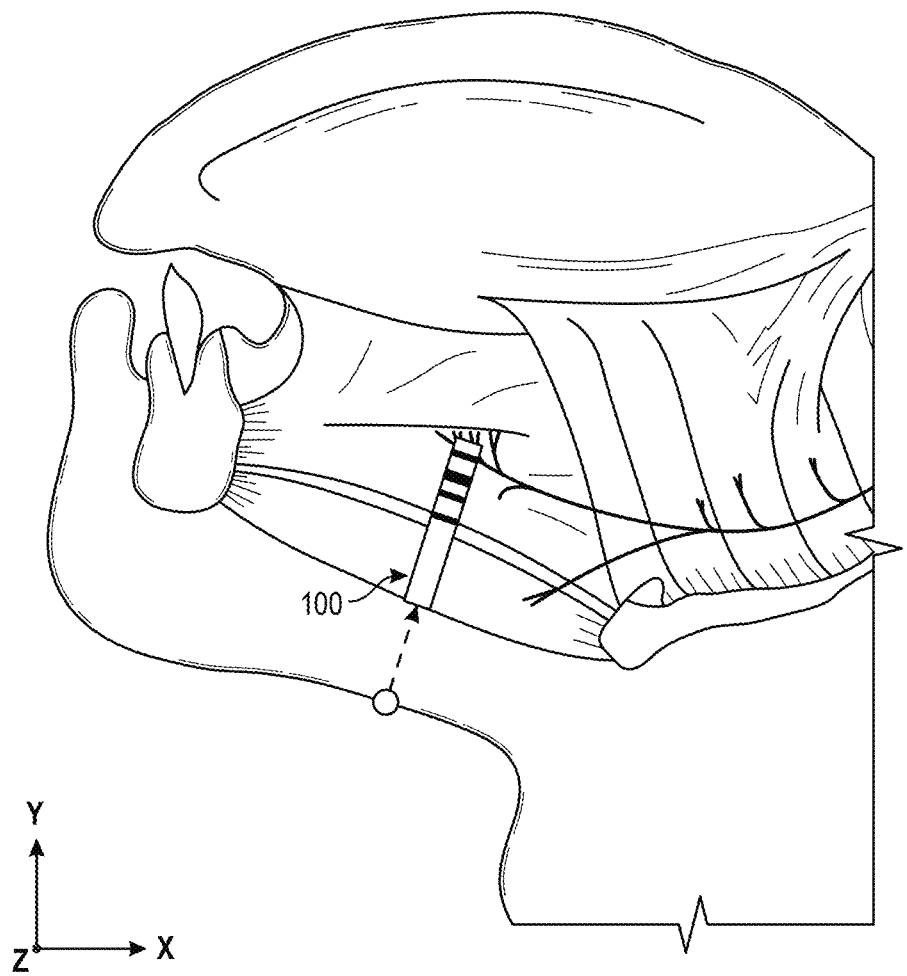
FIGS. 8A and 8B are side and submental sectional views, respectively, depicting a signal delivery device insertion path, in accordance with embodiments of the present technology.
Figure 8B:
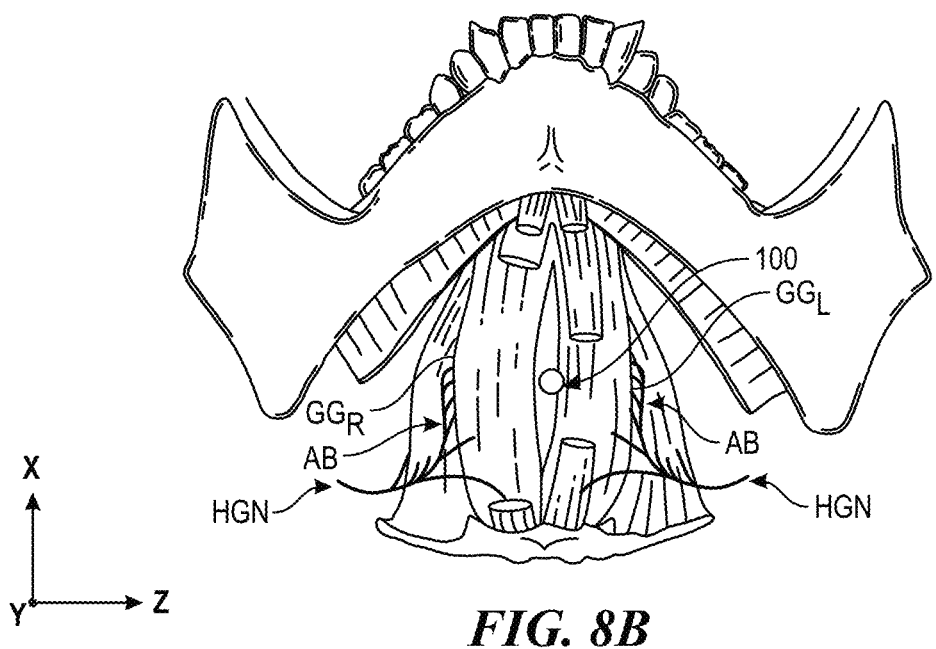

FIGS. 8A and 8B are side and submental sectional views, respectively, depicting a signal delivery device insertion path, configured in accordance with embodiments of the present technology. Referring to FIG. 8A, the anterior-posterior positioning of the signal delivery device 100 can be at least generally similar or identical to the anterior-posterior positioning of the signal delivery device 100 described previously with reference to FIG. 2A. Referring to FIG. 8B, all or a portion of the signal delivery device 100 can be positioned between the left and right genioglossus muscles $GG_L$, $GG_R$. In this position, the signal delivery device 100 can deliver a signal to one or both of the left and right genioglossus muscles $GG_L$, $GG_R$.

Figure 9A:
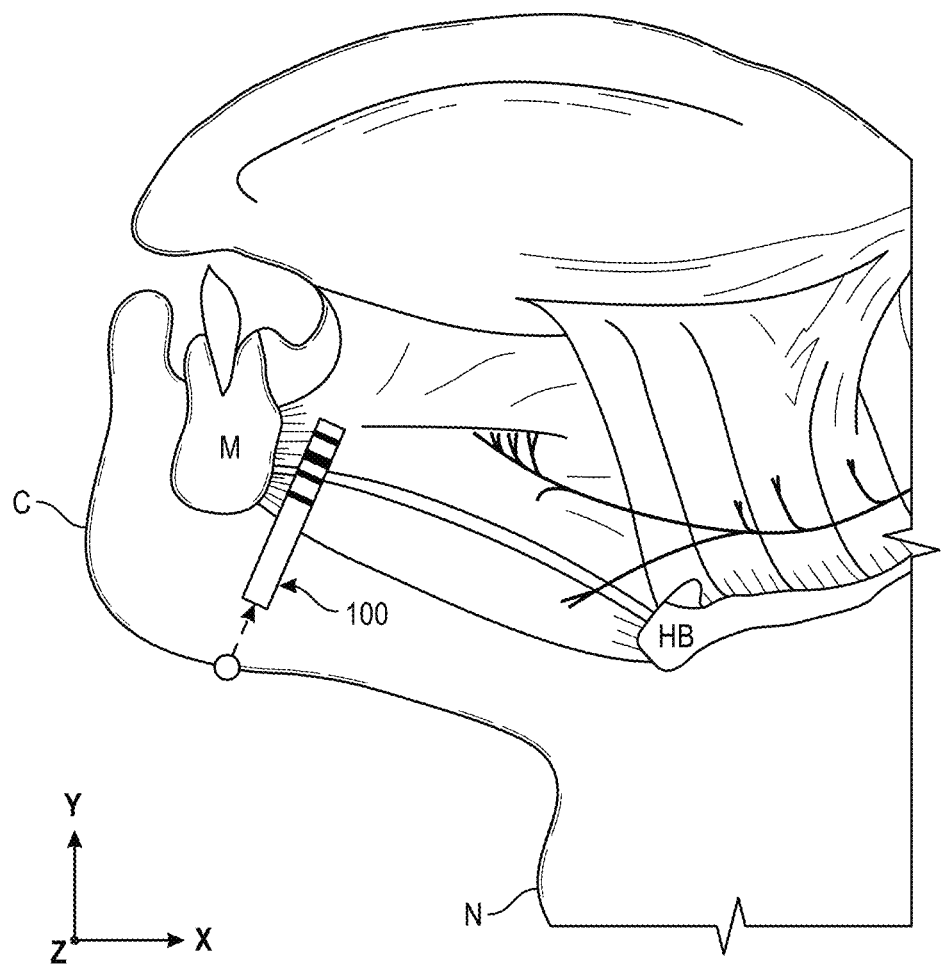
FIGS. 9A and 9B are side and submental sectional views, respectively, depicting a signal delivery device insertion path, in accordance with embodiments of the present technology.
Figure 9B:
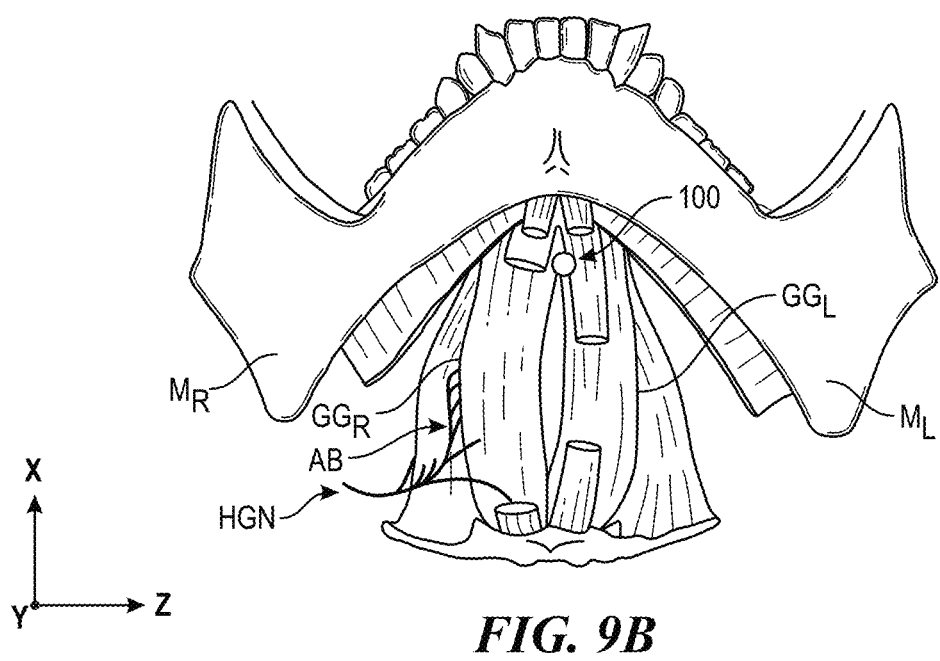

FIGS. 9A and 9B are side and submental sectional views, respectively, depicting a signal delivery device insertion path, configured in accordance with embodiments of the present technology. Referring to FIGS. 9A and 9B together, the signal delivery device 100 can be positioned between the left and right genioglossus muscles $GG_L$, $GG_R$, and in an orientation that is at least generally similar to the orientation shown in FIGS. 8A and 8B. However, in FIGS. 9A and 9B, the signal delivery device 100 is positioned further anteriorly compared to the position in FIGS. 7A and 7B. As described previously with reference to FIGS. 3A-3C, the patient's mandible M and/or chin C (FIG. 9A) can define an anterior-most bound to the positioning and/or insertion path of the signal delivery device 100, and the patient's hyoid bone HB and/or neck N (FIG. 9A) can define a posterior-most bound to the positioning of the signal delivery device 100. As described previously with reference to FIGS. 4A-4C, the left and right mandible portions $M_L$, $M_R$ of the patient's mandible M can define the lateral bounds to the positioning and/or insertion path of the signal delivery device 100.

Figure 10:
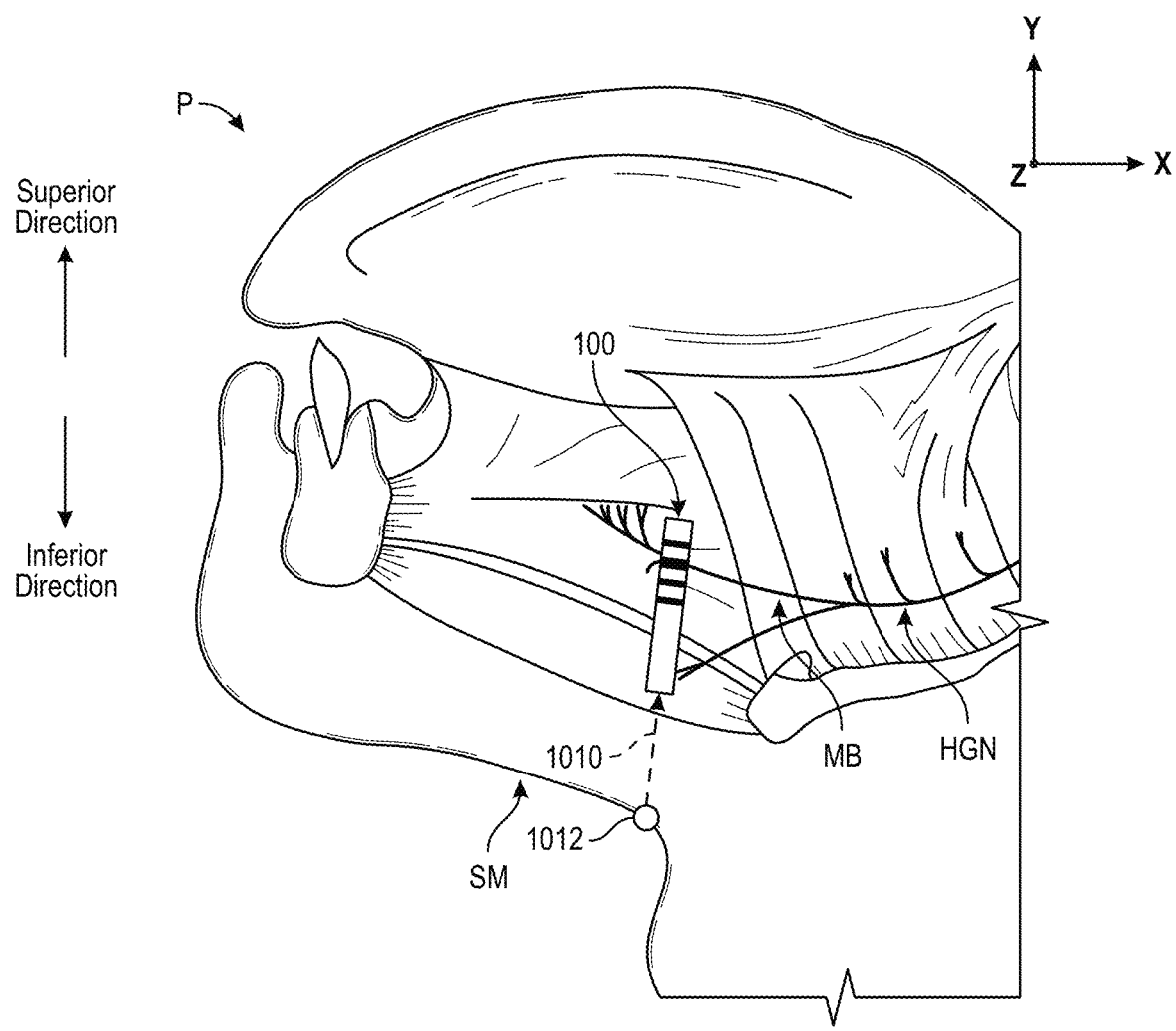
FIG. 10 is a side view depicting another signal delivery device insertion path, in accordance with embodiments of the present technology.

FIG. 10 is a side view depicting another signal delivery device insertion path 1010, oriented in accordance with embodiments of the present technology. As shown in FIG. 10, the signal delivery device 100 can be positioned to stimulate the medial branch MB or another portion of the hypoglossal nerve HGN via an insertion point 1012 formed in the submental region SM of the patient P. As described previously herein, the insertion path 1010 can be at least generally linear, or may include one or more insertion path segments that can be angled relative to one another. The insertion path 1010 can be used to advance the signal delivery device 100 anteriorly, posteriorly, medially, laterally, and/or a combination thereof.

Figure 11:
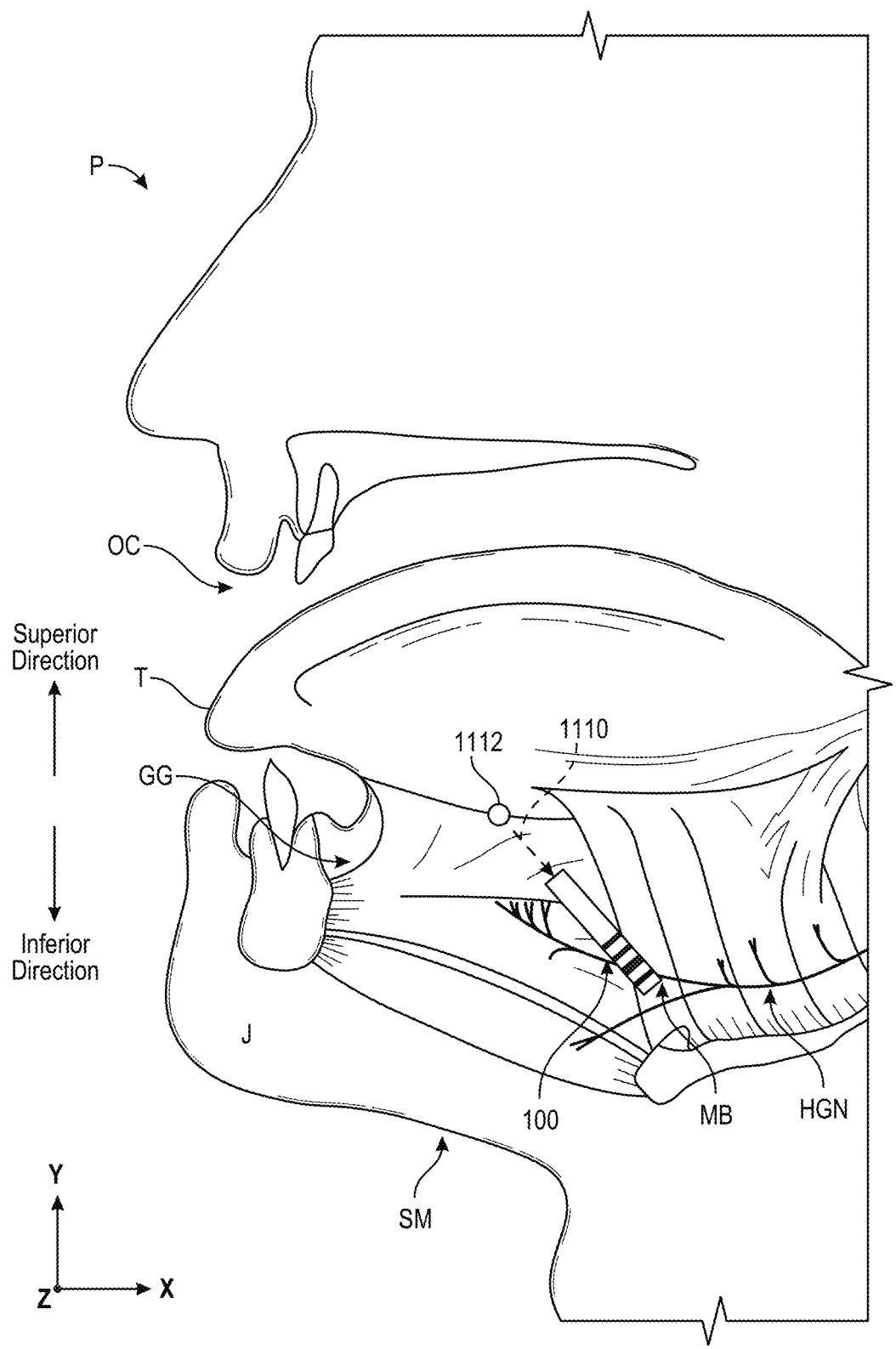
FIG. 11 is a side view depicting a further signal delivery device insertion path, in accordance with embodiments of the present technology.

FIG. 11 is a side view depicting a further signal delivery device insertion path 1110, oriented in accordance with embodiments of the present technology. As shown in FIG. 11, the signal delivery device 100 can be inserted into the patient P through the patient's oral cavity OC, such as through a sublingual opening 1112 formed in a floor of the patient's mouth. In the illustrated embodiment, the signal delivery device 100 is positioned to deliver an electrical signal to the medial branch MB of the patient's hypoglossal nerve HGN. In other embodiments, the signal delivery device 100 can be inserted through the sublingual opening 1112 and positioned to deliver the electrical signal to one or more of the anterior branches AB, another portion of the hypoglossal nerve HGN, positioned at least partially with the patient's genioglossus muscle GG, and/or at another suitable position. As described previously herein, the insertion path 1110 can be at least generally linear, or may include one or more insertion path segments that can be angled relative to one another. The insertion path 1110 can be used to advance the signal delivery device 100 anteriorly, posteriorly, medially, laterally, and/or a combination thereof.

4. Representative Experimental Data

Figure 12:
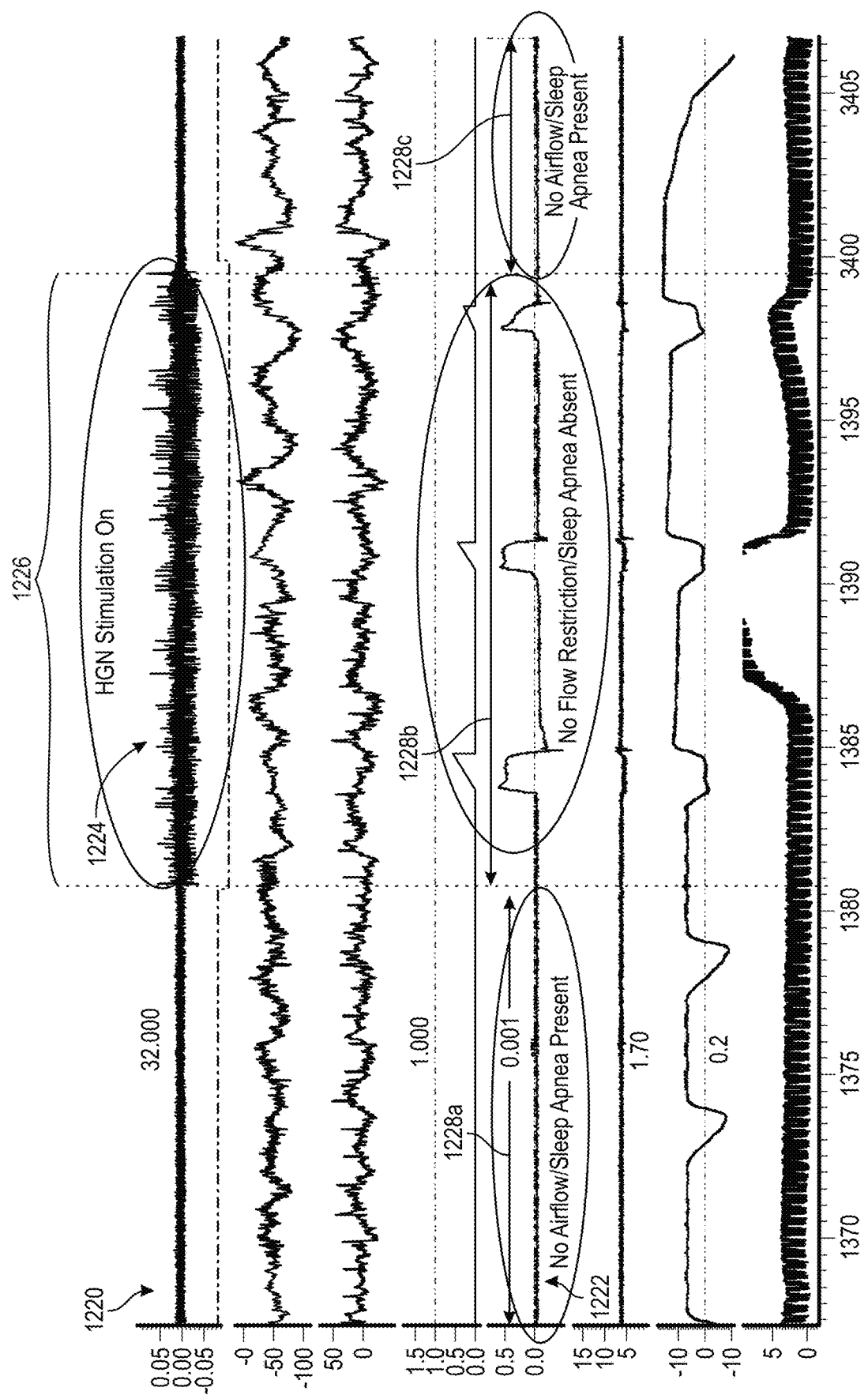
FIG. 12 illustrates plots of patient data obtained in response to delivering an electrical signal to target tissue, in accordance with embodiments of the present technology.

FIG. 12 illustrates plots of patient data obtained by directing an electrical signal to a target tissue, in accordance with embodiments of the present technology. For example, FIG. 12 includes a stimulation-over-time plot 1220 ("stimulation plot 1220") and a patient-airflow-over-time plot 1222 ("airflow plot 1222"). The stimulation plot 1220 illustrates an electrical signal 1224 delivered to the patient from a signal delivery device (e.g., the signal delivery device 100 of FIG. 1A) positioned at least generally similarly or identically to the position/orientation shown in FIG. 2A. The other positions/orientations described herein, including those described with reference to FIGS. 3A-8B, are expected to provide at least generally similar or identical results to those shown in FIG. 12.

Data in the airflow plot 1222 was obtained using drug-induced sleep endoscopy (DISE), which is a dynamic evaluation technique used to examine an individual's pattern of upper airway obstruction. For example, DISE can provide information regarding one or more areas of collapse during sleep and/or one or more specific structures and/or tissues responsible for such obstructions, including the lateral pharyngeal walls, the soft palate, the tongue, and/or the epiglottis. DISE is generally performed after a sedative agent, such as propofol or midazolam, has been administered to the patient. The sedative agent can cause flow restrictions/obstructions in the patient's airway that simulate OSA, or other apnea and/or hypopnea events. For example, administering propofol to the patient can induce pharyngeal muscle relaxation (decrease of the muscle tone) and thereby cause the patient's airway to collapse. This is shown, for example, in a pre-signal-delivery portion 1228a and a post-signal-delivery portion 1228c of the airflow plot 1222, during which the airflow plot 1222 indicates that the patient experienced fully obstructed airflow (e.g., OSA, or an apnea event). However, during a signal delivery period 1226 during which the electrical signal 1224 was delivered to the patient, a corresponding signal delivery portion 1228b of the airflow plot 1222 indicates that the airflow restriction was at least partially reduced or eliminated and/or that the patient's airflow was at least partially or fully restored.

FIG. 13 is a table including data obtained by implanting and activating a signal delivery device in accordance with embodiments of the present technology. Subjects 10-13 received a signal delivery device using an approach at least generally similar or identical to one or more of the approaches described with reference to FIGS. 2A-8B. Subjects 1-9 each received a signal delivery device using an anterior-to-posterior delivery approach, such as illustrated in FIG. 11. The Electrode Array Capture & Stability During Procedure column indicates a time during which the electrode array (e.g., the signal delivery device 100 of FIG. 1A)

remained positioned to deliver the electrical signal to the target tissue. The electrode arrays used in the present study did not include anchors or other components attached to patient tissue, and were accordingly used for short-term, rather than chronic, stimulation. As shown in FIG. 13, the approaches of the present technology used with subjects 10-13 were capable of positioning the signal delivery device with at least five times more stability than the approaches used for subjects 1-9. Accordingly, it is expected that using the anterior approach to implant devices may provide more time for the devices to be anchored and/or that the devices may include less extensive and/or lower profile anchoring components compared to devices implanted using the posterior or other approaches. Moreover, as shown by the data in the Peak Flow Amplitude Increase Stim/No Stim column, the approaches of the present technology used for subjects 10-13 were at least as effective, if not more effective, at increasing patient airflow and/or otherwise reducing/eliminating airflow restrictions/obstructions. The entry "N/A" indicates patients with CCC and for whom airflow measurements were not obtained.

5. Additional Devices, Systems, and Methods

Figure 14:
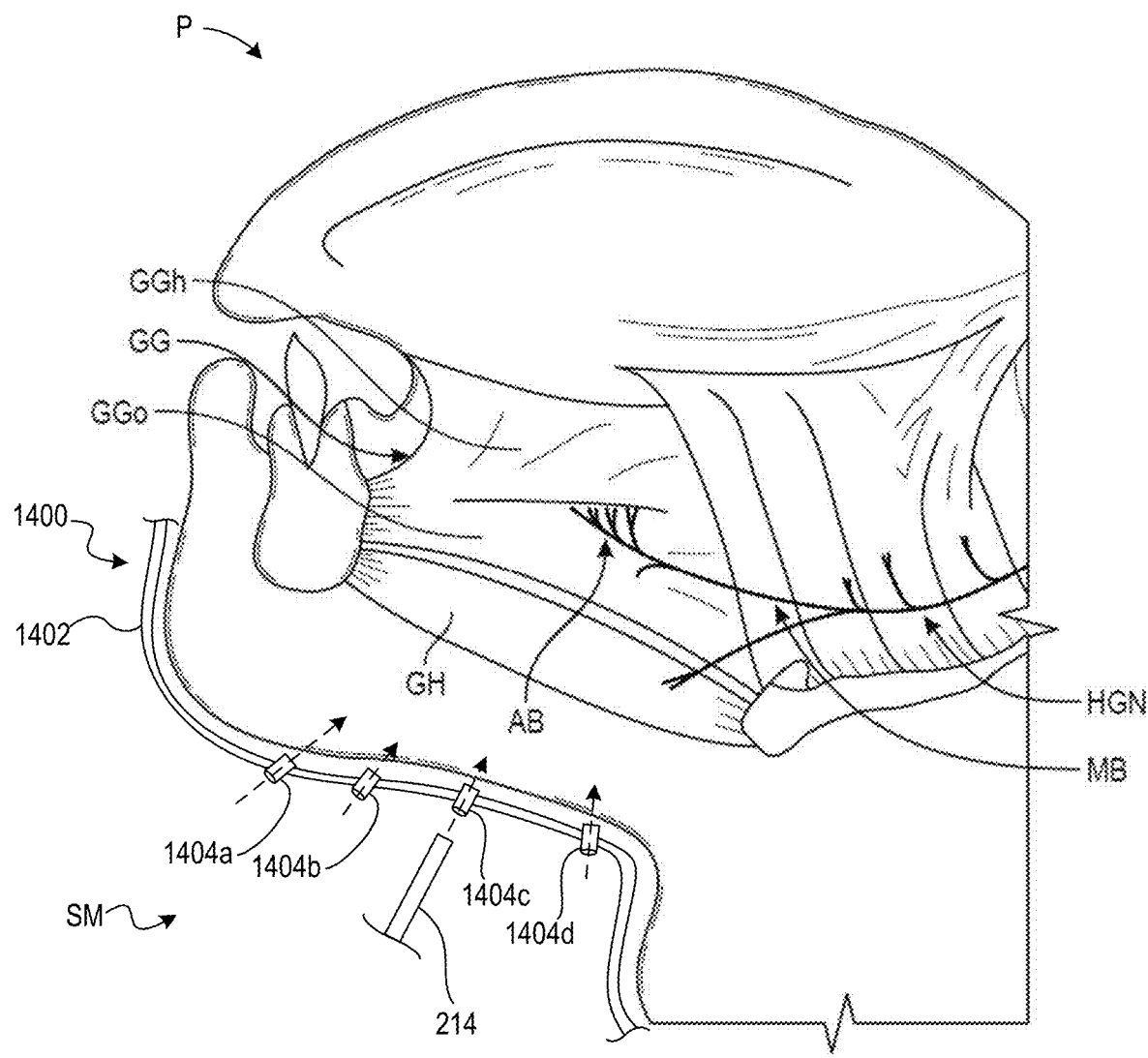
FIG. 14 is a side view of a portion of a patient's upper airway depicting an insertion guide configured in accordance with embodiments of the present technology.

FIG. 14 is a cross-sectional side view of a portion of a patient's upper airway depicting an insertion guide 1400 configured in accordance with embodiments of the present technology. The insertion guide 1400 can include a body or support structure 1402 and one or more alignment features 1404 (individually identified as a first alignment feature 1404a, a second alignment feature 1404b, a third alignment feature 1404c, and a fourth alignment feature 1404d). The support structure 1402 can be positioned on/over, and/or can be configured to conform to (e.g., deform elastically to) at least a portion of the patient's submental region SM. The support structure 1402 can be customized to the patient's specific anatomy and/or can be adjustable to fit a range of patient anatomies. In some embodiments, the support structure 1402 can be coupled and/or secured to the patient P, e.g., via adhesive, one or more straps, a collar and/or neck brace, etc. In other embodiments, the support structure 1402 can be placed on the patient P and can rely on friction and/or the conformability to the patient's anatomy to prevent, or at least partially prevent, the support structure 1402 from moving relative to the patient P. Each of the alignment features 1404 can at least partially define an insertion path that can be used to position a signal delivery device at least proximate to target tissue, including the anterior branches AB of the hypoglossal nerve HGN, the genioglossus muscle GG, and/or any other target tissue described herein. In the illustrated embodiment, the alignment features 1404 are ports extending through the support structure 1402. The insertion tool 214 can then be positioned through/within individual ports 1404. Additionally, or alternatively, individual ones of the alignment features 1404 can include tooling holes, lasers, and/or other suitable alignment features. In these and other embodiments, the alignment features 1404 can be configured to control an insertion depth of the tool 214, e.g., by having a narrowed internal diameter, including a stopping surface, and/or another feature configured to contact the tool 214 at a predetermined insertion depth. In some embodiments, the insertion guide 1400 can be used to implant one or more signal delivery devices without the aid of the ultrasound probe 201 (FIG. 2A), which is expected to further increase the speed with which the signal delivery devices can be implanted.

Figure 15:
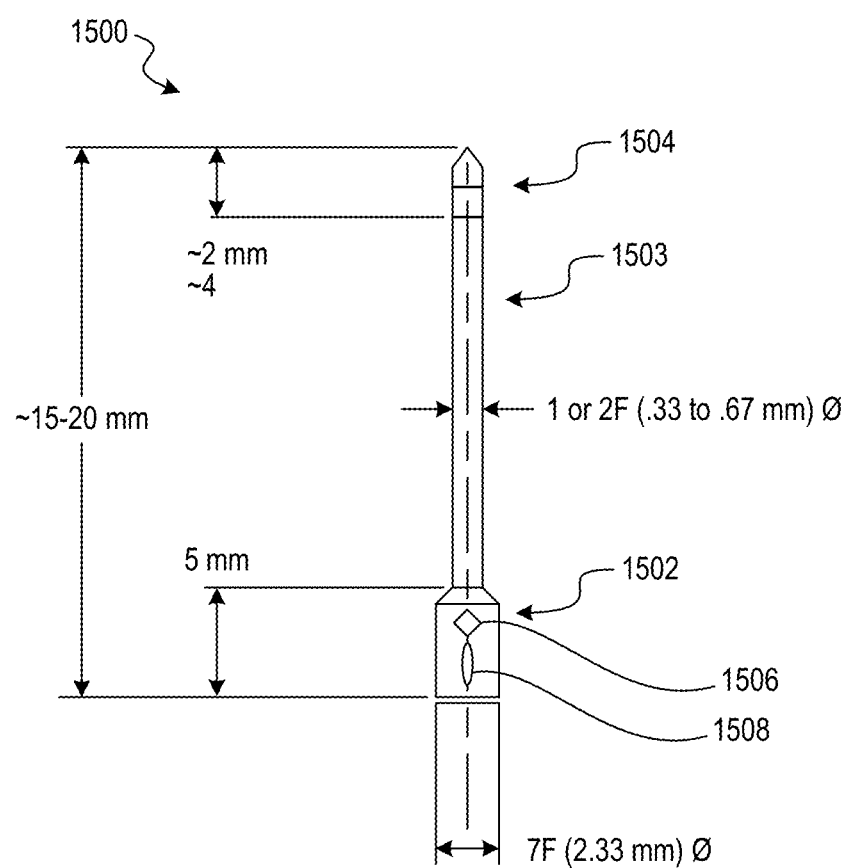
FIG. 15 is a partially schematic side view illustrating another signal delivery device configured in accordance with embodiments of the present technology.

FIG. 15 is a partially schematic side view illustrating another signal delivery device 1500 configured in accordance with embodiments of the present technology. The dimensions shown in FIG. 15 are for illustration purposes only and, in at least some embodiments, all or one or more portions of the signal delivery device 1500 can have dimensions other than those shown in FIG. 15. In at least some embodiments, the signal delivery device 1500 can be at least generally similar or identical in structure and/or function to the signal delivery device 100 of FIG. 1A. For example, the illustrated signal delivery device 1500 includes a housing 1502, an electrode array 1504 coupled to the housing 1502, a signal generator 1506, and an antenna 1508. The electrode array 1504 can include a monopolar electrode array or a bipolar (or other multi-polar) electrode array. In some embodiments, the electrode array 1504 can include electrodes formed from Pt and/or Ir, such as Pt90/Ir10, and/or one or more other suitable materials. The housing 1502 can be configured to hermetically contain one or more circuit components of the signal delivery device 1500, including the signal generator 1506 and/or the antenna 1508. All or a portion of the housing 1502 can be formed from Pt, PtIr, Ti6AL4V, epoxy, a TPE, one or more ceramics, and/or one or more other suitable materials. For example, a portion of the housing 1502 surrounding the antenna 1508 can be formed from epoxy, ceramic, and/or TPE, e.g., to prevent, or at least partially prevent, interference with power transmission to the antenna 1508. Optionally, at least a portion of the housing 1502 can be electrically activatable and configured to serve as an electrode, e.g., when the electrode array 1504 is monopolar.

Additionally, the signal delivery device 1500 includes a lead portion 1503 coupled to the housing 1502 and carrying the electrode array 1504. The lead portion 1503 can be at least generally flexible and/or otherwise configured to undergo elastic deformation. In some embodiments, the lead portion 1503 is separable from the housing 1502 and configured to be coupled to and/or docked with the housing 1502, e.g., in vivo. In some embodiments, the lead portion 1503 can be formed from one or more thermoplastic polyurethanes (TPUs), such as Tecothane™, and/or one or more other suitable materials. The lead portion 1503 can contain one or more wires and/or other conductive elements that electrically couple the electrode array 1504 to the signal generator 1506. The wires/conductive elements can be formed from MP35N and/or one or more other suitable conductive materials.

Figure 16:
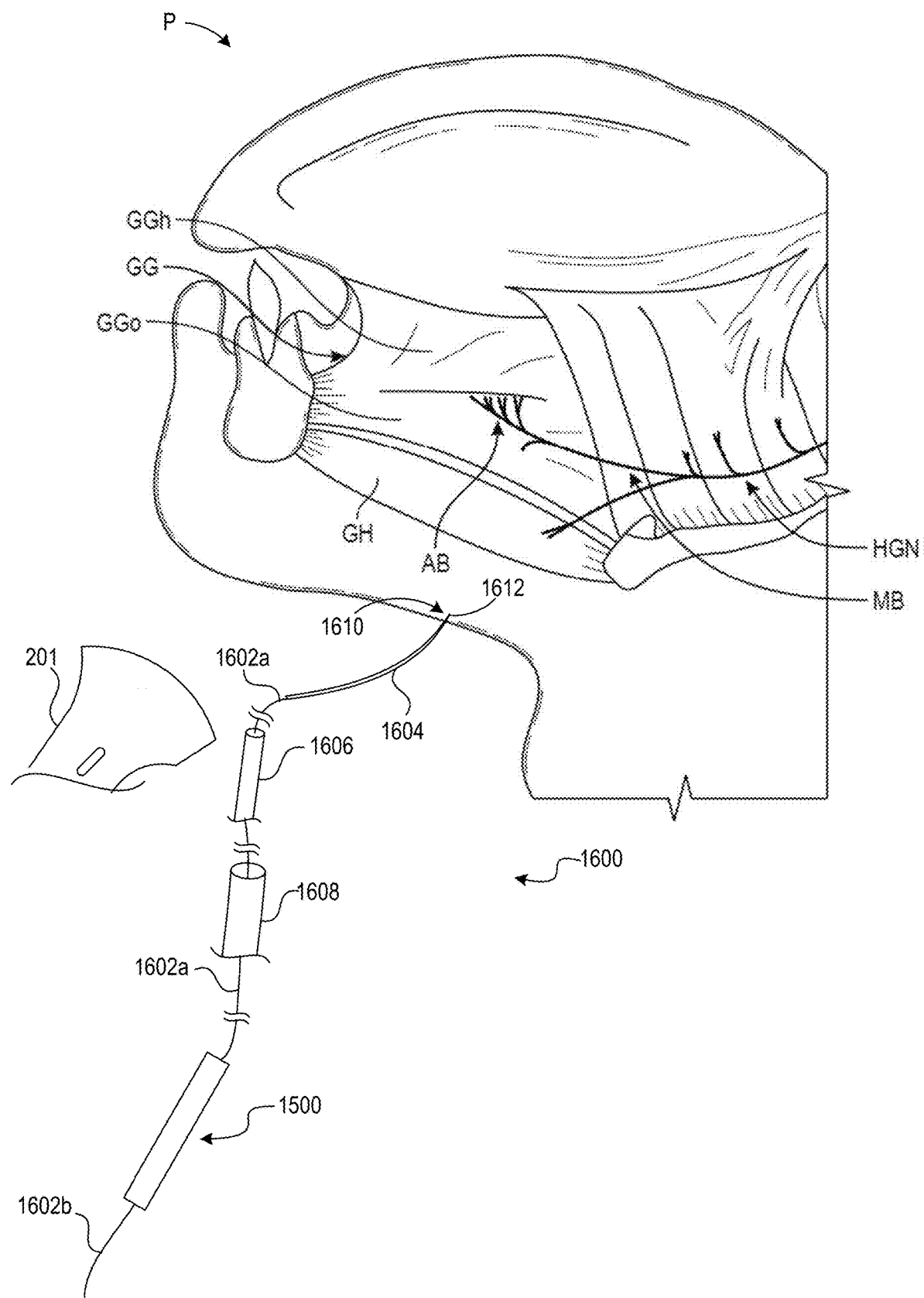
FIG. 16 illustrates a representative set of implant tools used to implant a signal delivery device in accordance with embodiments of the present technology.

FIG. 16 illustrates a representative set of implant tools 1601 used to implant a signal delivery device 1600 in accordance with embodiments of the present technology. The signal delivery device 1600 can include at least some features that are at least generally similar or identical in structure and/or function to the signal delivery device 100 (FIG. 1A) and/or the signal delivery device 1500 (FIG. 15).

In operation, one end of the signal delivery device 1600 is attached to a proximal suture thread 1602a, and the opposite end is attached to a distal suture thread 1602b. The proximal suture thread 1602a is attached to a needle 1604, which can be curved (as shown in FIG. 16), helical, or straight. Depending upon the dimensions of the signal delivery device 1600, the implant tools can further include a dilator 1606, an introducer 1608, which can include a cannula through which the signal delivery device 1600 can be positioned within the patient, and/or other percutaneous insertion device(s) configured to facilitate directing the signal delivery device 1600 into the opening formed by the needle 1604, such as via the Seldinger method. For example, the introducer 1608 can form a percutaneous insertion pathway through the patient's skin and through which the signal delivery device 1600 can be percutaneously inserted, implanted, injected, and/or the like.

Whether the needle 1604 is curved (as shown in FIG. 16) or straight (as may be the case in other embodiments), the needle can have a diameter in a range of from 20 gage to 10 gage, or 18 gage to 12 gage in particular embodiments. The dilator 1606 can have a diameter in a range of from 3 Fr to 12 Fr (1 mm to 4 mm).

The needle 1604 and/or introducer 1608 can be inserted in the patient P using any of the insertion paths and/or openings described herein, e.g., with reference to FIGS. 2A-11. In some embodiments, the needle 1604 and/or another percutaneous insertion device can be configured to stimulate the patient's tissues during insertion. For example, as shown in FIG. 16, the needle 1604 can include one or more electrodes 1610 positioned at or proximate to a terminus 1612 of the needle 1604. The precise location of the needle 1604 can be identified by delivering electrical stimulation to the patient via the needle and observing the patient's motor response. The practitioner can use ultrasound (e.g., the ultrasound probe 201) and/or another suitable visualization technique, in addition to or in lieu of inducing a motor response. Accordingly, in at least some embodiments, the practitioner can use a combination of visual navigation and stimulation-response navigation to precisely align the needle 1604 relative to the stimulation target. As discussed above, the target can include the anterior branches AB of the hypoglossal nerve HGN, another portion of the hypoglossal nerve HGN (e.g., the medial branch MB), the genioglossus muscle GG and/or one or more of the fiber portions GGo, GGh thereof, and/or another suitable target location. Accordingly, when the signal delivery device 1600 is introduced, the signal delivery device 1600 is expected to be closer to and/or more closely aligned with the target location. In some embodiments, a practitioner can use stimulation-response navigation to identify the needle's position when operating in portions of the patient's anatomy in which the needle 1604 is difficult to visualize (using, e.g., ultrasound), such as proximate to/within the anterior branches AB of the hypoglossal nerve HGN.

Depending on the embodiment, the foregoing elements (e.g., the needle 1604, the dilator 1606, the introducer 1608, etc.) can be removed axially and/or can be pre-slitted and peeled off. In operation, the needle 1604 is directed into the patient's tissue at a first point, forming a first opening. The needle 1604 can exit the patient's tissue at a second point, forming a second opening. The practitioner can then pull the signal delivery device 1600 through the first opening via the needle 1604, and use the proximal and distal suture threads 1602a, 1602b to more precisely locate signal delivery device 1600 within the patient. In some embodiments, the signal delivery device 1600 can be activated within the patient P to deliver one or more electrical signals to the patient's tissues to confirm that the signal delivery device 1600 is positioned at least proximate to the target tissue.

In some embodiments, the needle 1604 can be hollow such that the signal delivery device 1600 can be positioned within the patient by inserting the signal delivery device 1600 through the needle 1604 and percutaneously into the patient, with or without using the suture threads 1602a, 1602b, and/or via a single opening. In these and other embodiments, one or more other percutaneous insertion devices, such as the introducer 1608, the dilator 1606, and/or a cannula, can be inserted over the needle 1604 to assist with the percutaneous insertion of the signal delivery device 1600. For example, the needle 1604 can be used to stimulate tissue to identify an implant site and facilitate placement of one or more dilators and/or cannulas over the needle 1604. In this way, the needle 1604 can be used to position a cannula configured to deliver the signal delivery device 1600 to the implant site. In these and other embodiments, the needle 1604 can optionally include a lumen and/or an atraumatic tip. In at least some embodiments, the needle 1604 can be configured to operate as a dilator and deliver a cannula directly, such that the dilator 1606 can be omitted.

Figure 17:
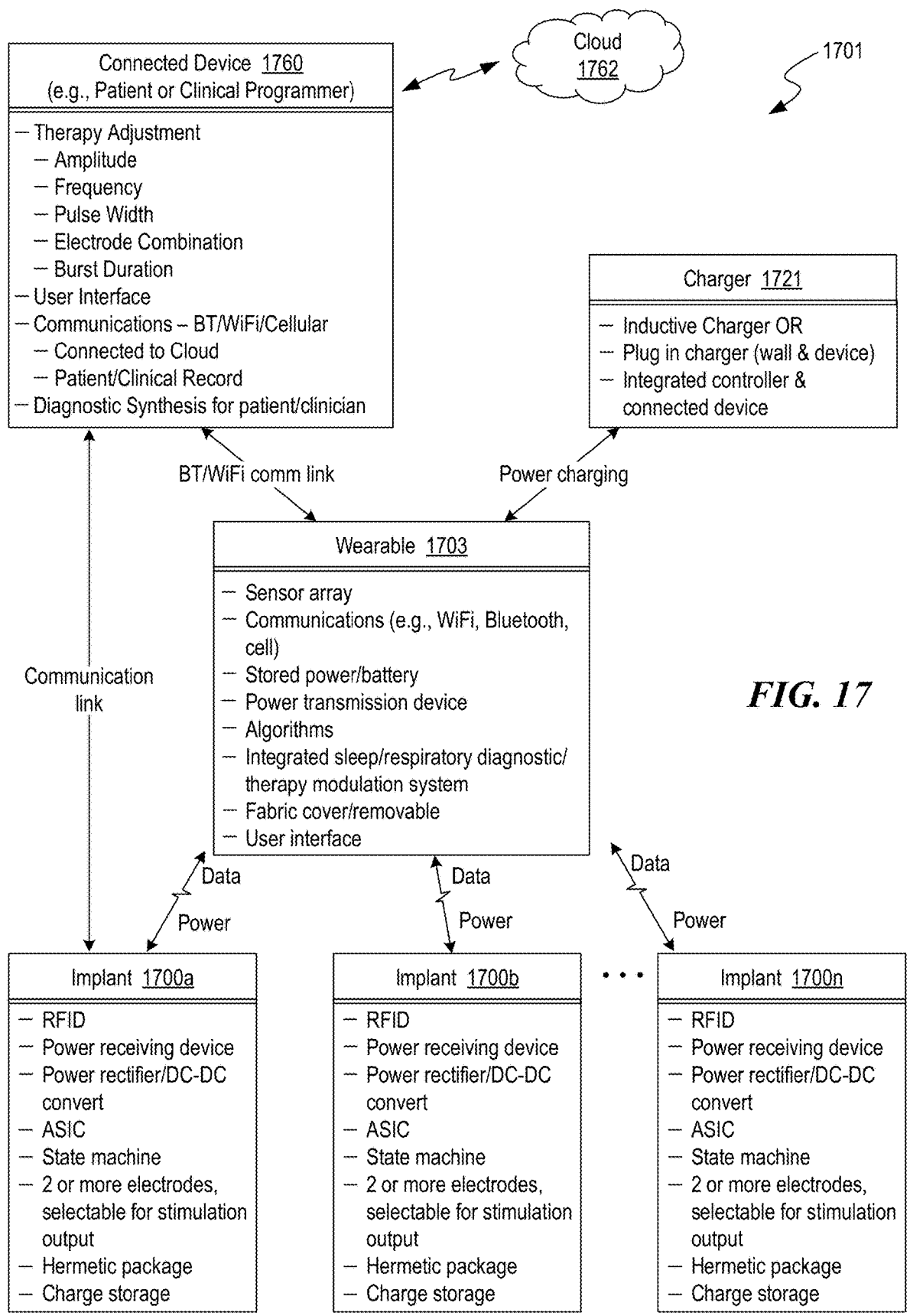
FIG. 17 is a block diagram illustrating elements of a system for treating sleep disorders in accordance with embodiments of the present technology.

FIG. 17 is a block diagram illustrating elements of a system 1701 for treating sleep disorders in accordance with embodiments of the present technology. The system 1701 can include a wearable device 1703, a charger 1721, one or more implants or implantable devices (e.g., a first implantable device 1700a, a second implantable device 1700b . . . an $n^{th}$ implantable device 1700n; referred to collectively as "implantable devices 1700") and a connected device or programmer 1760. In general, the programmer 1760 can transmit instructions for generating an electrical signal (e.g., signal delivery or waveform parameters) to the wearable device 1703, the wearable device 1703 can transmit the instructions and power to the implantable device(s) 1700, and individual ones of the implantable devices 1700 can generate the electrical signal according to the transmitted instructions and apply the electrical signal to a patient via electrodes carried by the implantable device(s) 1700. Individual ones of the implantable devices 1700 can be at least generally similar or identical in structure and/or function to the signal delivery device 100 of FIG. 1A, the signal delivery device 1500 of FIG. 15, the signal delivery device 1600 of FIG. 16, and/or other signal delivery devices. Additionally, individual ones of the implantable devices 1700 can be implanted in a patient using one or more of the insertion paths, in one or more of the positions and/or orientations, and/or to deliver an electrical signal to one or more portions of the hypoglossal nerve HGN (includes the anterior branches AB and/or the distal brachiated portions DB thereof) and/or the genioglossus muscle GG described previously with reference to FIGS. 2A-11.

The programmer 1760 can include a patient-operated programmer and/or a clinician-operated programmer and can be configured to control one or more characteristics of the electrical signal delivered to the patient. In a representative embodiment, the programmer 1760 can include a therapy adjustment module configured to select individual ones of the electrodes carried by the implantable device(s) 1700 and adjust (e.g., increase or decrease) an amplitude, frequency, pulse width, a burst duration, whether the electrode is active or inactive, and/or any other suitable signal delivery parameter. Additionally, the programmer 1760 can synthesize information (e.g., diagnostic and/or feedback information) received from a user, the wearable 1703, and/or individual ones of the implantable devices 1700 and can adjust one or more of the signal delivery parameters based at least partially on the synthesized information. For example, the programmer 1760 can be configured to direct the electrical signal to specific distal brachiated portions DB based, at least in part, on a tissue collapse pattern of the patient, as described previously with reference to FIGS. 5A-6C.

The programmer 1760 can transmit the signal delivery parameters to the implantable device(s) 1700 directly and/or via the wearable device 1703. For example, the programmer 1760 can be connected to individual ones of the implantable devices 1700 and/or the wearable device 1703 via a wired or wireless communication link, such as WiFi, Bluetooth ("BT"), cellular connectivity, and/or any other suitable communication link. In these and other embodiments, the programmer 1760 can be connected to a cloud 1762 and/or other computer service, e.g., to upload data received from the wearable device's 1703 sensors and/or to download information to the wearable device 1703 and/or the implantable device(s) 1700. In these and other embodiments, the programmer 1760 can include a display and/or a user interface. A user (e.g., the patient, the clinician, and/or other suitable user) can interact with and/or otherwise control one or more aspects of the programmer 1760 via the user interface, e.g., to manually adjust one or more of the signal delivery parameters, to read data received from the wearable device 1703 sensors, provide one or more inputs corresponding to a tissue collapse pattern, and/or carry out other tasks.

The wearable device 1703 can include a collar, chinstrap, mouthpiece, pillow, and/or can have other suitable form factors. The wearable device 1703 can include one or more sensors (e.g., a single sensor, an array of sensors, and/or other suitable sensor arrangements) configured to collect data associated with a patient. Representative data received from the patient can include respiratory rate, sleep state, wake state, heart rate, audio signals (corresponding to audible snoring, hypopnea events, and/or apnea events), body temperature, head orientation/position, saturated blood oxygen levels, air flow levels, thyroid movement, trachea movement, and/or tongue movement, photoplethysmography (PPG) data, among others, each of which can be received by a corresponding type of sensor (e.g., heart rate data from a heart rate sensor, head orientation/position data from an accelerometer, etc.). The received data can correspond to a measure of the patient's respiratory performance, sleep state, wake state, and/or other suitable metrics, for example, metrics that are used to rate the patient on the Apnea-Hypopnea Index (AHI).

The wearable device can further include a power source (e.g., a stored power device such as battery), a power transmission component configured to transmit power and/or signal delivery parameters to the implantable device(s) 1700, and one or more algorithms configured to control one or more aspects of the operation of the wearable device 1703. Individual ones of the sensors can collect data associated with the patient, such as a patient's sleep state and/or respiratory performance. The one or more algorithms can be configured to adjust at least one of the signal delivery parameters based at least partially on the data collected by the sensors. In a representative embodiment, the wearable 1703 can include an integrated sleep, respiratory diagnostics, and/or therapy modulation system configured to adjust or otherwise control one or more delivery parameters of the electrical signal delivered to the patient based on the collected sleep state and/or respiratory performance data, e.g., via one of more algorithms.

In some embodiments, the wearable device 1703 can further include a cover or housing, at least a portion of which may be removeable, e.g., to expose an interior or interior portion of the wearable device 1703. In these and other embodiments, the wearable device 1703 cover can include fabric, or any other suitable material. Optionally, the wearable device 100 can include a reduced and/or simplified user interface configured to allow a user to interact with and/or otherwise control one or more of the elements of the wearable device 1703 (e.g., check a charging status of the power source, adjust one or more of the signal delivery parameters, etc.).

The charger 1721 for the wearable device 1703 can be configured to supply power to the wearable device's 1703 power source. The charger 1721 can include a wireless (e.g., inductive) charger, a wired charger (e.g., wall-plug, charging cable, etc.), and/or any other suitable charger or charging device. Optionally, the charger 1721 can include an integrated controller and/or a connected device, e.g., to control the charging of the wearable device 1703 and/or to upload/download data to the wearable device 1703 while the wearable device 1703 is charging.

Individual ones of the one or more implantable devices 1700 can include an RFID component (e.g., a unique RFID tag that can be used to identify and/or locate the associated implantable device 1700*a*-*n*), a power receiving device (e.g., one or more RF power antennas, one or more inductive coils, etc.), a power rectifier/DC-DC converter, circuitry (e.g., one or more application-specific integrated circuits (ASICs), a state machine, etc.), a signal generator, and two or more electrodes that are each individually selectable to deliver an electrical signal to a patient. The power receiving device can receive power from the power transmission component (e.g., one or more RF power antennas, one or more inductive coils, etc.) of the wearable device. The power rectifier/DC-DC converter can be operably coupled to the electrode receiver antenna and can be configured to transmit the received power to the signal generator. Additionally, each of the implantable devices 1700 can receive, via the power receiving device and/or one or more other communication components, information regarding one or more of the delivery parameters of the electrical signal to be generated by the signal generator and/or delivered to the patient via at least one of the electrodes of the implantable device(s) 1700. The circuitry can include machine-readable instructions associated with the operation of the implantable device(s) 1700. For example, the circuitry can include instructions that, when executed, can cause the signal generator to generate the electrical signal having the signal delivery parameter(s) received via the electrode receiver antenna. In these and other embodiments, the power receiving device and/or the one or more other communication components can be used to transmit information associated with the implantable device 1700 to the wearable device 1703. For example, the implantable device 1700 information to the wearable device 1703 associated with one or more of the signal delivery parameters of the electrical signal being applied to the patient. In these and other embodiments, individual ones of the one or more implantable devices 1700 can include a hermetic package or housing configured such that the implantable device(s) 1700 can be implanted within a patient.

6. Examples

The following examples provide further embodiments of the present technology:

1. A method for addressing a patient's sleep apnea, the method comprising:
   percutaneously inserting a signal delivery device into the patient at a submandibular insertion point;
   advancing the signal delivery device in an at least partially superior direction toward a target location; and
   implanting the signal delivery device at least proximate to the target location with the signal delivery device having an orientation, with at least a vector component of the orientation aligned along an inferior-superior axis, and wherein the signal delivery device includes at least one electrode configured to deliver a signal to the target location.

2. The method of example 1 wherein implanting the signal delivery device at least proximate to the target location includes implanting the signal delivery device proximate to or within a genioglossus muscle of the patient.

3. The method of example 1 wherein implanting the signal delivery device at least proximate to the target location includes positioning at least a portion of the signal delivery device between a left genioglossus muscle of the patient and a right genioglossus muscle of the patient.

4. The method of example 1 wherein implanting the signal delivery device at least proximate to the target location includes implanting the signal delivery device proximate to a hypoglossal nerve of the patient.

5. The method of example 4 wherein implanting the signal delivery device proximate to the hypoglossal nerve includes implanting the signal delivery device proximate to a medial branch of the hypoglossal nerve.

6. The method of example 1 wherein implanting the signal delivery device at least proximate to the target location includes positioning at least a portion of the signal delivery device distal from the medial branch of a hypoglossal nerve of the patient.

7. The method of example 1 wherein implanting the signal delivery device at least proximate to the target location includes implanting the signal delivery device proximate to one or more anterior branches of a hypoglossal nerve of the patient.

8. The method of example 7 wherein implanting the signal delivery device proximate to the one or more anterior branches of the hypoglossal nerve includes implanting the signal delivery device proximate to at least one motor end plate of the hypoglossal nerve.

9. The method of example 7 wherein implanting the signal delivery device proximate to the one or more anterior branches of the hypoglossal nerve includes implanting the signal delivery device between (i) a first end of the one or more anterior branches at which individual ones of the one or more anterior branches innervate a genioglossus muscle of the patient, and (ii) a second end of the one or more anterior branches at which individual ones of the one or more anterior branches divide from a medial branch of the hypoglossal nerve.

10. The method of example 1 wherein implanting the signal delivery device at least proximate to the target location includes implanting the signal delivery device transverse to a plurality of anterior branches of a hypoglossal nerve of the patient.

11. The method of example 1 wherein advancing the signal delivery device includes advancing the signal delivery device in an at least partially anterior-to-posterior direction and/or an at least partially posterior-to-anterior direction.

12. The method of example 1 wherein advancing the signal delivery device includes advancing the signal delivery device in an at least partially medial-to-lateral direction and/or an at least partially lateral-to-medial direction.

13. The method of example 1, further comprising delivering the signal to the target location to at least partially address the patient's sleep apnea.

14. The method of example 13 wherein the signal is a first signal delivered at a first time, wherein delivering the first signal includes inducing a first motor response in the patient, the method further comprising delivering a second signal to the target location at a second time to induce a second motor response greater than the first motor response.

15. The method of example 14 wherein the target location includes a genioglossus muscle of the patient.

16. The method of example 15 wherein advancing the signal delivery device includes advancing the signal delivery device along a single, at least generally linear path from the submandibular insertion point to the target location.

17. The method of example 1 wherein implanting the signal delivery device includes implanting the signal delivery device with at least a portion of the signal delivery device positioned (i) laterally from a genioglossus muscle of the patient and (ii) inferiorly from a hyoglossus muscle of the patient.

18. The method of example 1 wherein implanting the signal delivery device includes percutaneously implanting the signal delivery device without dissecting tissue at a submental region of the patient.

19. The method of example 1, further comprising causing the signal delivery device to deliver the signal to determine a location of the signal delivery device relative to the target location.

20. A method for addressing a patient's sleep apnea, the method comprising:
   percutaneously inserting a signal delivery device into the patient at a submandibular insertion point with the signal delivery device having an orientation, with at least a vector component of the orientation aligned along an inferior-superior axis;
   advancing the signal delivery device in an at least partially superior direction toward a plurality of anterior branches of a hypoglossal nerve of the patient; and
   implanting the signal delivery device at least proximate and transverse to the plurality of anterior branches with at least one electrode of the signal delivery device positioned to deliver an electrical signal to the plurality of anterior branches.

21. The method of example 20 wherein advancing the signal delivery device in the at least partially superior direction includes advancing the signal delivery device in an at least partially anterior-to-posterior direction and/or an at least partially posterior-to-anterior direction.

22. The method of example 20 wherein advancing the signal delivery device in the at least partially superior direction includes advancing the signal delivery device in an at least partially medial-to-lateral direction and/or an at least partially lateral-to-medial direction.

23. The method of example 20 wherein advancing the signal delivery device includes advancing the signal delivery device in the orientation.

24. The method of example 20 wherein implanting the signal delivery device includes implanting the signal delivery device in the orientation.

25. A method for addressing a patient's sleep apnea, the method comprising:
   percutaneously inserting a signal delivery device into the patient via a submandibular insertion point with the signal delivery device having an orientation, with at least a vector component of the orientation aligned along an inferior-superior axis;
   advancing the signal delivery device in an at least partially superior direction toward a genioglossus muscle of the patient; and
   implanting the signal delivery device at least proximate to the genioglossus muscle with at least one electrode of the signal delivery device positioned to deliver an electrical signal to at least a portion of the genioglossus muscle.

26. The method of example 25 wherein advancing the signal delivery device in the at least partially superior direction includes advancing the signal delivery device in an at least partially anterior-to-posterior direction and/or an at least partially posterior-to-anterior direction.

27. The method of example 25 wherein advancing the signal delivery device in the at least partially superior direction includes advancing the signal delivery device in an at least partially medial-to-lateral direction and/or an at least partially lateral-to-medial direction.

28. The method of example 25, further comprising:
at a first time, delivering a first signal to the portion of the genioglossus muscle to induce a first motor response of the genioglossus muscle; and
at a second time, delivering a second signal to the portion of the genioglossus muscle to induce a second motor response of the genioglossus muscle, the second motor response greater than the first motor response.

29. The method of example 25 wherein advancing the signal delivery device includes advancing the signal delivery device in the orientation.

30. The method of example 25 wherein implanting the signal delivery device includes implanting the signal delivery device in the orientation.

31. The method of example 25 wherein implanting the signal delivery device at least proximate to the genioglossus muscle includes implanting the signal delivery device with at least a portion of the signal delivery device positioned within the genioglossus muscle.

32. The method of example 25 wherein implanting the signal delivery device at least proximate to the genioglossus muscle includes implanting the signal delivery device with at least a portion of the signal delivery device positioned between a left genioglossus muscle of the patient and a right genioglossus muscle of the patient.

33. A method for addressing a patient's sleep apnea, the method comprising:
percutaneously inserting a signal delivery device into the patient at an insertion point;
advancing the signal delivery device toward a target location; and
implanting the signal delivery device at least proximate to the target location with the signal delivery device having an orientation, with at least a vector component of the orientation aligned along an inferior-superior axis, and wherein the signal delivery device includes at least one electrode configured to deliver a signal to the target location.

34. The method of example 33 wherein percutaneously inserting the signal delivery device into the patient at the insertion point includes percutaneously inserting the signal delivery device into the patient at an intraoral insertion point.

35. The method of example 33 wherein percutaneously inserting the signal delivery device into the patient at the insertion point includes percutaneously inserting the signal delivery device into the patient at a submandibular insertion point.

36. The method of any of examples 33-35 wherein implanting the signal delivery device at least proximate to the target location includes implanting the signal delivery device proximate to or within a genioglossus muscle of the patient.

37. The method of any of examples 33-35 wherein implanting the signal delivery device at least proximate to the target location includes positioning at least a portion of the signal delivery device between a left genioglossus muscle of the patient and a right genioglossus muscle of the patient.

38. The method of any of examples 33-35 wherein implanting the signal delivery device at least proximate to the target location includes implanting the signal delivery device proximate to a hypoglossal nerve of the patient.

39. The method of example 38 wherein implanting the signal delivery device proximate to the hypoglossal nerve includes implanting the signal delivery device proximate to a medial branch of the hypoglossal nerve.

40. The method of any of examples 33-35 wherein implanting the signal delivery device at least proximate to the target location includes positioning at least a portion of the signal delivery device distal from the medial branch of a hypoglossal nerve of the patient.

41. The method of any of examples 33-35 wherein implanting the signal delivery device at least proximate to the target location includes implanting the signal delivery device proximate to one or more anterior branches of a hypoglossal nerve of the patient.

42. The method of example 41 wherein implanting the signal delivery device proximate to the one or more anterior branches of the hypoglossal nerve includes implanting the signal delivery device proximate to at least one motor end plate of the hypoglossal nerve.

43. The method of example 41 wherein implanting the signal delivery device proximate to the one or more anterior branches of the hypoglossal nerve includes implanting the signal delivery device between (i) a first end of the one or more anterior branches at which individual ones of the one or more anterior branches innervate a genioglossus muscle of the patient, and (ii) a second end of the one or more anterior branches at which individual ones of the one or more anterior branches divide from a medial branch of the hypoglossal nerve.

44. The method of any of examples 33-35 wherein implanting the signal delivery device at least proximate to the target location includes implanting the signal delivery device transverse to a plurality of anterior branches of a hypoglossal nerve of the patient.

45. The method of any of examples 33-35 wherein advancing the signal delivery device includes advancing the signal delivery device in an at least partially anterior-to-posterior direction and/or an at least partially posterior-to-anterior direction.

46. The method of any of examples 33-35 wherein advancing the signal delivery device includes advancing the signal delivery device in an at least partially medial-to-lateral direction and/or an at least partially lateral-to-medial direction.

47. The method of any of examples 33-35, further comprising delivering the signal to the target location to at least partially address the patient's sleep apnea.

48. The method of example 47 wherein the signal is a first signal delivered at a first time, wherein delivering the first signal includes inducing a first motor response in the patient, the method further comprising delivering a second signal to the target location at a second time to induce a second motor response greater than the first motor response.

49. The method of example 48 wherein the target location includes a genioglossus muscle of the patient.

50. The method of example 49 wherein advancing the signal delivery device includes advancing the signal delivery device along a single, at least generally linear path from the insertion point to the target location.

51. The method of example 33 wherein advancing the signal delivery device includes advancing the signal delivery device in an at least partially superior direction.

52. The method of example 33 wherein advancing the signal delivery device includes advancing the signal delivery device in an at least partially inferior direction.

53. One or more non-transitory, computer-readable media carrying instructions that, when executed by one or more processors of a controller for an implantable signal delivery device, cause the controller to perform a method comprising:
  directing an electrical signal to be delivered by one or more electrodes carried by the implantable signal delivery device for delivery to a target tissue of a patient, wherein the implantable signal delivery device has an orientation with at least a vector component of the orientation aligned along an inferior-superior axis relative to the target tissue.

54. The one or more non-transitory, computer-readable media of example 53 wherein the target tissue includes one or more anterior branches of a hypoglossal nerve of the patient, wherein individual ones of the one or more electrodes are configured to deliver the electrical signal to a corresponding one of the one or more anterior branches, and wherein the method further comprises:
  receiving an input corresponding to a tissue collapse pattern of the patient; and
  based at least partially on the input, selecting individual ones of the one or more electrodes to deliver the electrical signal to the corresponding ones of the one or more anterior branches to address the tissue collapse pattern of the patient.

55. The one or more non-transitory, computer-readable media of example 54 wherein each of the one or more anterior branches innervates a muscular compartment of the patient's genioglossus muscle, wherein directing includes directing the electrical signal to the corresponding ones of the one or more anterior branches to cause the corresponding muscular compartment to contract and thereby move a corresponding surface portion of the patient's tongue to reduce or prevent the tissue collapse pattern.

56. The one or more non-transitory, computer-readable media of example 54 wherein the one or more anterior branches innervate muscular compartments of the patient's genioglossus muscle, wherein directing includes directing the electrical signal to individual ones of the one or more anterior branches to cause a subset of the muscular compartments to contract and thereby move a surface portion of the patient's tongue to reduce or prevent the tissue collapse pattern.

57. The one or more non-transitory, computer-readable media of example 54 wherein each of the one or more anterior branches innervates a muscular compartment of the patient's genioglossus muscle, and wherein directing includes directing the electrical signal to the corresponding ones of the one or more anterior branches to cause the corresponding muscular compartment to contract and thereby at least partially reduce a pressure of at least a portion of the patient's tongue on the patient's soft palate.

58. The one or more non-transitory, computer-readable media of example 54 wherein each of the one or more anterior branches innervates a muscular compartment of the patient's genioglossus muscle, wherein receiving the input includes receiving an input that the tissue collapse pattern includes tissue collapse in a retropalatal portion of the patient's airway, and wherein directing includes directing the electrical signal to the corresponding ones of the one or more anterior branches to cause the corresponding muscular compartment to contract and thereby increase airflow through the retropalatal portion of the patient's airway.

59. The one or more non-transitory, computer-readable media of example 54 wherein each of the one or more anterior branches innervates a muscular compartment of the patient's genioglossus muscle, wherein receiving the input includes receiving an input that the tissue collapse pattern includes tissue collapse in a retrolingual portion of the patient's airway, and wherein directing includes directing the electrical signal to the corresponding ones of the one or more anterior branches to cause the corresponding muscular compartments to contract and thereby increase airflow through the retrolingual portion of the patient's airway.

60. The one or more non-transitory, computer-readable media of example 53 wherein directing the electrical signal includes transmitting one or more signal delivery parameters to the signal delivery device via an antenna of the signal delivery device.

61. The one or more non-transitory, computer-readable media of example 53 wherein directing the electrical signal includes transmitting one or more signal delivery parameters to the signal delivery device via a wearable device configured to be worn by the patient.

62. The one or more non-transitory, computer-readable media of example 53 wherein the one or more electrodes include an array of electrodes.

63. The one or more non-transitory, computer-readable media of example 53 wherein the target tissue includes one or more anterior branches of a hypoglossal nerve of the patient, wherein individual ones of the one or more electrodes are (i) positioned across at least a subset of the one or more anterior branches when the signal delivery device is implanted in the patient and (ii) configured to deliver the electrical signal to a corresponding one of the one or more anterior branches, and wherein the method further comprises:
  receiving an input corresponding to a tissue collapse pattern of the patient; and
  based at least partially on the input, selecting individual ones of the one or more electrodes to deliver the electrical signal to the corresponding ones of the one or more anterior branches to address the tissue collapse pattern of the patient.

64. The one or more non-transitory, computer-readable media of example 53 wherein the target tissue includes one or more anterior branches of a hypoglossal nerve of the patient, wherein individual ones of the one or more electrodes are (i) positioned transverse to the one or more anterior branches when the signal delivery device is implanted in the patient and (ii) configured to deliver the electrical signal to a corresponding one of the one or more anterior branches, and wherein the method further comprises:
  receiving an input corresponding to a tissue collapse pattern of the patient; and
  based at least partially on the input, selecting individual ones of the one or more electrodes to deliver the electrical signal to the corresponding ones of the one or more anterior branches to address the tissue collapse pattern of the patient.

65. A system for addressing sleep apnea in a patient, the system comprising:
  an electrode array including one or more electrodes and configured to be implanted at least proximate to a target tissue of the patient in an orientation, with at least a vector component of the orientation aligned along an inferior-superior axis; and a controller communicatively coupled to the electrode array and including one or more non-transitory, computer-readable media having instructions that, when executed by one or more processors of the controller, cause the controller to direct an electrical signal to be delivered by the electrode array to the target tissue.

66. The system of example 65 wherein:

the target tissue includes one or more anterior branches of a hypoglossal nerve of the patient;

individual electrodes of the electrode array are configured to deliver the electrical signal to a corresponding one of the one or more anterior branches;

the controller is configured to receive an input corresponding to a tissue collapse pattern of the patient; and the instructions further cause the controller to, based at least partially on the input, select one or more electrodes of the array of electrodes to deliver the electrical signal to the corresponding ones of the one or more anterior branches to address the tissue collapse pattern of the patient.

67. The system of example 66 wherein each of the one or more anterior branches innervates a muscular compartment of the patient's genioglossus muscle, and wherein the instructions that cause the controller to direct the electrical signal include instructions that cause the controller to direct the electrical signal to the corresponding ones of the one or more anterior branches to cause the corresponding muscular compartments to contract and thereby move a corresponding surface portion of the patient's tongue to reduce or prevent the tissue collapse pattern.

68. The system of example 66 wherein the one or more anterior branches innervate muscular compartments of the patient's genioglossus muscle, and wherein the instructions that cause the controller to direct the electrical signal include instructions that cause the controller to direct the electrical signal to individual ones of the one or more anterior branches to cause a subset of the muscular compartments to contract and thereby move a surface portion of the patient's tongue to reduce or prevent the tissue collapse pattern.

69. The system of example 66 wherein each of the one or more anterior branches innervates a muscular compartment of the patient's genioglossus muscle, and wherein the instructions that cause the controller to direct the electrical signal include instructions that cause the controller to direct the electrical signal to the corresponding ones of the one or more anterior branches to cause the corresponding muscular compartment to contract and thereby at least partially reduce a pressure from at least a portion of the patient's tongue on the patient's soft palate.

70. The system of example 66 wherein each of the one or more anterior branches innervates a muscular compartment of the patient's genioglossus muscle, wherein the input includes an input that the tissue collapse pattern includes tissue collapse in a retropalatal portion of the patient's airway, and wherein the instructions that cause the controller to direct the electrical signal include instructions that cause the controller to direct the electrical signal to the corresponding ones of the one or more anterior branches to cause the corresponding muscular compartments to contract and thereby move a corresponding surface portion of the patient's tongue to increase airflow through the retropalatal portion of the patient's airway.

71. The system of example 66 wherein each of the one or more anterior branches innervates a muscular compartment of the patient's genioglossus muscle, wherein the input includes an input that the tissue collapse pattern includes tissue collapse in a retrolingual portion of the patient's airway, and wherein the instructions that cause the controller to direct the electrical signal include instructions that cause the controller to direct the electrical signal to the corresponding ones of the one or more anterior branches to cause the corresponding muscular compartments to contract and thereby move a corresponding surface portion of the patient's tongue to increase airflow through the retrolingual portion of the patient's airway.

72. The system of example 65 wherein the electrode array is positioned across at least a subset of the one or more anterior branches when implanted in the patient.

73. The system of example 65 wherein the electrode array is positioned transverse to the one or more anterior branches when implanted in the patient.

74. The system of example 65, further comprising an implantable signal delivery device including the electrode array and an antenna, wherein the instructions that cause the controller to direct the electrical signal include instructions that cause the controller to transmit one or more signal delivery parameters to the signal delivery device via the antenna.

75. The system of example 65, further comprising a wearable device configured to be worn by the patient and communicatively coupled to the electrode array and the controller, wherein the instructions that cause the controller to direct the electrical signal include instructions that cause the controller to transmit one or more signal delivery parameters to the signal delivery device via the wearable device.

76. The system of example 65, further comprising a signal delivery device implanted at least proximate to the target tissue in the orientation, wherein the signal delivery device includes a housing, and wherein the electrode array is coupled to the housing.

77. The system of example 76 wherein the signal delivery device further includes the controller.

78. A method for addressing a patient's sleep apnea, the method comprising:

programming a controller for an implantable signal delivery device to direct an electrical signal to one or more electrodes of an array of electrodes carried by the implantable signal delivery device for delivery to a target tissue of a patient, wherein the implantable signal delivery device has an orientation with at least a vector component of the orientation aligned along an inferior-superior axis relative to the target tissue.

79. The method of example 78 wherein programming the controller includes programming the controller to transmit one or more signal delivery parameters of the electrical signal to the implantable signal delivery device via an antenna of the implantable signal delivery device.

80. The method of example 78 wherein programming the controller includes programming the controller to transmit one or more signal delivery parameters of the electrical signal to the implantable signal delivery device via a wearable device configured to be worn by the patient.

81. A system for addressing sleep apnea in a patient by selectively delivering an electrical signal to one or more anterior branches of a hypoglossal nerve of the patient, the system comprising:

an electrode array including one or more electrodes configured to be implanted at least proximate to the one or more anterior branches in an orientation, with at least a vector component of the orientation aligned along an inferior-superior axis of the patient, wherein the one or more anterior branches are distal of a medial branch of the hypoglossal nerve; and a controller communicatively coupled to the electrode array and including one or more non-transitory, computer-readable media having instructions that, when executed by one or more processors of the controller, cause the controller to—receive an input corresponding to a tissue collapse pattern of the patient;

based at least partially on the input, select one or more electrodes of the electrode array to deliver an electrical signal to individual ones of the one or more anterior branches to address the tissue collapse pattern of the patient, and deliver the electrical signal to the individual ones of the one or more anterior branches via the selected one or more electrodes.

82. The system of example 81 wherein each of the one or more anterior branches innervate a muscular compartment of the patient's genioglossus muscle, and wherein the instructions includes instructions that cause the controller to deliver the electrical signal to the individual ones of the one or more anterior branches to cause the corresponding muscular compartments to contract and thereby move a corresponding surface portion of the patient's tongue to reduce or prevent the tissue collapse pattern.

83. The system of example 81 or example 82 wherein the one or more anterior branches innervate muscular compartments of the patient's genioglossus muscle, and wherein the instructions include instructions that cause the controller to deliver the electrical signal to individual ones of the one or more anterior branches to cause a subset of the muscular compartments to contract and thereby move a surface portion of the patient's tongue to reduce or prevent the tissue collapse pattern.

84. The system of any of examples 81 to 83 wherein each of the one or more anterior branches innervate a muscular compartment of the patient's genioglossus muscle, and wherein the instructions include instructions that cause the controller to deliver the electrical signal to the individual ones of the one or more anterior branches to cause the corresponding muscular compartment to contract and thereby at least partially reduce a pressure from at least a portion of the patient's tongue on the patient's soft palate.

85. The system of any of examples 81 to 84 wherein each of the one or more anterior branches innervates a muscular compartment of the patient's genioglossus muscle, wherein the input is indicative of the tissue collapse pattern including tissue collapse in a retropalatal portion of the patient's airway, and wherein the instructions include instructions that cause the controller to deliver the electrical signal to the individual ones of the one or more anterior branches to cause the corresponding muscular compartments to contract and thereby move a corresponding surface portion of the patient's tongue to increase airflow through the retropalatal portion of the patient's airway.

86. The system of any of examples 81 to 85 wherein each of the one or more anterior branches innervates a muscular compartment of the patient's genioglossus muscle, wherein the input is indicative of the tissue collapse pattern including tissue collapse in a retrolingual portion of the patient's airway, and wherein the instructions include instructions that cause the controller to deliver the electrical signal to the individual ones of the one or more anterior branches to cause the corresponding muscular compartments to contract and thereby move a corresponding surface portion of the patient's tongue to increase airflow through the retrolingual portion of the patient's airway.

87. A method for addressing a patient's sleep apnea via an electrical signal delivered to one or more anterior branches of a hypoglossal nerve of the patient, the method comprising:

programming a controller for an implantable signal delivery device to—receive an input corresponding to a tissue collapse pattern of the patient;

select, based at least partially on the input, one or more electrodes of an array of electrodes carried by an implantable signal delivery device to deliver the electrical signal to individual ones of the one or more anterior branches to address the tissue collapse pattern of the patient, wherein the implantable signal delivery device has an orientation with at least a vector component of the orientation aligned along an inferior-superior axis relative to the one or more anterior branches and with individual electrodes of the array of electrodes positionable to deliver the electrical signal to a corresponding one of the one or more anterior branches; and direct the electrical signal to the individual ones of the one or more anterior branches via the selected one or more electrodes.

88. The method of example 87 wherein each of the one or more anterior branches innervate a muscular compartment of the patient's genioglossus muscle, and wherein programming includes programming the controller to direct the electrical signal to the individual ones of the one or more anterior branches to cause the corresponding muscular compartments to contract and thereby move a corresponding surface portion of the patient's tongue to reduce or prevent the tissue collapse pattern.

89. The method of example 87 or 88 wherein the one or more anterior branches innervate muscular compartments of the patient's genioglossus muscle, and wherein programming includes programming the controller to direct the electrical signal to individual ones of the one or more anterior branches to cause a subset of the muscular compartments to contract and thereby move a surface portion of the patient's tongue to reduce or prevent the tissue collapse pattern.

90. The method of any of examples 87 to 89 wherein each of the one or more anterior branches innervate a muscular compartment of the patient's genioglossus muscle, and wherein programming includes programming the controller to direct the electrical signal to the individual ones of the one or more anterior branches to cause the corresponding muscular compartment to contract and thereby at least partially reduce a pressure from at least a portion of the patient's tongue on the patient's soft palate.

91. The method of any of examples 87 to 90 wherein each of the one or more anterior branches innervates a muscular compartment of the patient's genioglossus muscle, wherein the input is indicative of the tissue collapse pattern including tissue collapse in a retropalatal portion of the patient's airway, and wherein programming includes programming the controller to direct the electrical signal to the individual ones of the one or more anterior branches to cause the corresponding muscular compartments to contract and thereby move a corresponding surface portion of the patient's tongue to increase airflow through the retropalatal portion of the patient's airway.

92. The method of any of examples 87 to 91 wherein each of the one or more anterior branches innervates a muscular compartment of the patient's genioglossus muscle, wherein the input is indicative of the tissue collapse pattern including tissue collapse in a retrolingual portion of the patient's airway, and wherein programming includes programming the controller to direct the electrical signal to the individual ones of the one or more anterior branches to cause the corresponding muscular compartments to contract and thereby move a corresponding surface portion of the patient's tongue to increase airflow through the retrolingual portion of the patient's airway.

93. A system for addressing sleep apnea in a patient, the system comprising:
 an electrode array including one or more electrodes and configured to be implanted at least proximate to a target tissue of the patient in an orientation, with at least a vector component of the orientation aligned along an inferior-superior axis of the patient; and
 a controller communicatively coupled to the electrode array and including one or more non-transitory, computer-readable media having instructions that, when executed by one or more processors of the controller, cause the controller to direct an electrical signal to be delivered by the electrode array to the target tissue.

94. The system of example 93 wherein the target tissue includes one or more anterior branches of the patient's hypoglossal nerve, and wherein the electrode array is positioned across at least a subset of the one or more anterior branches when implanted in the patient.

95. The system of any of examples 93 to 94 wherein the target tissue includes one or more anterior branches of the patient's hypoglossal nerve, and wherein the electrode array is positioned transverse to the one or more anterior branches when implanted in the patient.

96. The system of any of examples 93 to 95 wherein the target tissue includes one or more branches of the patient's hypoglossal nerve distal of a medial branch of the patient's hypoglossal nerve, and wherein the electrode array is implanted within the patient to deliver the electrical signal to individual ones of the one or more branches.

97. The system of any of examples 93 to 96 wherein the target tissue includes a genioglossus muscle of the patient, and wherein the electrode array is implanted within the genioglossus muscle in the orientation.

98. The system of any of examples 93 to 97 wherein the target tissue includes one or both of a left genioglossus muscle of the patient and a right genioglossus muscle of the patient, and wherein the electrode array is implanted in the orientation and at least partially between the left genioglossus muscle and the right genioglossus muscle.

99. The system of any of examples 93 to 98, further comprising an implantable signal delivery device including the electrode array and an antenna, wherein the instructions that cause the controller to direct the electrical signal include instructions that cause the controller to transmit one or more signal delivery parameters to the implantable signal delivery device via the antenna.

100. The system of any of examples 93 to 99, further comprising a wearable device configured to be worn by the patient and communicatively coupled to the electrode array and the controller, wherein the instructions that cause the controller to direct the electrical signal include instructions that cause the controller to transmit one or more signal delivery parameters to the implantable signal delivery device via the wearable device.

101. The system of any of examples 93 to 100, further comprising a signal delivery device implanted at least proximate to the target tissue in the orientation, wherein the signal delivery device includes a housing, and wherein the electrode array is coupled to the housing.

102. The system of example 101 wherein the signal delivery device further includes the controller.

103. A method for addressing a patient's sleep apnea, the method comprising:
 programming a controller for an implantable signal delivery device to direct an electrical signal to one or more electrodes of an array of electrodes carried by the implantable signal delivery device for delivery to a target tissue of a patient, wherein the implantable signal delivery device has an orientation with at least a vector component of the orientation aligned along or configured to be aligned along an inferior-superior axis relative to the target tissue.

104. The method of example 103 wherein programming the controller includes programming the controller to transmit one or more signal delivery parameters of the electrical signal to the implantable signal delivery device via an antenna of the implantable signal delivery device.

105. The method of example 103 or 104 wherein programming the controller includes programming the controller to transmit one or more signal delivery parameters of the electrical signal to the implantable signal delivery device via a wearable device configured to be worn by the patient.

106. The method of any of examples 103 to 105 wherein the target tissue includes one or more anterior branches of the patient's hypoglossal nerve, the method further comprising implanting the implantable signal delivery device at least proximate to the one or more anterior branches in the orientation.

107. The method of any of examples 103 to 106 wherein implanting the implantable signal delivery device at least proximate to the one or more anterior branches includes positioning at least a portion of the implantable signal delivery device distal from the medial branch of a hypoglossal nerve of the patient.

108. The method of any of examples 103 to 107 wherein the target tissue includes at least one genioglossus muscle of the patient.

109. The method of example 108, further comprising implanting the implantable signal delivery device proximate to or within the genioglossus muscle.

110. The method of example 108 or 109 wherein implanting includes positioning at least a portion of the implantable signal delivery device between a left genioglossus muscle of the patient and a right genioglossus muscle of the patient.

From the foregoing, it is believed that positioning a signal delivery device to deliver an electrical signal to one or more of the anterior branches AB of the hypoglossal nerve HGN and/or the genioglossus muscle GG as described herein can reduce or prevent retruser stimulation and/or produce a net positive protrusive response (e.g., a protrusive response greater than the retrusive response). In at least some embodiments, applying electrical signals to one or more of the anterior branches AB and/or directly to one or both of the patient's genioglossus muscles GG is expected to provide a gradual dose-response activation and thereby evoke a gradual patient motor response. Additionally, or alternatively, positioning/orienting the signal delivery device such that at least a vector component of the orientation of the signal delivery device is aligned with the inferior-superior axis is expected to reduce the amount of power required to produce effective therapy signals and/or increase an amount of the target tissue (e.g., a number of the anterior branches AB) that receives the electrical signal from the signal delivery device. This can include, for example, positioning the signal delivery device to be transverse to one or more of the anterior branches AB. In these and other embodiments, the positions/orientations described herein are expected to reduce or minimize changes to the position/orientation of the signal delivery device during insertion and/or after implantation, and/or increase the speed and/or precision with which the signal delivery device can be positioned at least proximate to the target location.

It will be appreciated that specific embodiments of the disclosed technology have been described herein for purposes of illustration, but that various modifications may be made without deviating from the technology. For example, the signal delivery device can include a lead, and one or more of the electrodes of the signal delivery device can be carried by the lead. In some embodiments, at least a portion (e.g., a lead portion) of the signal delivery device can be flexible or curved (e.g., arcuate, helical, etc.). Curved signal delivery devices are expected to have improved stability compared to other signal delivery devices. In some embodiments, a first end of the signal delivery device can lead a second, opposite end of the signal delivery device during insertion while, in other embodiments, the second end can lead the first end. Certain aspects of the technology described in the context of particular embodiments may be combined or eliminated in other embodiments. For example, two signal delivery devices can be implanted to bilaterally target the patient's tissues (e.g., left and right anterior branches of the hypoglossal nerves) and/or to target different tissues on the left and right sides of the patient (e.g., left anterior branches of the hypoglossal nerve and a right genioglossus muscle of the patient). Further, while advantages associated with certain embodiments of the disclosed technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

As used herein, the phrase "and/or," as in "A and/or B," refers to A alone, B alone, and both A and B. As used herein, the terms "about" and "approximately" refer to values within 10% of the stated value.

To the extent any materials incorporated herein by reference conflict with the present disclosure, the present disclosure controls.

We claim:

1. A system for addressing sleep apnea in a patient by selectively delivering an electrical signal to one or more anterior branches of a hypoglossal nerve of the patient, the system comprising:
   an electrode array including one or more electrodes configured to be implanted at least proximate to the one or more anterior branches in an orientation, with at least a vector component of the orientation aligned along an inferior-superior axis of the patient, wherein the one or more anterior branches are distal of a medial branch of the hypoglossal nerve; and
   a controller communicatively coupled to the electrode array and including one or more non-transitory, computer-readable media having instructions that, when executed by one or more processors of the controller, cause the controller to—
   receive an input identifying a tissue collapse location within the patient;
   based at least partially on the input, select one or more electrodes of the electrode array to deliver an electrical signal to individual ones of the one or more anterior branches to address tissue collapse at the tissue collapse location, and
   deliver the electrical signal to the individual ones of the one or more anterior branches via the selected one or more electrodes.

2. The system of claim 1 wherein each of the one or more anterior branches innervate a muscular compartment of the patient's genioglossus muscle, and wherein the instructions includes instructions that cause the controller to deliver the electrical signal to the individual ones of the one or more anterior branches to cause the corresponding muscular compartments to contract and thereby move a corresponding surface portion of the patient's tongue to reduce or prevent the tissue collapse.

3. The system of claim 1 wherein the one or more anterior branches innervate muscular compartments of the patient's genioglossus muscle, and wherein the instructions include instructions that cause the controller to deliver the electrical signal to individual ones of the one or more anterior branches to cause a subset of the muscular compartments to contract and thereby move a surface portion of the patient's tongue to reduce or prevent the tissue collapse.

4. The system of claim 1 wherein—
   each of the one or more anterior branches innervates a muscular compartment of the patient's genioglossus muscle,
   the input is indicative of the tissue collapse location including a retropalatal portion and a retrolingual portion of the patient's airway, and
   the instructions include instructions that cause the controller to deliver the electrical signal to the individual ones of the one or more anterior branches to cause the corresponding muscular compartments to contract and thereby move corresponding surface portions of the patient's tongue to—
   increase airflow through the retropalatal portion of the patient's airway,
   increase airflow through the retrolingual portion of the patient's airway, and
   at least partially reduce a pressure from at least a portion of the patient's tongue on the patient's soft palate.

5. The system of claim 1 wherein each of the one or more anterior branches innervate a muscular compartment of the patient's genioglossus muscle, and wherein the instructions include instructions that cause the controller to deliver the electrical signal to the individual ones of the one or more anterior branches to cause the corresponding muscular compartment to contract and thereby at least partially reduce a pressure from at least a portion of the patient's tongue on the patient's soft palate.

6. The system of claim 1 wherein each of the one or more anterior branches innervates a muscular compartment of the patient's genioglossus muscle, wherein the input 1s indicative of the tissue collapse pattern including tissue collapse in a retropalatal portion of the patient's airway, and wherein the instructions include instructions that cause the controller to deliver the electrical signal to the individual ones of the one or more anterior branches to cause the corresponding muscular compartments to contract and thereby move a corresponding surface portion of the patient's tongue to increase airflow through the retropalatal portion of the patient's airway.

7. The system of claim 1 wherein each of the one or more anterior branches innervates a muscular compartment of the patient's genioglossus muscle, wherein the input is indicative of the tissue collapse pattern including tissue collapse in a retrolingual portion of the patient's airway, and wherein the instructions include instructions that cause the controller to deliver the electrical signal to the individual ones of the one or more anterior branches to cause the corresponding muscular compartments to contract and thereby move a corresponding surface portion of the patient's tongue to increase airflow through the retrolingual portion of the patient's airway.

8. A method for addressing a patient's sleep apnea via an electrical signal delivered to one or more anterior branches of a hypoglossal nerve of the patient, the method comprising:

programming a controller for an implantable signal delivery device to—
receive an input identifying a tissue collapse location within the patient;
select, based at least partially on the input, one or more electrodes of an array of electrodes carried by an implantable signal delivery device to deliver the electrical signal to individual ones of the one or more anterior branches to address tissue collapse at the tissue collapse location, wherein the implantable signal delivery device has an orientation with at least a vector component of the orientation aligned along an inferior-superior axis relative to the one or more anterior branches and with individual electrodes of the array of electrodes positionable to deliver the electrical signal to a corresponding one of the one or more anterior branches; and
direct the electrical signal to the individual ones of the one or more anterior branches via the selected one or more electrodes.

9. The method of claim 8 wherein each of the one or more anterior branches innervate a muscular compartment of the patient's genioglossus muscle, and wherein programming includes programming the controller to direct the electrical signal to the individual ones of the one or more anterior branches to cause the corresponding muscular compartments to contract and thereby move a corresponding surface portion of the patient's tongue to reduce or prevent the tissue collapse.

10. The method of claim 8 wherein the one or more anterior branches innervate muscular compartments of the patient's genioglossus muscle, and wherein programming includes programming the controller to direct the electrical signal to individual ones of the one or more anterior branches to cause a subset of the muscular compartments to contract and thereby move a surface portion of the patient's tongue to reduce or prevent the tissue collapse.

11. The method of claim 8 wherein—
each of the one or more anterior branches innervates a muscular compartment of the patient's genioglossus muscle,
the input is indicative of the tissue collapse location including a retropalatal portion and a retrolingual portion of the patient's airway, and
programming includes programming the controller to direct the electrical signal to the individual ones of the one or more anterior branches to cause the corresponding muscular compartments to contract and thereby move corresponding surface portions of the patient's tongue to—
increase airflow through the retropalatal portion of the patient's airway,
increase airflow through the retrolingual portion of the patient's airway, and
at least partially reduce a pressure from at least a portion of the patient's tongue on the patient's soft palate.

12. The method of claim 8, further comprising implanting the implantable signal delivery device in the orientation and transverse to the hypoglossal nerve.

13. The method of claim 8 wherein each of the one or more anterior branches innervate a muscular compartment of the patient's genioglossus muscle, and wherein programming includes programming the controller to direct the electrical signal to the individual ones of the one or more anterior branches to cause the corresponding muscular compartment to contract and thereby at least partially reduce a pressure from at least a portion of the patient's tongue on the patient's soft palate.

14. The method of claim 8 wherein each of the one or more anterior branches innervates a muscular compartment of the patient's genioglossus muscle, wherein the input is indicative of the tissue collapse pattern including tissue collapse in a retropalatal portion of the patient's airway, and wherein programming includes programming the controller to direct the electrical signal to the individual ones of the one or more anterior branches to cause the corresponding muscular compartments to contract and thereby move a corresponding surface portion of the patient's tongue to increase airflow through the retropalatal portion of the patient's airway.

15. The method of claim 8 wherein each of the one or more anterior branches innervates a muscular compartment of the patient's genioglossus muscle, wherein the input is indicative of the tissue collapse pattern including tissue collapse in a retrolingual portion of the patient's airway, and wherein programming includes programming the controller to direct the electrical signal to the individual ones of the one or more anterior branches to cause the corresponding muscular compartments to contract and thereby move a corresponding surface portion of the patient's tongue to increase airflow through the retrolingual portion of the patient's airway.

* * * * *

UNITED STATES PATENT AND TRADEMARK OFFICE
CERTIFICATE OF CORRECTION

PATENT NO. : 11,964,154 B1
APPLICATION NO. : 18/331109
DATED : April 23, 2024
INVENTOR(S) : Guillaume Raux et al.

It is certified that error appears in the above-identified patent and that said Letters Patent is hereby corrected as shown below:

On the Title Page

In item (74), in Column 2, in "attorney agent, or firm", Line 1, delete "Perkins Cole LLP" and insert -- Perkins Coie LLP --.

On the page 3, in item (56), in Column 1, under "U.S. Patent Documents", Line 10, delete "Bachelder" and insert -- Bachelder et al. --.

On the page 3, in item (56), in Column 2, under "Other Publications", Line 2, delete "Cervivalis,"" and insert -- Cervicalis," --.

On the page 3, in item (56), in Column 2, under "Other Publications", Line 39, delete ""Hypogloassal" and insert -- "Hypoglossal --.

In the Specification

In Column 6, Line 36, delete "Jr," and insert -- Ir, --.

In Column 9, Line 37, delete "CI" and insert -- C1 --.

In Column 21, Line 25, delete "$GG_R$," and insert -- $GG_R$. --.

In the Claims

In Column 42, Line 55, in Claim 6, delete "1s" and insert -- is --.

Signed and Sealed this
Twenty-fifth Day of June, 2024

Katherine Kelly Vidal
*Director of the United States Patent and Trademark Office*